US007115652B2

(12) United States Patent
Yang

(10) Patent No.: US 7,115,652 B2
(45) Date of Patent: Oct. 3, 2006

(54) ASPARTYL PROTEASE INHIBITORS

(75) Inventor: Wenjin Yang, Foster City, CA (US)

(73) Assignee: Sunesis Pharmaceuticals, Inc., South San Francisco, CA (US)

( * ) Notice: Subject to any disclaimer, the term of this patent is extended or adjusted under 35 U.S.C. 154(b) by 47 days.

(21) Appl. No.: 10/731,922

(22) Filed: Dec. 10, 2003

(65) Prior Publication Data

US 2004/0147454 A1    Jul. 29, 2004

Related U.S. Application Data

(63) Continuation-in-part of application No. 10/462,127, filed on Jun. 16, 2003.

(60) Provisional application No. 60/430,693, filed on Dec. 3, 2002, provisional application No. 60/389,194, filed on Jun. 17, 2002.

(51) Int. Cl.
$A61K\ 31/38$ (2006.01)
$C07D\ 333/22$ (2006.01)

(52) U.S. Cl. ............................ 514/438; 549/76; 549/77

(58) Field of Classification Search ................ 514/438; 549/76, 77
See application file for complete search history.

(56) References Cited

U.S. PATENT DOCUMENTS

| | | | |
|---|---|---|---|
| 5,196,438 A | 3/1993 | Martin et al. | 514/311 |
| 5,413,999 A | 5/1995 | Vacca et al. | 514/231.5 |
| 5,585,397 A | 12/1996 | Tung et al. | 514/473 |
| 5,728,718 A | 3/1998 | Randad et al. | 514/357 |

FOREIGN PATENT DOCUMENTS

| | | |
|---|---|---|
| AU | 634756 | 4/1993 |
| EP | 0 316 965 A | 5/1989 |
| EP | 0 356 223 A2 | 2/1990 |
| EP | 0 386 611 A2 | 9/1990 |
| WO | WO 93/02674 | 2/1993 |
| WO | WO 98/46599 | 10/1998 |
| WO | WO 00/56335 A | 3/2000 |
| WO | WO 00/40558 | 7/2000 |
| WO | WO 02/02505 A2 | 1/2002 |

OTHER PUBLICATIONS

*Ajay, et al., "Designing Libraries with CNS Activity", *J. Med. Chem.*, 42:4942-4951, 1999.
Brožková, et al., "Peptidomimetic Inhibitors of Extracellular Aspartic Proteinases of *Candida albicans* AND *Candida trooicalis*", Collect. Czech. Chem. Commun., 64:130-137, 1999.
*Ermolieff, et al., "Proteolytic Activation of Recombinant Pro-Memapsin 2 (Pro-β-secretase) Studied with New Fluorogenic Substrates", *Biochemistry*, 39:12450-12456, 2000.
*Haque, et al., "Potent, Low-Molecular-Weight Non-Peptide Inhibitors of Malarial Aspartyl Protease Plasmepsin II", *J. Med. Chem.*, 42: 1428-1440, 1999.
Herrero, et al. "C-Backbone ranches peptides via reductive amination of cyanomethyleneamino pseudopeptides", Tetrahedron Letters, 43: 1421-1424, 2002.
*Hussain, et al., "Identification of a Novel Aspartic Protease (Asp 2) as β-Secretase", *Mol. Cell. Neurosci.*, 14:419-427, 1999.
*Sabbagh, et al., "β-Amyloid and Treatment Opportunities for Alzheimer's Disease", *Alz. Dis. Rev.* , 3:1-19, 1997.
*Sinha, et al., "Purification and cloning of amyloid precursor protein β-secretase from human brain", *Nature*, 402:537-540, 1999.
Suárez-Gea, et al., "Branches Peptides and Conformationally Constrained Analogues form Cyanomethyleneamino Pseudopeptides", Tetrahedron Letters, 37:2083-2084, 1996.
*Vassar, et al., "β-Secretase Cleavage of Alzheimer's Amyloid Precursor Protein by Transmembrane Aspartic Protease BACE", *Science*, 286:735-741, 1999.
Wolfe, et al., "A Substrate-Based Difluoro Ketone Selectively Inhibits Alzheimer's γ-Secretase Activity", J. Med. Chem., 41:6-9, 1998.
*Yan, et al., Membrane-anchored aspartyl protease with Alzheimer's disease β-secretase activity, *Nature*, 402:533-537, 1999.
International Search Report issued for PCT application PCT/US03/18858.

*Primary Examiner*—Deborah C. Lambkin
(74) *Attorney, Agent, or Firm*—Choate, Hall & Stewart LLP; Brenda Herschbach Jarrell; Nadège M. Lagneau

(57) ABSTRACT

The present invention provides compounds having the formula:

(I)

$$R^1\!-\!X^1\!-\!N\!\overset{R'}{\underset{R^2}{|}}\!\!\overset{NH_2}{\underset{R^3}{|}}\!\!\overset{}{\underset{R^{3'}}{|}}\!X^2\!-\!X^3\!-\!R^4$$

wherein $R^1$, $R'$, $R^2$, $R^3$, $R^{3'}$, $R^4$, $X^1$, $X^2$ and $X^3$ are as defined herein, and pharmaceutical compositions thereof. The present invention also provides methods of inhibiting proteases, more specifically aspartyl proteases. In certain embodiments, compounds inhibit BACE (β-site APP-cleaving enzyme), and thus are useful in the treatment or prevention of a disease characterized by β-amyloid deposits in the brain (including, but not limited to, Alzheimer's Disease). The present invention also provides methods for preparing compounds of the invention.

29 Claims, 1 Drawing Sheet

ASPARTYL PROTEASE INHIBITORS

PRIORITY CLAIM

The present application is a Continuation-In-Part of U.S. patent application Ser. No. 10/462,127; filed Jun. 16, 2003, which claims priority under 35 U.S.C. § 119(e) to U.S. Ser. No. 60/430,693, filed Dec. 3, 2002, and U.S. Ser. No. 60/389,194, filed Jun. 17, 2002. The present application additionally claims priority to Patent Cooperation Treaty Application No.: PCT/US03/18858, filed Jun. 16, 2003. The entire contents of each of the above-referenced applications are incorporated herein by reference.

BACKGROUND OF THE INVENTION

Alzheimer's Disease is a progressive dementia in which massive deposits of aggregated protein breakdown products (β-amyloid plaques and neurofibrillary tangles) accumulate in the brain, resulting in the loss of memory, cognition, reasoning, judgement, orientation, and eventually death. Current therapies for the treatment of Alzheimer's Disease include, but are not limited to, donepezil and tacrine. These therapies are useful for improving the memory of patients during the early stages of Alzheimer's Disease, however they do not modify the progression of aggregated protein breakdown products underlying the pathology of Alzheimer's Disease. It would be desirable to develop therapies that would either stop or slow down this process of aggregation.

As described above, a defining feature of Alzheimer's Disease which is often used during clinical diagnosis is the presence of β-amyloid plaques and neurofibrillary tangles. β-amyloid plaques are predominantly composed of amyloid β peptide (Aβ (or βA4), which is derived by proteolysis of the amyloid precursor protein (APP). Proteolysis of the amyloid precursor protein is effected by several enzymes called secretases. More specifically, cleavage of APP at the N-terminus of the Aβ peptide by β-secretase and at the C-terminus by one or more γ-secretases constitutes the β-amyloidogenic pathway, i.e., the pathway by which Aβ is formed. It is believed that Aβ peptide accumulates as a result of this APP processing by β-secretase and thus inhibition of this enzyme's activity is desirable for the treatment of Alzheimer's Disease. For example, in vivo processing of APP at the β-secretase cleavage site is thought to be a rate limiting step in Aβ production, and is thus believed to be a therapeutic target for Alzheimer's Disease (Sabbagh et al. *Alz. Dis. Rev.* 1997, 3, 1–19). Recently, an aspartyl protease (known as BACE, Asp2, Memapsin) has been identified as the enzyme responsible for processing of APP at the β-secretase cleavage site (see, for example, Vassar, et al. *Science,* 1999, 286, 735–741; Yan et al. *Nature,* 1999, 402, 533–537; Sinha et al. *Nature,* 1999, 402, 537–540; and Hussain et al. *Mol. Cell. Neurosci.* 1999, 14, 419–427).

Because it is believed that BACE plays an important role in the development and pathogenesis of Alzheimer's Disease, there has been increasing interest in the development of inhibitors of BACE as treatments (and possibly as preventative agents) for Alzheimer's Disease and other disorders caused by the accumulation of β-amyloid plaques. There remains a need, however, for the development of novel therapeutics capable of inhibiting the activity of this aspartyl protease. In particular, it would be desirable to develop therapeutics capable of selectively inhibiting BACE.

SUMMARY OF THE INVENTION

As discussed above, there remains a need for the development of novel therapeutic agents and agents useful for treating disorders mediated by aspartyl proteases. The present invention provides novel compounds having the structure:

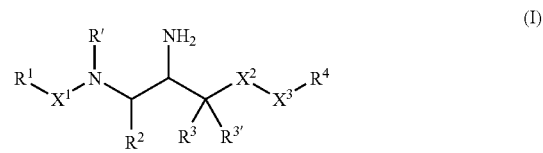

and pharmaceutical compositions thereof, as described generally and in subclasses herein, which compounds are useful as inhibitors of aspartyl proteases, and thus are useful, for example, for the treatment of Alzheimer's Disease.

In certain other embodiments, the invention provides pharmaceutical compositions comprising an inventive compound, wherein the compound is present in an amount effective to inhibit β-secretase activity. In certain other embodiments, the invention provides pharmaceutical compositions comprising an inventive compound and optionally further comprising an additional therapeutic agent. In yet other embodiments, the additional therapeutic agent is an agent for the treatment of Alzheimer's Disease.

In yet another aspect, the present invention provides methods for inhibiting β-secretase activity in a patient or a biological sample, comprising administering to said patient, or contacting said biological sample with an effective inhibitory amount of a compound of the invention. In still another aspect, the present invention provides methods for treating any disorder involving β-secretase activity, comprising administering to a subject in need thereof a therapeutically effective amount of a compound of the invention. In certain other embodiments, the invention provides a method for treating or preventing a disease characterized by β-amyloid deposits in the brain comprising administering to a patient a therapeutically effective amount of a compound of the invention.

DEFINITIONS

Figure 1A:
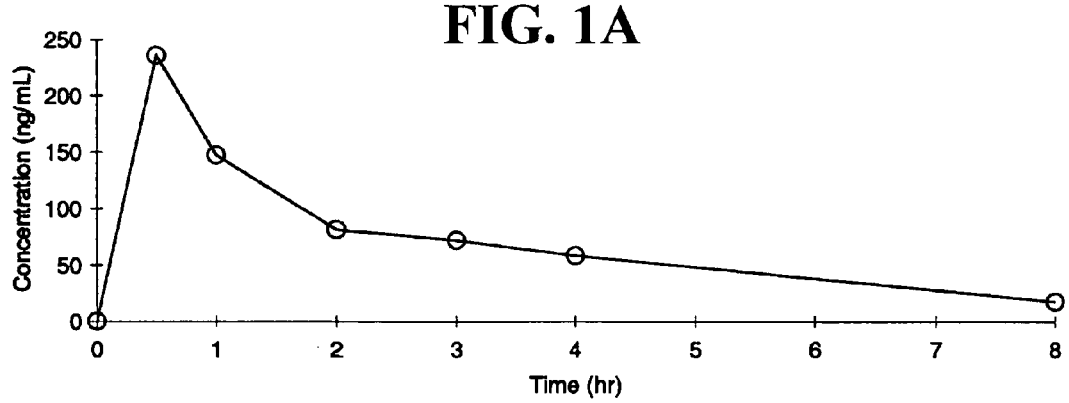
FIG. 1A depicts a plasma concentration curve for an exemplary inventive compound.

Certain compounds of the present invention, and definitions of specific functional groups are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group", has used herein, it is meant that a particular functional moiety, e.g., O, S, or N, is temporarily blocked so that a reaction can be carried out selectively at another reactive site in a multi-functional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group may form an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment and prevention, for example of disorders, as described generally above. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched), branched, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (cyclic, acyclic, substituted, unsubstituted, branched or unbranched) having 1–6 carbon atoms.

In certain embodiments, the alkyl, alkenyl and alkynyl groups employed in the invention contain 1–20 aliphatic carbon atoms. In certain other embodiments, the alkyl, alkenyl, and alkynyl groups employed in the invention contain 1–10 aliphatic carbon atoms. In yet other embodiments, the alkyl, alkenyl, and alkynyl groups employed in the invention contain 1–8 aliphatic carbon atoms. In still other embodiments, the alkyl, alkenyl, and alkynyl groups employed in the invention contain 1–6 aliphatic carbon atoms. In yet other embodiments, the alkyl, alkenyl, and alkynyl groups employed in the invention contain 1–4 carbon atoms. Illustrative aliphatic groups thus include, but are not limited to, for example, methyl, ethyl, n-propyl, isopropyl, cyclopropyl, —$CH_2$-cyclopropyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl-n, hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1–20 aliphatic carbon atoms. In certain other embodiments, the alkyl group contains 1–10 aliphatic carbon atoms. In yet other embodiments, the alkyl, alkenyl, and alkynyl groups employed in the invention contain 1–8 aliphatic carbon atoms. In still other embodiments, the alkyl group contains 1–6 aliphatic carbon atoms. In yet other embodiments, the alkyl group contains 1–4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "dialkylamino" refers to a group having the structure —N(R')$_2$, wherein R' is alkyl, as defined herein. The term "aminoalkyl" refers to a group having the structure NH$_2$R'—, wherein R' is alkyl, as defined herein. In certain embodiments, the alkyl group contains 1–20 aliphatic carbon atoms. In certain other embodiments, the alkyl group contains 1–10 aliphatic carbon atoms. In yet other embodiments, the alkyl, alkenyl, and alkynyl groups employed in the invention contain 1–8 aliphatic carbon atoms. In still other embodiments, the alkyl group contains 1–6 aliphatic carbon atoms. In yet other embodiments, the alkyl group contains 1–4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$; —N(R$_x$) CO$_2$R$_x$; —N(R$_x$)S(O)$_2$R$_x$; —N(R$_x$)C(=O)N(R$_x$)$_2$; —S(O)$_2$ N(R$_x$)$_2$; wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl, heteroaryl, -(alkyl)aryl or -(alkyl)heteroaryl substituents described above and herein may be substituted or unsubstituted. Additional examples of generally applicable substituents are illustrated by the specific embodiments shown in the Examples that are described herein.

In general, the terms "aromatic moiety" and "heteroaromatic moiety", as used herein, refer to stable mono- or polycyclic, heterocyclic, polycyclic, and polyheterocyclic unsaturated moieties having preferably 3–14 carbon atoms, each of which may be substituted or unsubstituted. It will also be appreciated that aromatic and heteroaromatic moieties, as defined herein may be attached via an alkyl or heteroalkyl moiety and thus also include -(alkyl)aromatic, -(heteroalkyl)aromatic, -(heteroalkyl)heteroaromatic, and -(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and -(heteroalkyl)heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

The term "aryl", as used herein, does not differ significantly from the common meaning of the term in the art, and refers to a mono- or bicyclic carbocyclic ring system having one or two aromatic rings including, but not limited to, phenyl, naphthyl, tetrahydronaphthyl, indanyl, indenyl and the like.

The term "heteroaryl", as used herein, does not differ significantly from the common meaning of the term in the art, and refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$; —N(R$_x$) CO$_2$R$_x$; —N(R$_x$)S(O)$_2$R$_x$; —N(R$_x$)C(=O)N(R$_x$)$_2$; —S(O)$_2$ N(R$_x$)$_2$; wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered cyclic, substituted or unsubstituted aliphatic or heteroaliphatic moiety. Additional examples of generally applicable substituents are illustrated by the specific embodiments shown in the Examples that are described herein.

The term "cycloalkyl", as used herein, refers specifically to cyclic moieties having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic or heterocyclic moieties, may optionally be substituted with substituents including, but not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$; —N(R$_x$) CO$_2$R$_x$; —N(R$_x$)S(O)$_2$R$_x$; —N(R$_x$)C(=O)N(R$_x$)$_2$; —S(O)$_2$ N(R$_x$)$_2$; wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl, heteroaryl, -(alkyl)aryl or -(alkyl)heteroaryl substituents described above and herein may be substituted or unsubstituted. Additionally, it will be appreciated that any of the cycloaliphatic or cycloheteroaliphatic moieties described above and herein may comprise an aryl, heteroaryl, -(alkyl)aryl or -(alkyl)heteroaryl moiety fused thereto. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen sulfur, nitrogen, phosphorus or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl, heteroaryl, -(alkyl)aryl or -(alkyl)heteroaryl substituents described above and herein may be substituted or unsubstituted.

In general, the term "cycloaliphatic", as used herein, refer to a cyclic aliphatic moiety, wherein the term aliphatic is as defined above. A cycloaliphatic moiety may be substituted or unsubstituted and saturated or unsaturated. Substituents include, but are not limited to, any of the previously mentioned substituents, i.e., the substituents recited for aliphatic moieties, or for other moieties as disclosed herein, resulting in the formation of a stable compound. In certain embodiments, cycloaliphatic compounds include but are not limited to monocyclic, or polycyclic aliphatic hydrocarbons and bridged cycloalkyl compounds, which are optionally substituted with one or more functional groups. As will be appreciated by one of ordinary skill in the art, "cycloaliphatic" is intended herein to include, but is not limited to, cycloalkyl, cycloalkenyl, and cycloalkynyl moieties, which are optionally substituted with one or more functional groups. Illustrative cycloaliphatic groups thus include, but are not limited to, for example, cyclopropyl, —CH$_2$-cyclopropyl, cyclobutyl, —CH$_2$-cyclobutyl, cyclopentyl, —CH$_2$-cyclopentyl, cyclohexyl, —CH$_2$-cyclohexyl, cyclohexenylethyl, cyclohexanylethyl, norborbyl moieties and the like, which again, may bear one or more substituents.

In general, the term "cycloheteroaliphatic", as used herein, refers to a cyclic heteroaliphatic moiety, wherein the term heteroaliphatic is as defined above. A cycloheteroaliphatic moiety may be substituted or unsubstituted and saturated or unsaturated. Substituents include, but are not limited to, any of the previously mentioned substituents, i.e., the substituents recited for aliphatic moieties, or for other moieties as disclosed herein, resulting in the formation of a stable compound. The term "cycloheteroaliphatic" encompasses "heterocycloalkyl", "heterocycle" or "heterocyclic" moieties, as defined herein.

Additionally, it will be appreciated that any of the cycloaliphatic or cycloheteroaliphatic moieties described above and herein may comprise an aryl, heteroaryl, -(alkyl)aryl or -(alkyl)heteroaryl moiety fused thereto. Additional examples of generally applicable substituents are illustrated by the specific embodiments shown in the Examples that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "acyl", as used herein, refers to a group having the general formula —C(=O)R, where R is an aliphatic, heteroaliphatic, heterocycle, aromatic or heteroaromatic moiety, as defined herein.

The term "heterocycloalkyl", "heterocycle" or "heterocyclic", as used herein, refers to compounds which combine the properties of heteroaliphatic and cyclic compounds and include, but are not limited to, saturated and unsaturated mono- or polycyclic cyclic ring systems having 5–16 atoms wherein at least one ring atom is a heteroatom selected from O, S and N (wherein the nitrogen and sulfur heteroatoms may be optionally be oxidized), wherein the ring systems are optionally substituted with one or more functional groups, as defined herein. In certain embodiments, the term "heterocycloalkyl", "heterocycle" or "heterocyclic" refers to a non-aromatic 5-, 6- or 7-membered ring or a polycyclic group wherein at least one ring atom is a heteroatom selected from O, S and N (wherein the nitrogen and sulfur heteroatoms may be optionally be oxidized), including, but not limited to, a bi- or tri-cyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, thiofuranyl, pyranyl, pyrrolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof. In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two or three of the hydrogen atoms thereon with but are not limited to aliphatic; cycloaliphatic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, cycloaliphatic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, cycloaliphatic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substitutents described above and herein may be substituted or unsubstituted. Additional examples or generally applicable substituents are illustrated by the specific embodiments shown in the Examples, which are described herein.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heterocyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aromatic", "heteroaromatic", "aryl", "heteroaryl" and the like encompass both substituted and unsubstituted groups.

As used herein, the term "isolated", when applied to the compounds of the present invention, refers to such compounds that are (i) separated from at least some components with which they are associated in nature or when they are made and/or (ii) produced, prepared or manufactured by the hand of man.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety that is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

The term "treating", as used herein generally means that the compounds of the invention can be used in humans or animals with at least a tentative diagnosis of disease. The compounds of the invention will delay or slow the progression of the disease thereby giving the individual a more useful life span.

The term "preventing" as used herein means that the compounds of the present invention are useful when administered to a patient who has not been diagnosed as possibly having the disease at the time of administration, but who would normally be expected to develop the disease or be at increased risk for the disease. The compounds of the invention will slow the development of disease symptoms, delay the onset of disease, or prevent the individual from developing the disease at all. Preventing also includes administration of the compounds of the invention to those individuals thought to be predisposed to the disease due to age, familial history, genetic or chromosomal abnormalities, and/or due to the presence of one or more biological markers for the disease, such as a known genetic mutation of APP or APP cleavage products in brain tissues or fluids.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof. For example, the term "biological sample" refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

DESCRIPTION OF CERTAIN PREFERRED EMBODIMENTS OF THE INVENTION

As noted above, there has been increasing interest ion recent years in the development of aspartyl protease inhibitors, particularly BACE inhibitors, as therapeutic agents for the treatment of Alzheimer's Disease and other disorders caused by the accumulation of β-amyloid plaques. It has been generally accepted by the scientific community that potential new leads for aspartyl inhibitor small molecules must comprise an aspartate binding hydroxyl group to retain aspartyl protease inhibitory activity (See for example, Ajay et al., "Designing Libraries woth CNS Activity", *J. Med. Chem.*, 42:4942–4951, 1999, see especially the paragraph bridging columns 1 and 2 on page 4942 of this article). The present invention demonstrates that amino analogs (i.e., where the hydroxyl group has been replaced with an amino group) are unexpectedly equally promising (if not superior) aspartyl protease inhibitors as their hydroxy-containing counterparts. In fact, the present invention shows that certain amino-containing inventive compounds possess several superior biological properties over their hydroxy-containing counterparts (e.g., increased potency in cells, increased selectivity for the BACE enzyme, and/or superior ADME properties).

Thus, the present invention provides novel amino-containing compounds capable of inhibiting the activity of BACE. More generally, the compounds of the invention are inhibitors of proteases, and more specifically inhibitors of aspartyl proteases. In certain embodiments of special interest, the inventive compounds are useful for the treatment or prevention of disorders characterized by β amyloid deposits or plaques. In certain exemplary embodiments, the compounds are useful for the treatment of Alzheimer's Disease.

Compounds of this invention include those generally set forth above and described specifically herein, and are illustrated in part by the various classes, subgenera and species disclosed herein.

Additionally, the present invention provides pharmaceutically acceptable derivatives of the inventive compounds, and methods of treating a subject using these compounds, pharmaceutical compositions thereof, or either of these in combination with one or more additional therapeutic agents.

1) General Description of Compounds of the Invention

In certain embodiments, the compounds of the invention include compounds of the general formula (I) as further defined below:

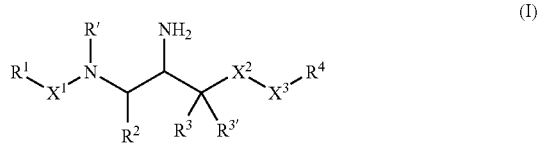

(I)

and pharmaceutically acceptable derivatives thereof;
wherein R' is hydrogen or an aliphatic, heteroaliphatic, aromatic or heteroaromatic moiety, or R', taken together with $R^2$ or a substituent present on $R^1$, may form a cycloheteroaliphatic moiety;
$R^1$ is an aliphatic, heteroaliphatic, aromatic or heteroaromatic moiety, or $R^1$, taken together with R', may form a cycloheteroaliphatic moiety;
$X^1$ is —C(=O)—, —S(=O)—, —C(=NH)—, —C(=S)—, —NC(=O)—, —NC(=S)—, —N—C(=N—C≡N)—, —NS(O$_2$)—, —CHR$^{X1A}$—, —SO$_2$—, —COO—, —C(=O)C(R$^{X1A}$)$_2$—, or —SC(=O)— wherein each occurrence of R$^{X1A}$ is independently hydrogen, or an aliphatic, heteroaliphatic, aromatic or heteroaromatic moiety;
$R^2$ is an aliphatic, heteroaliphatic, aromatic or heteroaromatic moiety, or $R^2$, taken together with R', may form a cycloheteroaliphatic moiety;
$R^3$ is hydrogen, halogen, or an aliphatic, heteroaliphatic, aromatic or heteroaromatic moiety;
$R^{3'}$ is hydrogen, halogen, or lower alkyl;
$R^4$ is hydrogen, an aliphatic, heteroaliphatic, aromatic or heteroaromatic moiety, or $R^4$, taken together with a substituent present on $X^2$ or $X^3$, may form a cycloaliphatic, cycloheteroaliphatic, aromatic, or heteroaromatic moiety;

$X^2$ is absent, —NR$^{X2A}$—, —(CHR$^{X2A}$)$_j$—, —NR$^{X2A}$Y—, —(CHR$^{X2A}$)$_j$Y— or —N(R$^{X2A}$)CH(R$^{X2A'}$)Y— wherein each occurrence of R$^{X2A}$ is independently hydrogen or an aliphatic, heteroaliphatic, aromatic or heteroaromatic moiety; each occurrence of Y is independently

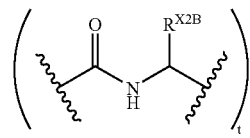

wherein, for each independent occurrence of t, R$^{X2B}$ is hydrogen, or an aliphatic, heteroaliphatic, aromatic or heteroaromatic moiety, or R$^{X2A}$ or one occurrence of R$^{X2B}$ taken together with $R^4$ may form a cycloaliphatic, cycloheteroaliphatic, aromatic or heteroaromatic moiety, and wherein each occurrence of j and t is independently an integer from 1 to 4; and
$X^3$ is absent, —NHCO—, —NHSO$_2$—, —NHCONH—, —NHCOO—, —CH$_2$NH—, —C(=O)—, —S(=O)—, —C(=NH)—, —C(=S)—, —NC(=S)N—, —N—C(=N—C≡N)N—, —NS(O$_2$)N—, —SO$_2$—, —C(=O)NR$^{X3A}$—, —C(=S)NR$^{X3A}$—, —COO—, —(CHR$^{X3A}$)$_k$—, —O—, —CH$_2$NR$^{X3A}$—, or —NR$^{X3A}$—, wherein each occurrence of R$^{X3A}$ is independently hydrogen, an aliphatic, heteroaliphatic, aromatic or heteroaromatic moiety, or R$^{X3A}$ taken together with $R^4$ may form a cycloaliphatic, cycloheteroaliphatic, aromatic or heteroaromatic moiety, and k is an integer from 1 to 3.

In certain embodiments of compounds described directly above and compounds as described in certain classes and subclasses herein, one or more of the following groups do not occur simultaneously as defined:
(i) R', $R^3$ and $R^{3'}$ are each hydrogen; $R^2$ is alkyl, cycloalkylalkyl or aralkyl; —X$^2$—X$^3$—R$^4$ together represents —CHR$^e$C(=O)NHCH(R$^w$)C(=O)NR$^x$R$^y$, wherein R$^e$ is hydrogen or alkyl, R$^w$ is alkyl, and one of R$^x$ or R$^y$ represents hydrogen and the other represents hydrogen, alkyl, aryl, aralkyl, 1-alkoxycarbonyl-2-phenylethyl, 1-alkoxycarbonyl-2-(imidazol-4-yl)ethyl, 2-(imidazol-1-yl)ethyl, indanyl, heterocyclyl-alkyl, carboxyalkyl, alkoxycarbonylalkyl, aryloxycarbonylalkyl, aralkoxycarbonylalkyl or a group of the formula -A-N(R$^a$)(R$^b$) in which A represents alkylene and R$^a$ and R$^b$ each represents alkyl or R$^a$ and R$^b$ together represent a pentamethylene group in which one methylene group can be replaced by NH, N-alkyl, N-alkanoyl, N-aralkoxycarbonyl, O, S, SO, or SO$_2$; or R$^x$ and R$^y$ together with the nitrogen atom to which they are attached represent a 1,2,3,4-tetrahydroisoquinoline ring; and —X$^1$—R$^1$ together represents an alkoxycarbonyl, aralkoxycarbonyl, alkanoyl, aralkanoyl, aroyl, cycloalkylcarbonyl, heterocyclylcarbonyl, heterocyclyl-alkanoyl, 6-(dibenzylcarbamoyl)-4-oxohexanoyl moiety or an acyl group of an α-amino acid in which the amino group is substituted by an alkoxycarbonyl, aralkoxycarbonyl, diaralkylcarbamoyl, diaralkylalkanoyl, or aralkanoyl moiety;
wherein the term "aroyl" refers to an acyl group derived from from an arylcarboxylic acid such as benzoyl, 1-naphthoyl, 2-naphthoyl, etc., and the term "aralkanoyl" refers to an acyl group derived from an aryl-substituted alkanecarboxylic acid;
whereby the term "aryl" alone or in each of the aralkyl, aryloxycarbonylalkyl, aralkoxycarbonylalkyl or N-aralkoxycarbonyl moieties refers to a phenyl or naphthyl group optionally substituted with one or emore substituents selected from alkyl, hydroxy, alkoxy and halogen;

(ii) R', $R^3$ and $R^{3'}$ are each hydrogen; $X^1$ is —C(=O)—, —$SO_2$—, $N(R^x)SO_2$, $N(R^x)C(=O)$ or $SC(=O)$, wherein $R^x$ is hydrogen, $C_{1-5}$alkyl or joined together with $R^1$ either directly to form a 5–7 membered heterocycle such as pyrrolidinyl or piperidinyl, or through a heteroatom selected from N, O and S, to form a 6-membered heterocycle with the nitrogen to which they are attached such as morpholinyl, piperazyl, or N—$C_{1-3}$alkyl-piperazyl; $R^1$ is a substituted or unsubstituted $C_{1-6}$alkyl, a 5–6 membered heterocycle or a 6–10 carbon atoms aryl moiety substituted with $C_{1-4}$alkyl, $C_{1-3}$alkoxy, hydroxy, halogen, $N(R^a)_2$, C(=O)$OR^a$, —C(=O)$N(R^a)_2$, —$SO_2N(R^a)_2$, $CH_2N(R^a)_2$, $N(R^a)C(=O)R^a$ or $N(R^a)SO_2R^a$; $R^2$ is $OR^a$, $N(R^a)_2$, $C_{1-4}$alkenyl-$R^c$ or —$[CR^bR^c]_nR^c$; and —$X^2$—$X^3$—$R^4$ together represent —$CH(R^d)C(=O)NHCH(R^e)C(=O)$—Y—$[CR^fR^g]_mR^g$, wherein m is an integer from 0 to 5, Y is O or NH, $R^d$ and $R^e$ are independently hydrogen, $OR^a$, $N(R^a)_2$, $C_{1-4}$alkenyl-$R^c$ or —$[CR^bR^c]_nR^c$ wherein n is an integer from 0 to 5, $R^a$ is hydrogen or $C_{1-4}$alkyl, $R^b$ is hydrogen, hydroxy or $C_{1-4}$alkyl and $R^c$ is hydrogen, substituted or unsubstituted aryl, 5- or 6-membered heterocycle, $C_{1-6}$alkyl or $C_{1-6}$alkenyl, $C_{3-7}$cycloalkyl, 5- to 7-membered carbocyclic or 7- to 10-membered bicyclic carbocyclic ring, benzofuryl, indolyl, azabicyclo $C_{7-11}$cycloalkyl or benzopiperidinyl; $R^f$ is hydrogen, substituted or unsubstituted $C_{1-6}$alkyl or $(CH_2CH_2O)_pCH_3$ or $(CH_2CH_2O)_pH$ wherein p is an integer from 0 to 5, and $R^g$ is hydrogen, or substituted or unsubstituted aryl, heterocycle, 5- to 7-membered carbocyclic or 7- to 10-membered bicyclic carbocyclic ring;

(iii) R', $R^3$ and $R^{3'}$ are each hydrogen; $X^1$ is —C(=O)—, —$SO_2$—, $N(R^x)SO_2$, $N(R^x)C(=O)$ or $SC(=O)$, wherein $R^x$ is hydrogen, $C_{1-5}$alkyl or joined together with $R^1$ either directly to form a 5–7 membered heterocycle such as pyrrolidinyl or piperidinyl, or through a heteroatom selected from N, O and S, to form a 6-membered heterocycle with the nitrogen to which they are attached such as morpholinyl, piperazyl, or N—$C_{1-3}$alkyl-piperazyl; $R^1$ is a substituted or unsubstituted $C_{1-6}$alkyl, a 5–6 membered heterocycle or a 6–10 carbon atoms aryl moiety substituted with $C_{1-4}$alkyl, $C_{1-3}$alkoxy, hydroxy, halogen, $N(R^a)_2$, C(=O)$OR^a$, —C(=O)$N(R^a)_2$, —$SO_2N(R^a)_2$, $CH_2N(R^a)_2$, $N(R^a)C(=O)R^a$ or $N(R^a)SO_2R^a$; $R^2$ is $OR^a$, $N(R^a)_2$, $C_{1-4}$alkenyl-$R^c$ or —$[CR^bR^c]_nR^c$; and —$X^2$—$X^3$—$R^4$ together represent —$CH(R^d)C(=O)$—Y—$[CR^fR^g]_mR^g$, wherein m is an integer from 0 to 5, Y is O or NH, $R^d$ is hydrogen, $OR^a$, $N(R^a)_2$, $C_{1-4}$alkenyl-$R^c$ or —$[CR^bR^c]_nR^c$; wherein n is an integer from 0 to 5, $R^a$ is hydrogen or $C_{1-4}$alkyl, $R^b$ is hydrogen, hydroxy or $C_{1-4}$alkyl and $R^c$ is hydrogen, substituted or unsubstituted aryl, 5- or 6-membered heterocycle, $C_{1-6}$alkyl or $C_{1-6}$alkenyl, $C_{3-7}$cycloalkyl, 5- to 7-membered carbocyclic or 7- to 10-membered bicyclic carbocyclic ring, benzofuryl, indolyl, azabicyclo $C_{7-11}$cycloalkyl or benzopiperidinyl; $R^f$ is hydrogen, substituted or unsubstituted $C_{1-6}$alkyl or $(CH_2CH_2O)_pCH_3$ or $(CH_2CH_2O)_pH$ wherein p is an integer from 0 to 5, and $R^g$ is hydrogen, or substituted or unsubstituted aryl, heterocycle, 5- to 7-membered carbocyclic or 7- to 10-membered bicyclic carbocyclic ring;

(iv) R' and $R^{3'}$ are each hydrogen; $X^1$ is —C(=O)—, —$SO_2$—, $N(R^x)SO_2$, $N(R^x)C(=O)$ or $SC(=O)$, wherein $R^x$ is hydrogen, $C_{1-5}$alkyl or joined together with $R^1$ either directly to form a 5–7 membered heterocycle such as pyrrolidinyl or piperidinyl, or through a heteroatom selected from N, O and S, to form a 6-membered heterocycle with the nitrogen to which they are attached such as morpholinyl, piperazyl, or N—$C_{1-3}$alkyl-piperazyl; $R^1$ is a substituted or unsubstituted $C_{1-6}$alkyl, a 5–6 membered heterocycle or a 6–10 carbon atoms aryl moiety substituted with $C_{1-4}$alkyl, $C_{1-3}$alkoxy, hydroxy, halogen, $N(R^a)_2$, C(=O)$OR^a$, —C(=O)$N(R^a)_2$, —$SO_2N(R^a)_2$, $CH_2N(R^a)_2$, $N(R^a)C(=O)R^a$ or $N(R^a)SO_2R^a$; $R^2$ is $OR^a$, $N(R^a)_2$, $C_{1-4}$alkenyl-$R^c$ or —$[CR^bR^c]_nR^c$; $R^3$ is hydrogen, $OR^a$, $N(R^a)_2$, $C_{1-4}$alkenyl-$R^c$ or —$[CR^bR^c]_nR^c$; and —$X^2$—$X^3$—$R^4$ together represent —$CH(R^d)C(=O)NHCH(R^e)C(=O)$—Y—$[CR^fR^g]_mR^g$, wherein m is an integer from 0 to 5, Y is O or NH, $R^d$ and $R^e$ are independently hydrogen, $OR^a$, $N(R^a)_2$, $C_{1-4}$alkenyl-$R^c$ or —$[CR^bR^c]_nR^c$ wherein n is an integer from 0 to 5, $R^a$ is hydrogen or $C_{1-4}$alkyl, $R^b$ is hydrogen, hydroxy or $C_{1-4}$alkyl and $R^c$ is hydrogen, substituted or unsubstituted aryl, 5- or 6-membered heterocycle, $C_{1-6}$alkyl or $C_{1-6}$alkenyl, $C_{3-7}$cycloalkyl, 5- to 7-membered carbocyclic or 7- to 10-membered bicyclic carbocyclic ring, benzofuryl, indolyl, azabicyclo $C_{7-11}$cycloalkyl or benzopiperidinyl; $R^f$ is hydrogen, substituted or unsubstituted $C_{1-6}$alkyl or $(CH_2CH_2O)_pCH_3$ or $(CH_2CH_2O)_pH$ wherein p is an integer from 0 to 5, and $R^g$ is hydrogen, or substituted or unsubstituted aryl, heterocycle, 5- to 7-membered carbocyclic or 7- to 10-membered bicyclic carbocyclic ring;

(v) R' and $R^{3'}$ are each hydrogen; $X^1$ is —C(=O)—, —$SO_2$—, $N(R^x)SO_2$, $N(R^x)C(=O)$ or $SC(=O)$, wherein $R^x$ is hydrogen, $C_{1-5}$alkyl or joined together with $R^1$ either directly to form a 5–7 membered heterocycle such as pyrrolidinyl or piperidinyl, or through a heteroatom selected from N, O and S, to form a 6-membered heterocycle with the nitrogen to which they are attached such as morpholinyl, piperazyl, or N—$C_{1-3}$alkyl-piperazyl; $R^1$ is a substituted or unsubstituted $C_{1-6}$alkyl, a 5–6 membered heterocycle or a 6–10 carbon atoms aryl moiety substituted with $C_{1-4}$alkyl, $C_{1-3}$alkoxy, hydroxy, halogen, $N(R^a)_2$, C(=O)$OR^a$, —C(=O)$N(R^a)_2$, —$SO_2N(R^a)_2$, $CH_2N(R^a)_2$, $N(R^a)C(=O)R^a$ or $N(R^a)SO_2R^a$; $R^2$ is $OR^a$, $N(R^a)_2$, $C_{1-4}$alkenyl-$R^c$ or —$[CR^bR^c]_nR^c$; $R^3$ is hydrogen, $OR^a$, $N(R^a)_2$, $C_{1-4}$alkenyl-$R^c$ or —$[CR^bR^c]_nR^c$; and —$X^2$—$X^3$—$R^4$ together represent —$CH(R^d)C(=O)$—Y—$[CR^fR^g]_mR^g$, wherein m is an integer from 0 to 5, Y is O or NH, $R^d$ is hydrogen, $OR^a$, $N(R^a)_2$, $C_{1-4}$alkenyl-$R^c$ or —$[CR^bR^c]_nR^c$; wherein n is an integer from 0 to 5, $R^a$ is hydrogen or $C_{1-4}$alkyl, $R^b$ is hydrogen, hydroxy or $C_{1-4}$alkyl and $R^c$ is hydrogen, substituted or unsubstituted aryl, 5- or 6-membered heterocycle, $C_{1-6}$alkyl or $C_{1-6}$alkenyl, $C_{3-7}$cycloalkyl, 5- to 7-membered carbocyclic or 7- to 10-membered bicyclic carbocyclic ring, benzofuryl, indolyl, azabicyclo $C_{7-11}$cycloalkyl or benzopiperidinyl; $R^f$ is hydrogen, substituted or unsubstituted $C_{1-6}$alkyl or $(CH_2CH_2O)_pCH_3$ or $(CH_2CH_2O)_pH$ wherein p is an integer from 0 to 5, and $R^g$ is hydrogen, or substituted or unsubstituted aryl, heterocycle, 5- to 7-membered carbocyclic or 7- to 10-membered bicyclic carbocyclic ring; and (vi) R', $R^3$ and $R^{3'}$ are each hydrogen; $R^2$ is $C_{1-6}$alkyl, $C_{2-6}$alkenyl, $C_{3-7}$cycloalkyl, aryl, heteroaryl, T-$C_{1-6}$alkyl, T-$C_{2-6}$alkenyl, wherein T is aryl, heteroaryl or $C_{3-7}$cycloalkyl; $R^1$—$X^1$ together represent W wherein W is $R^x$, $R^xCO$, $R^xOCO$, $R^xOCH(R^y)CO$, $R^xNHCH(R^y)CO$, $R^xSCH(R^y)CO$, $R^xSO_2$, $R^xSO$ or an amino acid with a blocked or unblocked amino terminus, wherein $R^x$ and $R^y$ are each independently hydrogen, $C_{1-6}$alkyl, $C_{3-7}$cycloalkyl, aryl, heteroaryl, T-$C_{1-6}$alkyl or T-$(CH_2)_nCH(T)$ $(CH_2)_n$ wherein n is an integer from 1 to 4; and $—X^2—X^3—R^4$ together represent $—CH(R^a)C(=X)CHR^bR^c$, wherein X is (OH,H) or O; $R^a$ is hydrogen, $C_{1-6}$alkyl, $C_{2-6}$alkenyl, $C_{3-7}$cycloalkyl, aryl, heteroaryl, T-$C_{1-6}$alkyl or T-$C_{2-6}$alkenyl; $R^b$ is hydrogen or OH; and $R^c$ is Y, $(CHR^w)_n$—Y or $=CR^z(CHR^w)_n$—Y, wherein Y is hydrogen, OH, —$NR^wR^q$, aryl, heteroaryl or CO-Z, n is an integer from 1 to 4, Z is OH, —$NR^wR^q$, $OR^w$ or an amino acid with a blocked or unblocked carboxy terminus, $R^q$ is H, $C_{1-6}$alkyl or aryl$C_{1-6}$alykl, and $R^z$ and $R^w$ are each independently hydrogen, $C_{1-6}$alkyl, $C_{3-7}$cycloalkyl, aryl, heteroaryl, T-$C_{1-6}$alkyl or T-$C_{2-6}$alkenyl. In certain embodiments, compounds specifically and/or generically disclosed in European Application No.: EP 0 316 965 (which is incorporated herein by reference) are excluded.

In certain embodiments, the present invention defines particular classes of compounds which are of special interest. For example, one class of compounds of special interest includes those compounds of formula (I) having the stereochemistry shown in Formula ($I^A$):

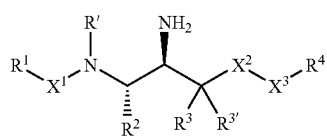

(I$^A$)

Another class of compounds of special interest includes those compounds of formula ($I^A$) wherein, $X^2$ is absent and the compound has the Formula ($I^B$):

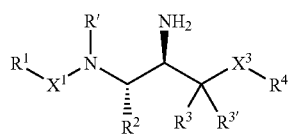

(I$^B$)

Another class of compounds of special interest includes those compounds of formula ($I^A$) wherein $X^3$ is absent and the compound has the Formula ($I^C$):

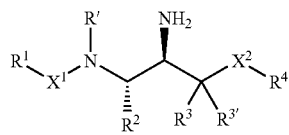

(I$^C$)

Another class of compounds of special interest includes those compounds of formula ($I^A$) wherein $X^2$ and $X^3$ are each absent and the compound has the Formula ($I^D$):

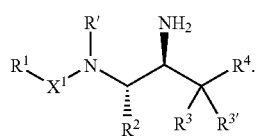

(I$^D$)

Another class of compounds of special interest includes those compounds of formula ($I^A$) wherein $R^{3'}$ is hydrogen, $X^2$ is CHMe and the compound has the Formula ($I^E$):

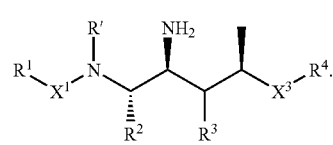

(I$^E$)

Another class of compounds of special interest includes those compounds of formula ($I^A$) wherein $R^{3'}$ is hydrogen, $X^3$ is absent, $X^2$ is —CH(Me)Y— where Y is

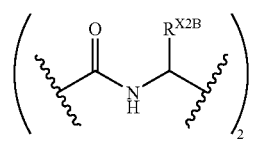

and the compound has the Formula ($I^F$):

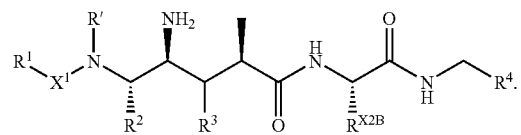

(I$^F$)

Another class of compounds of special interest includes those compounds of formula (I) wherein R' and $R^{3'}$ are each hydrogen, $X^2$ is CHMe and $X^3$ is —C(=O)NH—, and the compound has the Formula (II):

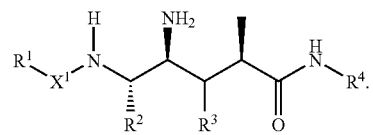

(II)

Another class of compounds of special interest includes those compounds of formula (I) wherein $X^1$ is —C(=O)—, R' is hydrogen, $X^2$ and $X^3$ are each absent, and the compound has the Formula (III):

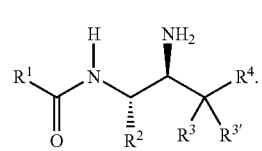

(III)

Another class of compounds of special interest includes those compounds of formula (I) wherein $X^1$ is —C(=O)—, R' and $R^{3'}$ are each hydrogen, $X^2$ is —CHMe, and the compound has the Formula (IV):

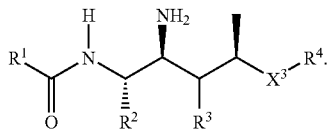

Another class of compounds of special interest includes those compounds of formula (I) wherein R' and R³' are each hydrogen, X² is —NR$^{X2A}$, and the compound has the Formula (V):

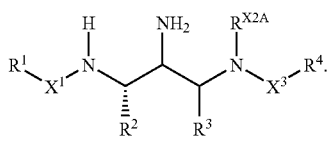

Another class of compounds of special interest includes those compounds of formula (V) above having the stereochemistry as shown in Formula (V$^A$):

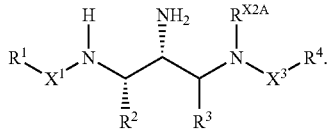

Another class of compounds of special interest includes those compounds of formula (I) wherein R' and R³' are each hydrogen, X¹ is —C(=O)—, X² is —NH—, and the compound has the Formula (VI):

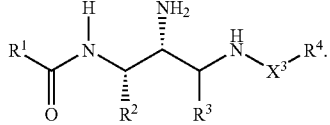

Another class of compounds of special interest includes those compounds of Formula (I) wherein X¹ is —C(=O)— and the compound has the structure as shown in Formula (VII):

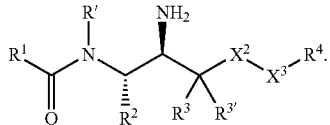

Another class of compounds of special interest includes those compounds of formula (I) wherein X¹ is CHR$^{X1A}$ and the compound has the structure as shown in Formula (VIII):

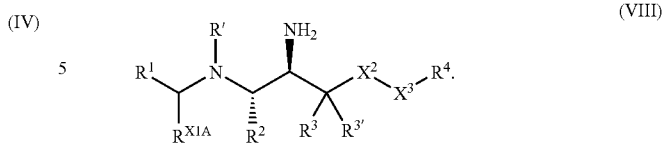

Another class of compounds of special interest includes those compounds of formula (I) wherein X¹ is CH₂, X² is CHR$^{X2A}$, X³ is —C(=O)NR$^{X3A}$, and the compound has the Formula (IX):

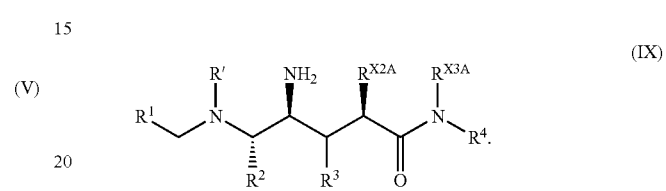

Another class of compounds of special interest includes those compounds of formula (IX) wherein R$^{X2A}$ is methyl and the compound has the Formula (IX$^A$):

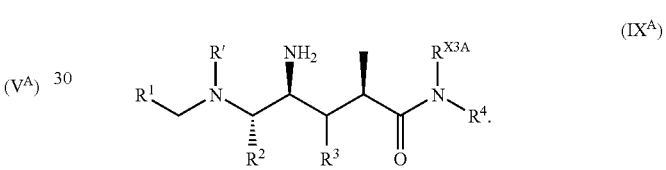

Another class of compounds of special interest includes those compounds of formula (I) wherein X¹ is —C(=O)—, X² is CHR$^{X2A}$, X³ is —CH₂NR$^{X3A}$, and the compound has the Formula (X):

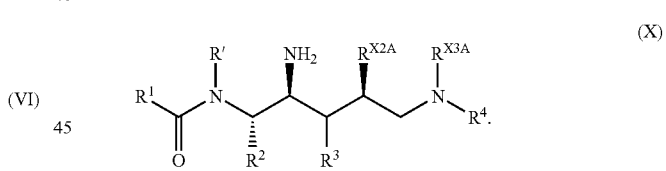

Another class of compounds of special interest includes those compounds of formula (X) wherein R$^{X2A}$ is methyl and the compound has the Formula (X$^A$):

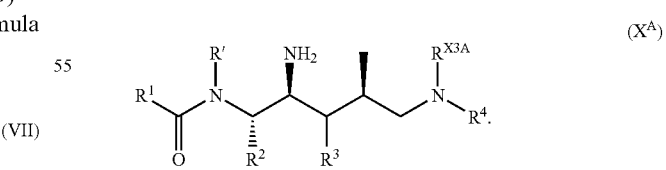

In certain other exemplary embodiments, for each of the classes of compounds as described above, R³ is hydrogen; R² is substituted or unsubstituted lower alkyl, lower alkylamino, lower heteroaryl, —(CH₂)cycloalkyl, —(CH₂)heterocycloalkyl, —(CH₂)aryl, —(CH₂)heteroaryl, optionally substituted with one or more occurrences of R$^{2A}$, wherein R$^{2A}$ is hydrogen, alkyl, heteroalkyl, aryl, heteroaryl, -(alkyl)

aryl, -(alkyl)heteroaryl, —OR$^{2B}$, —SR$^{2B}$, —N(R$^{2B}$)$_2$, —SO$_2$N(R$^{2B}$)$_2$, —C(=O)N(R$^{2B}$)$_2$, halogen, —CN, —NO$_2$, —C(=O)OR$^{2B}$, —N(R$^{2B}$)C(=O)R$^{2C}$, wherein each occcurrence of R$^{2B}$ and R$^{2C}$ is independently hydrogen, lower alkyl, lower heteroalkyl, aryl, heteroaryl, -(alkyl)aryl or -(alkyl)heteroaryl; R$^1$ is alkyl, alkenyl, heteroalkyl, heteroalkenyl, aryl, heteroaryl, -(alkyl)aryl, -(alkyl)heteroaryl, -(heteroalkyl)aryl, or -(heteroalkyl)heteroaryl, wherein R$^1$ is optionally substituted with one or more occurrences of R$^{1A}$, wherein R$^{1A}$ is hydrogen, alkyl, heteroalkyl, aryl, heteroaryl, -(alkyl)aryl, -(alkyl)heteroaryl, —OR$^{1B}$, —SR$^{1B}$, —N(R$^{1B}$)$_2$, —SO$_2$N(R$^{1B}$)$_2$, —C(=O)N(R$^{1B}$)$_2$, halogen, —CN, —NO$_2$, —C(=O)OR$^{1B}$, N(R$^{1B}$)C(=O)R$^{1C}$; or or R$^{1B}$ and R$^{1C}$, taken together with the atoms to which they are attached, form a substituted or unsubstituted heterocyclic moiety; wherein each occcurrence of R$^{1B}$ and R$^{1C}$ is independently hydrogen, lower alkyl, lower heteroalkyl, aryl, heteroaryl, -(alkyl)aryl or -(alkyl)heteroaryl; and R$^4$ is alkyl, alkenyl, heteroalkyl, heteroalkenyl, aryl, heteroaryl, -(alkyl) aryl, -(alkyl)heteroaryl -(heteroalkyl)aryl, or -(heteroalkyl) heteroaryl, optionally substituted with one or more occurrences of R$^{4A}$, wherein R$^{4A}$ is hydrogen, alkyl, heteroalkyl, aryl, heteroaryl, -(alkyl)aryl, -(alkyl)heteroaryl, —OR$^{4B}$, —SR$^{4B}$, N(R$^{4B}$)$_2$, —SO$_2$N(R$^{4B}$)$_2$, —C(=O)N(R$^{4B}$)$_2$, halogen, —CN, —NO$_2$, —C(=O)OR$^{4B}$, —N(R$^{4B}$)C(=O)R$^{4C}$, wherein each occcurrence of R$^{4B}$ and R$^{4C}$ is independently hydrogen, lower alkyl, lower heteroalkyl, aryl, heteroaryl, -(alkyl)aryl or -(alkyl)heteroaryl.

A number of important subclasses of each of the foregoing classes deserve separate mention; these subclasses include subclasses of the foregoing classes in which:

i) R$^1$ is substituted or unsubstituted, linear or branched, cyclic or acyclic alkyl or alkenyl;

ii) R$^1$ is substituted or unsubstituted aryl, heteroaryl, -(alkyl)aryl, -(alkyl)heteroaryl or heterocyclic;

iii) R$^1$ is one of:

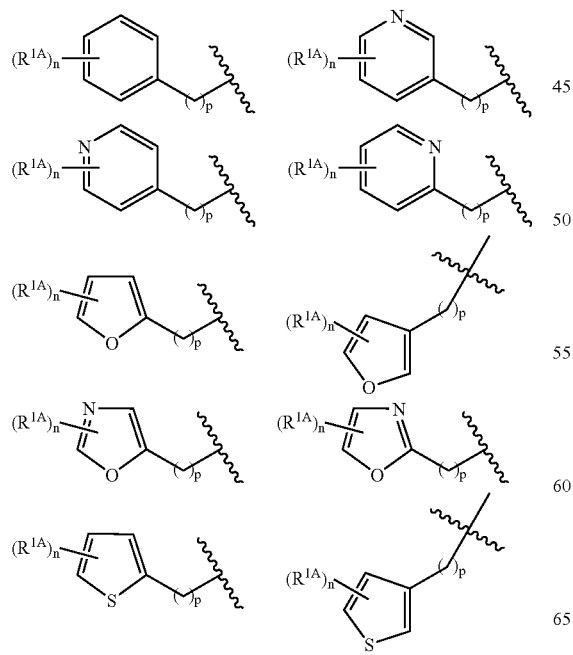

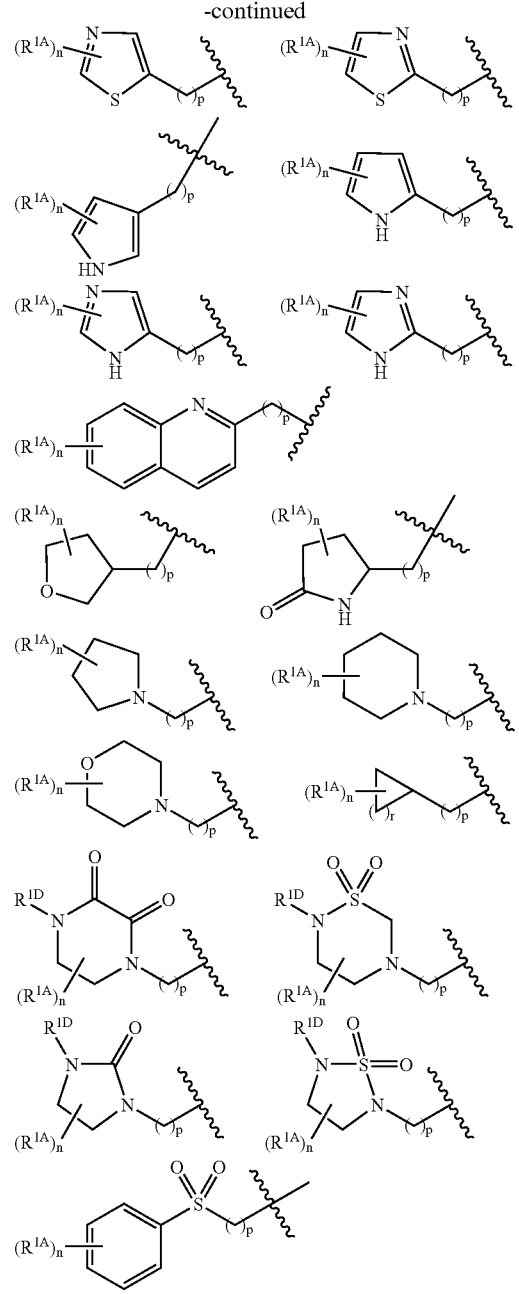

wherein R$^{1A}$ is hydrogen, alkyl, heteroalkyl, aryl, heteroaryl, -(alkyl)aryl, -(alkyl)heteroaryl, —OR$^{1B}$, —SR$^{1B}$, —N(R$^{1B}$)$_2$, —SO$_2$N(R$^{1B}$)$_2$, —C(=O)N(R$^{1B}$)$_2$, halogen, —CN, —NO$_2$, —C(=O)OR$^{1B}$, N(R$^{1B}$)C(=O)R$^{1C}$ or —N(R$^{1B}$)SO$_2$R$^{1C}$; wherein each occcurrence of R$^{1B}$ and R$^{1C}$ is independently hydrogen, lower alkyl, lower heteroalkyl, aryl, heteroaryl, -(alkyl)aryl, -(alkyl)heteroaryl; or R$^{1B}$ and R$^{1C}$, taken together with the atoms to which they are attached, form a substituted or unsubstituted heterocyclic moiety; R$^{1D}$ is hydrogen, alkyl, heteroalkyl, aryl, heteroaryl, -(alkyl)aryl, -(alkyl)heteroaryl, acyl or a nitrogen protecting group; wherein n and p are each independently integers from 0 to 3 and r is an integer from 1 to 6; whereby each of the foregoing alkyl and heteroalkyl moieties may be linear or branched, substituted or unsubstituted, cyclic or acylic, and each of the foregoing aryl, heteroaryl, -(alkyl)aryl and -(alkyl)heteroaryl moieties may be substituted or unsusbtituted;

iv) $R^1$ is one of:

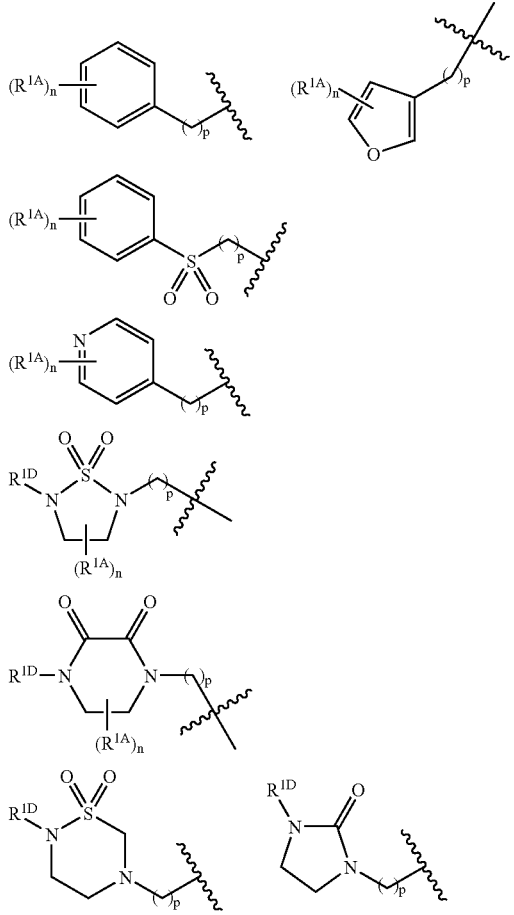

wherein n, p, $R^{1A}$ and $R^{1D}$ are as defined in iii) above;

v) $R^1$ is one of:

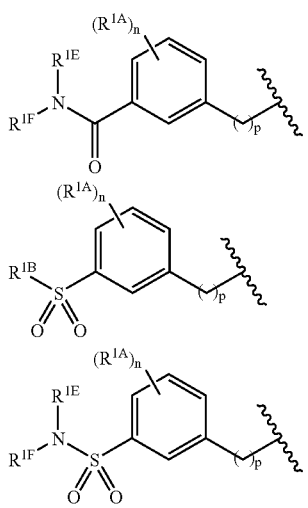

-continued

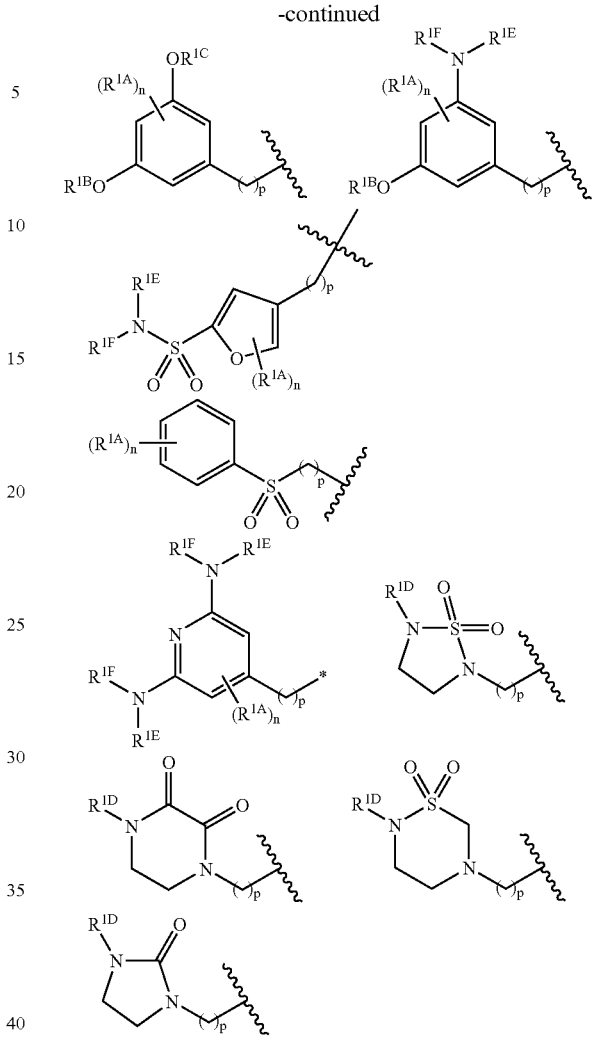

wherein n, p, $R^{1A}$ and $R^{1B}$ are as defined in iii) above; $R^{1D}$ is hydrogen, lower alkyl, lower heteroalkyl, aryl, heteroaryl, -(alkyl)aryl; -(alkyl)heteroaryl or acyl; $R^{1E}$ and $R^{1F}$ are each independently hydrogen, lower alkyl, lower heteroalkyl, aryl, heteroaryl, -(alkyl)aryl, -(alkyl)heteroaryl, —C(=O)$R^{1C}$ or —SO$_2$$R^{1C}$, where $R^{1C}$ is hydrogen, lower alkyl, lower heteroalkyl, aryl, heteroaryl, -(alkyl)aryl or -(alkyl)heteroaryl; or $R^{1E}$ and $R^{1F}$ taken together form a 5–8 membered heterocyclic ring; or $R^{1E}$ and one occurrence of $R^{1A}$, taken together, form a substituted or unsubstituted, saturated or unsaturated heterocyclic ring;

vi) $R^1$ is:

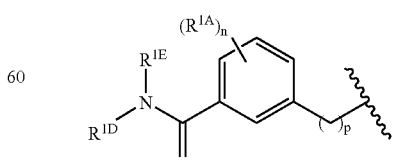

wherein n is 1–2; p is 0–1; $R^{1A}$ is hydrogen, alkyl, heteroalkyl, aryl, heteroaryl, -(alkyl)aryl or -(alkyl)heteroaryl, —OR$^{1B}$, —SR$^{1B}$, —N(R$^{1B}$)$_2$, —SO$_2$N(R$^{1B}$)$_2$, —C(=O)N(R$^{1B}$)$_2$, halogen, —CN, —NO$_2$, —C(=O)OR$^{1B}$, —N(R$^{1B}$)C(=O)R$^{1C}$ or —N(R$^{1B}$)SO$_2$R$^{1C}$, wherein each occcurrence of R$^{1B}$ and R$^{1C}$ is independently hydrogen, lower alkyl, lower heteroalkyl, aryl, heteroaryl, -(alkyl)aryl or -(alkyl)heteroaryl; or R$^{1B}$ and R$^{1C}$, taken together with the atoms to which they are attached, form a substituted or unsubstituted heterocyclic moiety; R$^{1D}$ and R$^{1E}$ are each independently hydrogen or lower alkyl; or R$^{1D}$ and R$^{1E}$ taken together form a 5–8 membered heterocyclic ring; or R$^{1E}$ and one occurrence of R$^{1A}$, taken together, form a substituted or unsubstituted, saturated or unsaturated heterocyclic ring;

vii) R$^1$ is:

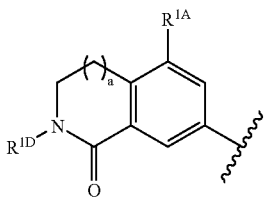

wherein a is 0 or 1; n is from 0–4; and R$^{1A}$ and R$^{1D}$ are as defined in vii) above;

viii) R$^1$ is:

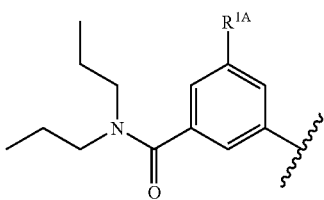

wherein R$^{1A}$ is hydrogen, halogen, —CN, —NO$_2$, lower alkyl, lower heteroalkyl, -(alkyl)aryl, -(alkyl)heteroaryl, —OR$^{1B}$ or —N(R$^{1B}$)SO$_2$R$^{1C}$; wherein each occcurrence of R$^{1B}$ and R$^{1C}$ is independently hydrogen, lower alkyl, lower heteroalkyl, aryl, heteroaryl, -(alkyl)aryl, -(alkyl)heteroaryl; whereby each of the foregoing alkyl and heteroalkyl moieties may be linear or branched, substituted or unsubstituted, cyclic or acylic, and each of the foregoing aryl, heteroaryl, -(alkyl)aryl and -(alkyl)heteroaryl moieties may be substituted or unsusbtituted;

ix) R$^1$ is:

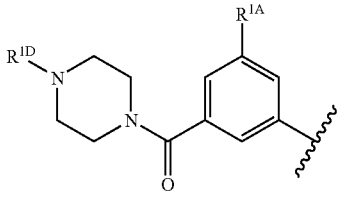

wherein R$^{1A}$ is as defined in viii) above; and R$^{1D}$ is hydrogen or lower alkyl;

x) R$^1$ is:

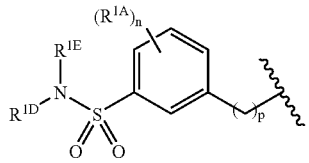

wherein n is 1–2; p is 0–1; R$^{1A}$ is hydrogen, alkyl, heteroalkyl, aryl, heteroaryl, -(alkyl)aryl or -(alkyl)heteroaryl, —OR$^{1B}$, —SR$^{1B}$, —N(R$^{1B}$)$_2$, —SO$_2$N(R$^{1B}$)$_2$, —C(=O)N(R$^{1B}$)$_2$, halogen, —CN, —NO$_2$, —C(=O)OR$^{1B}$, —N(R$^{1B}$)C(=O)R$^{1C}$ or —N(R$^{1B}$)SO$_2$R$^{1C}$, wherein each occcurrence of R$^{1B}$ and R$^{1C}$ is independently hydrogen, lower alkyl, lower heteroalkyl, aryl, heteroaryl, -(alkyl)aryl or -(alkyl)heteroaryl; or R$^{1B}$ and R$^{1C}$, taken together with the atoms to which they are attached, form a substituted or unsubstituted heterocyclic moiety; R$^{1D}$ and R$^{1E}$ are each independently hydrogen or lower alkyl; or R$^{1D}$ and R$^{1E}$ taken together form a 5–8 membered heterocyclic ring; or R$^{1E}$ and one occurrence of R$^{1A}$, taken together, form a substituted or unsubstituted, saturated or unsaturated heterocyclic ring;

xi) R$^1$ is:

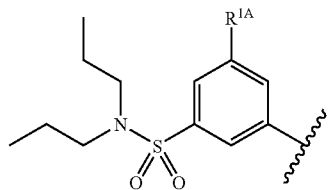

wherein R$^{1A}$ is hydrogen, halogen, —CN, —NO$_2$, lower alkyl, lower heteroalkyl, -(alkyl)aryl, -(alkyl)heteroaryl, —OR$^{1B}$ or —N(R$^{1B}$)SO$_2$R$^{1C}$; wherein each occcurrence of R$^{1B}$ and R$^{1C}$ is independently hydrogen, lower alkyl, lower heteroalkyl, aryl, heteroaryl, -(alkyl)aryl, -(alkyl)heteroaryl; whereby each of the foregoing alkyl and heteroalkyl moieties may be linear or branched, substituted or unsubstituted, cyclic or acylic, and each of the foregoing aryl, heteroaryl, -(alkyl)aryl and -(alkyl)heteroaryl moieties may be substituted or unsusbtituted;

xii) R$^1$ is:

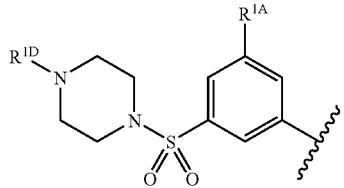

wherein R$^{1A}$ is as defined in x) above; and R$^{1D}$ is hydrogen or lower alkyl;

xiii) compounds of subsets vi)–xii) wherein R$^{1A}$ is methyl, methoxy or halide;

xiv) compounds of subsets vi)–xii) wherein R$^{1A}$ is methyl, methoxy or F;

xv) compounds of subsets vi)–xii) wherein R$^{1A}$ is methyl;

xvi) compounds of subsets viii) and xii) wherein R$^{1B}$ is hydrogen, methyl or ethyl;

xvii) $R^1$ is:

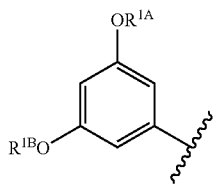

wherein $R^{1A}$ and $R^{1B}$ are each independently hydrogen, lower alkyl, lower heteroalkyl, aryl, heteroaryl, -(alkyl)aryl or -(alkyl)heteroaryl;

xviii) compounds of subset xvii) wherein $R^{1A}$ and $R^{1B}$ are each independently cyclic or acyclic lower alkyl;

xix) compounds of subset xvii) wherein $R^{1A}$ and $R^{1B}$ are each independently methyl, ethyl, propyl, butyl, pentyl, isopropyl, isobutyl, sec-butyl, isopentyl or cyclopropyl;

xx) $R^1$ is:

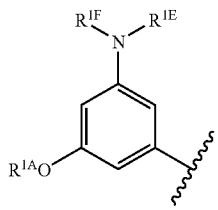

wherein $R^{1A}$ is hydrogen, lower alkyl, lower heteroalkyl, aryl, heteroaryl, -(alkyl)aryl or -(alkyl)heteroaryl; $R^{1E}$ and $R^{1F}$ are each independently hydrogen, lower alkyl, lower heteroalkyl, aryl, heteroaryl, -(alkyl)aryl, -(alkyl)heteroaryl, —C(=O)$R^{1C}$ or —SO$_2$$R^{1C}$, where $R^{1C}$ is hydrogen, lower alkyl, lower heteroalkyl, aryl, heteroaryl, -(alkyl)aryl or -(alkyl)heteroaryl; or $R^{1E}$ and $R^{1F}$ taken together form a 5–8 membered heterocyclic ring;

xxi) compounds of subset xx) wherein $R^{1A}$ is substituted or unsubstituted, linear or branched, cyclic or acyclic lower alkyl; $R^{1E}$ is lower alkyl; and $R^{1F}$ is —SO$_2$$R^{1D}$ wherein $R^{1D}$ is lower alkyl;

xxii) compounds of subset xx) wherein $R^{1A}$ is substituted or unsubstituted, linear or branched, cyclic or acyclic lower alkyl; $R^{1E}$ and $R^{1F}$, taken together with the nitrogen atom to which they are attached, form a 5- or 6-membered cyclic sulfonamide moiety;

xxiii) $R^1$ is one of:

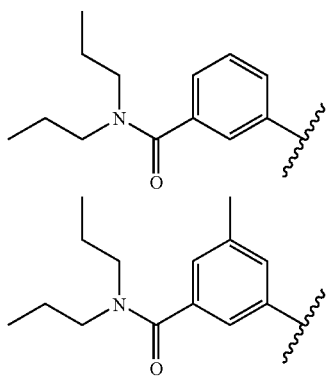

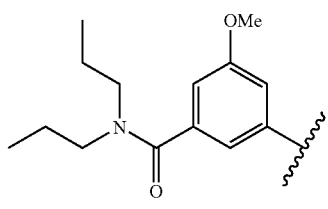

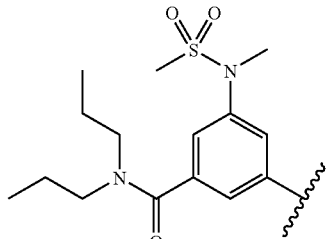

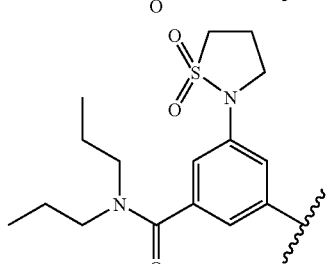

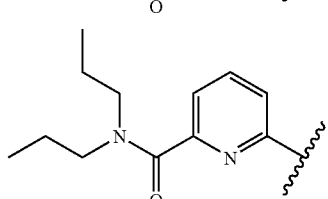

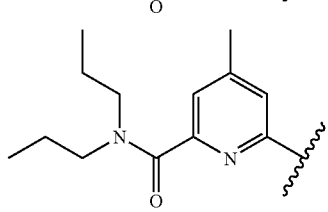

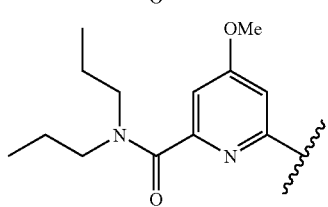

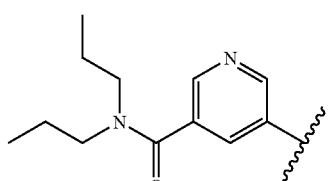

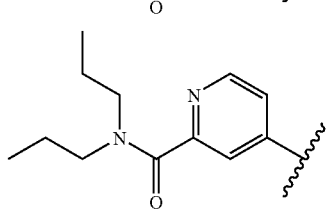

-continued
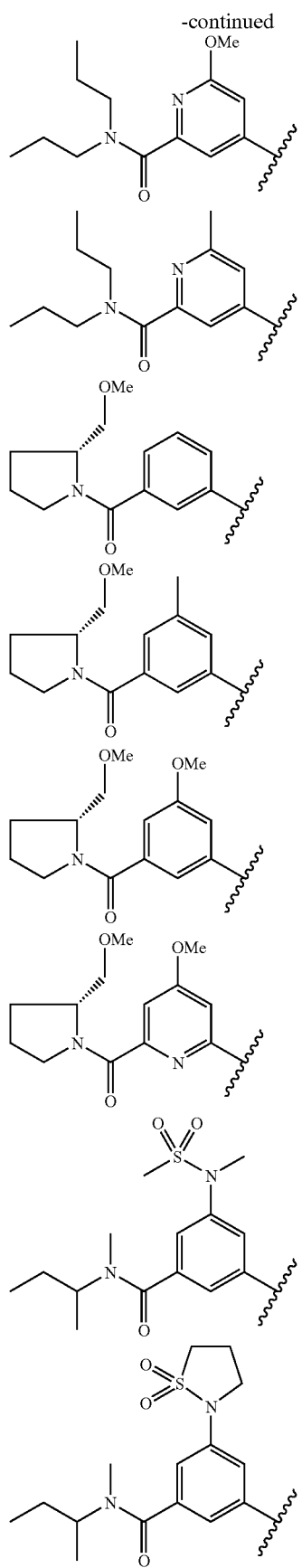
-continued
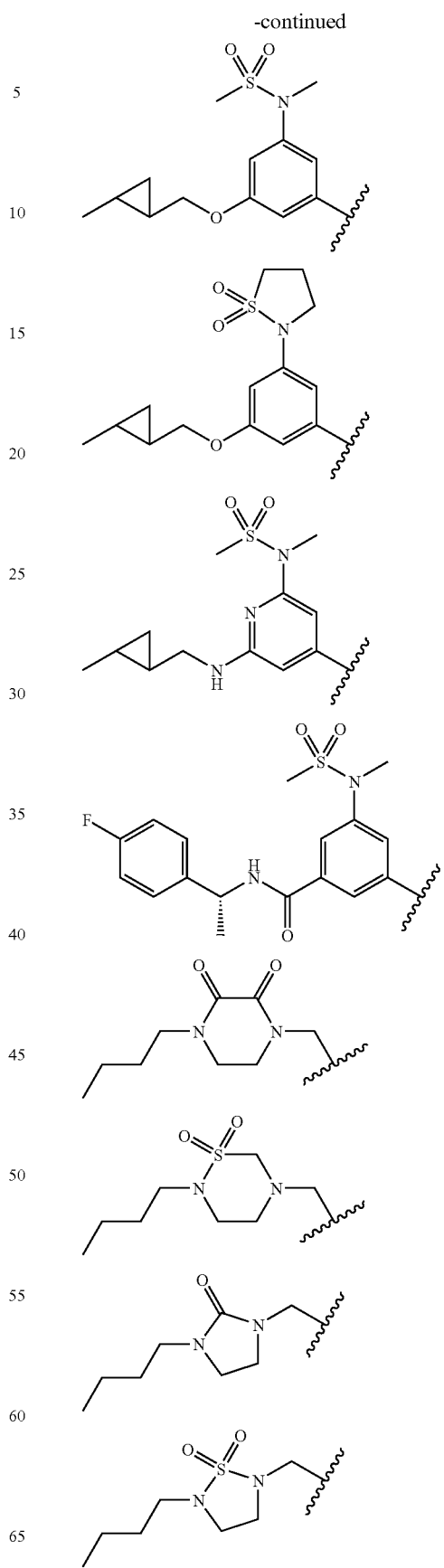

-continued
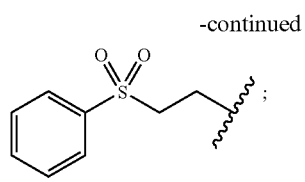
xxiv) R¹ is one of:
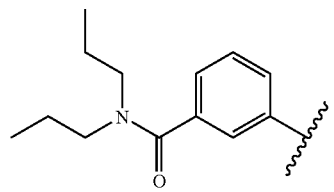
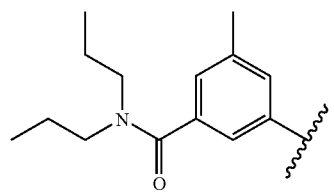
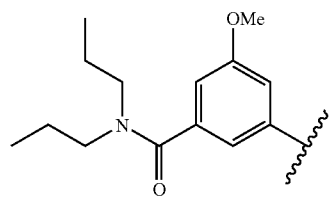
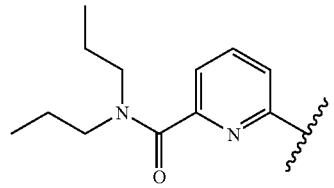
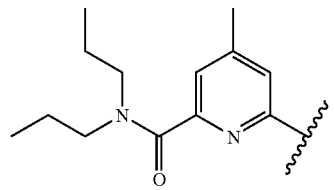
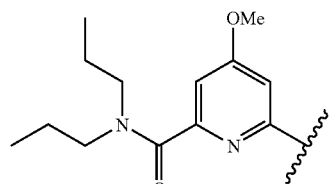
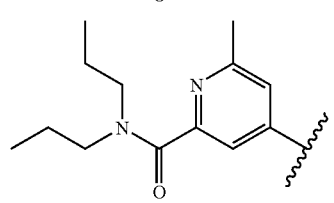
-continued
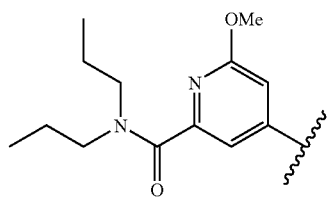
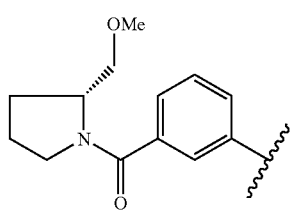
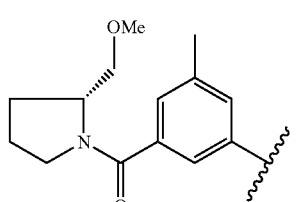
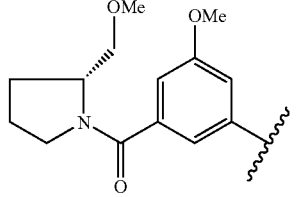
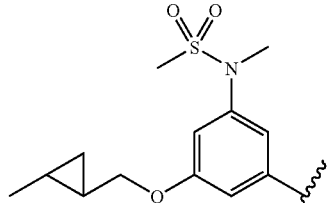
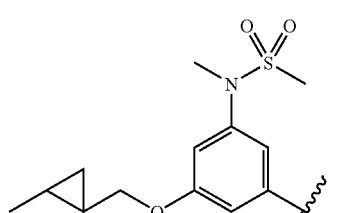
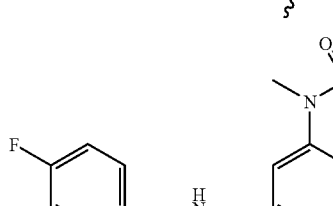

-continued

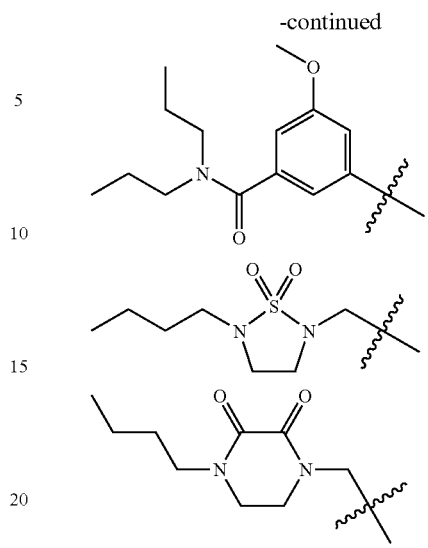

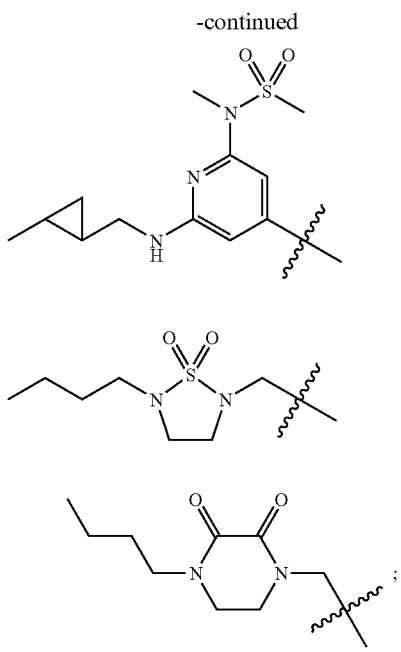

xxv) R¹ is one of:

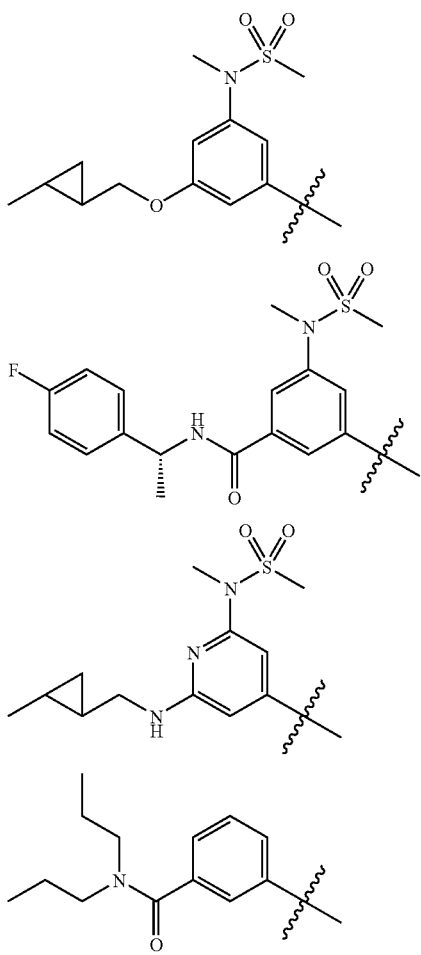

xxvi) R² is lower alkyl, —CH₂NR²ᴬR²ᴮ or —(CH₂) phenyl, wherein the phenyl group is optionally substituted with one or more occurrences of R²ᶜ, wherein R²ᶜ is hydrogen, alkyl, heteroalkyl, aryl, heteroaryl, -(alkyl)aryl or -(alkyl)heteroaryl, —OR²ᴰ, —SR², —N(R²ᴰ)₂, —SO₂N(R²ᴰ)₂, —C(=O)N(R²ᴰ)₂, halogen, —CN, —NO₂, —C(=O)OR²ᴰ, —N(R²ᴰ)C(=O)R²ᴱ, wherein each occcurrence of R²ᴰ and R²ᴱ is independently hydrogen, lower alkyl, lower heteroalkyl, aryl, heteroaryl, -(alkyl)aryl or -(alkyl)heteroaryl; and wherein R²ᴬ and R²ᴮ are each independently hydrogen, lower alkyl, lower heteroalkyl, aryl, heteroaryl, -(alkyl)aryl or -(alkyl)heteroaryl; whereby each of the foregoing alkyl and heteroalkyl moieties may be linear or branched, substituted or unsubstituted, cyclic or acylic, and each of the foregoing aryl, heteroaryl, -(alkyl)aryl and -(alkyl)heteroaryl moieties may be substituted or unsusbtituted;

xxvii) R² is lower alkyl, —CH₂NR²ᴬR²ᴮ or —(CH₂) phenyl, wherein the phenyl group is optionally substituted with one or more occurrences of R²ᶜ, wherein R²ᶜ is hydrogen, alkyl, alkoxy or halogen; and wherein R²ᴬ and R²ᴮ are each independently hydrogen, lower alkyl, lower heteroalkyl, aryl, heteroaryl, -(alkyl)aryl or -(alkyl)heteroaryl; whereby each of the foregoing alkyl and heteroalkyl moieties may be linear or branched, substituted or unsubstituted, cyclic or acylic, and each of the foregoing aryl, heteroaryl, -(alkyl)aryl and -(alkyl)heteroaryl moieties may be substituted or unsusbtituted;

xxviii) R² is one of:

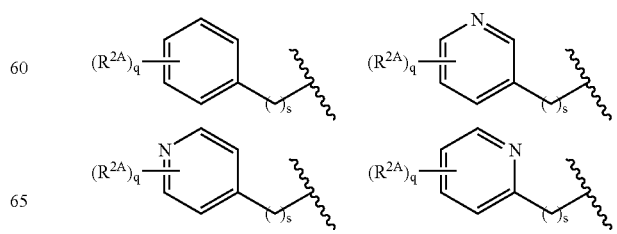

-continued

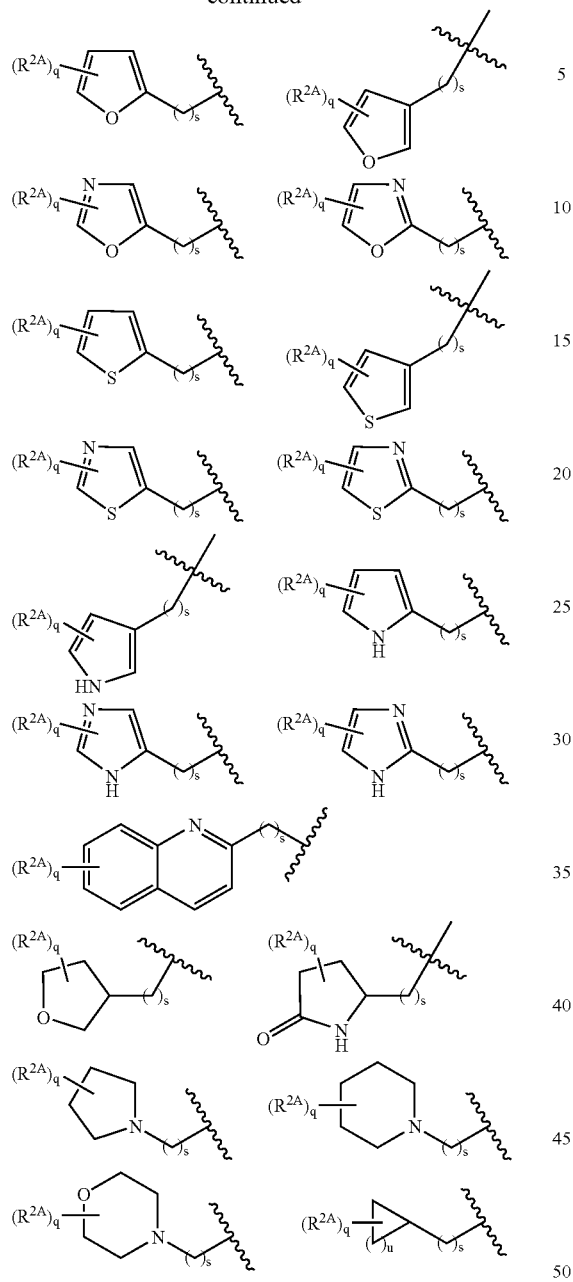

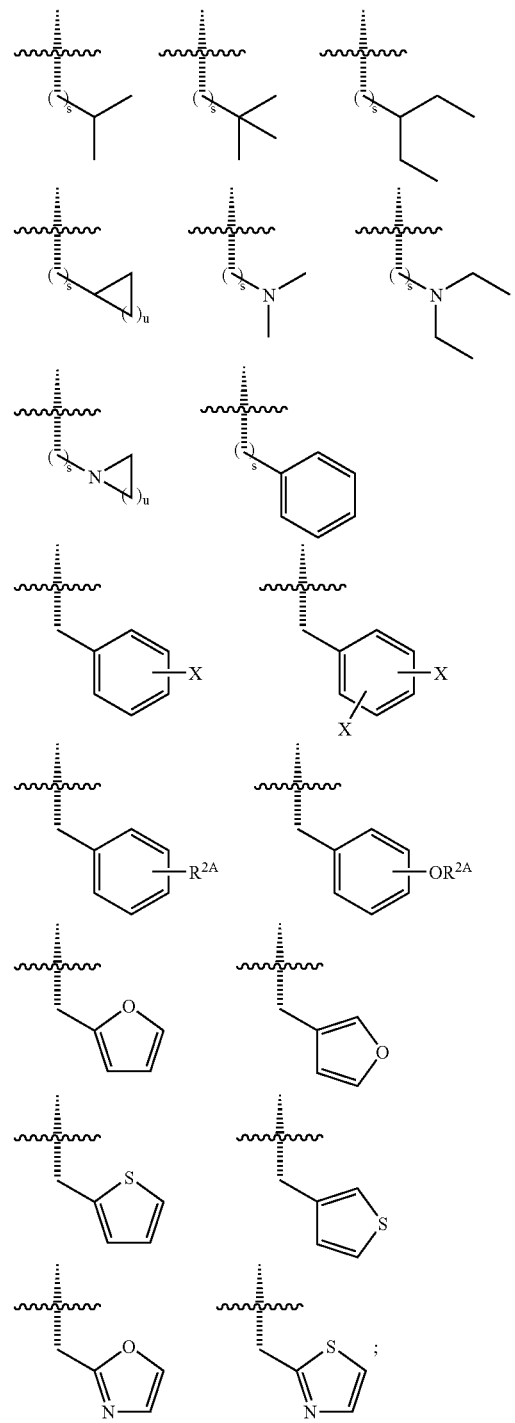

wherein $R^{2A}$ is hydrogen, alkyl, heteroalkyl, aryl, heteroaryl, -(alkyl)aryl or -(alkyl)heteroaryl, $-OR^{2B}$, $-SR^{2B}$, $-N(R^{2B})_2$, $-SO_2N(R^{2B})_2$, $-C(=O)N(R^{2B})_2$, halogen, $-CN$, $-NO_2$, $-C(=O)OR^{2B}$, $-N(R^{2B})C(=O)R^{2C}$, wherein each occcurrence of $R^{2B}$ and $R^{2C}$ is independently hydrogen, lower alkyl, lower heteroalkyl, aryl, heteroaryl, -(alkyl)aryl or -(alkyl)heteroaryl, wherein q and s are each independently integers from 0 to 3 and u is an integer from 1 to 6; whereby each of the foregoing alkyl and heteroalkyl moieties may be linear or branched, substituted or unsubstituted, cyclic or acyclic, and each of the foregoing aryl, heteroaryl, -(alkyl)aryl and -(alkyl) heteroaryl moieties may be substituted or unsusbtituted;

xxix) $R^2$ is one of:

wherein each occcurrence of $R^{2A}$ is independently hydrogen or lower alkyl; each occurrence of X is independently a halogen; s is an integer from 0 to 3 and u is an integer from 1 to 6; whereby each of the foregoing alkyl moieties may be linear or branched, substituted or unsubstituted and cyclic or acyclic;

xxx) compounds of subset xxix) wherein X is chlorine or fluorine;

xxxi) compounds of subset xxix) wherein each occurrence of X is fluorine;

xxxii) compounds of subset xxix) wherein $R^{2A}$ is methyl;
xxxiii) $R^2$ is one of:
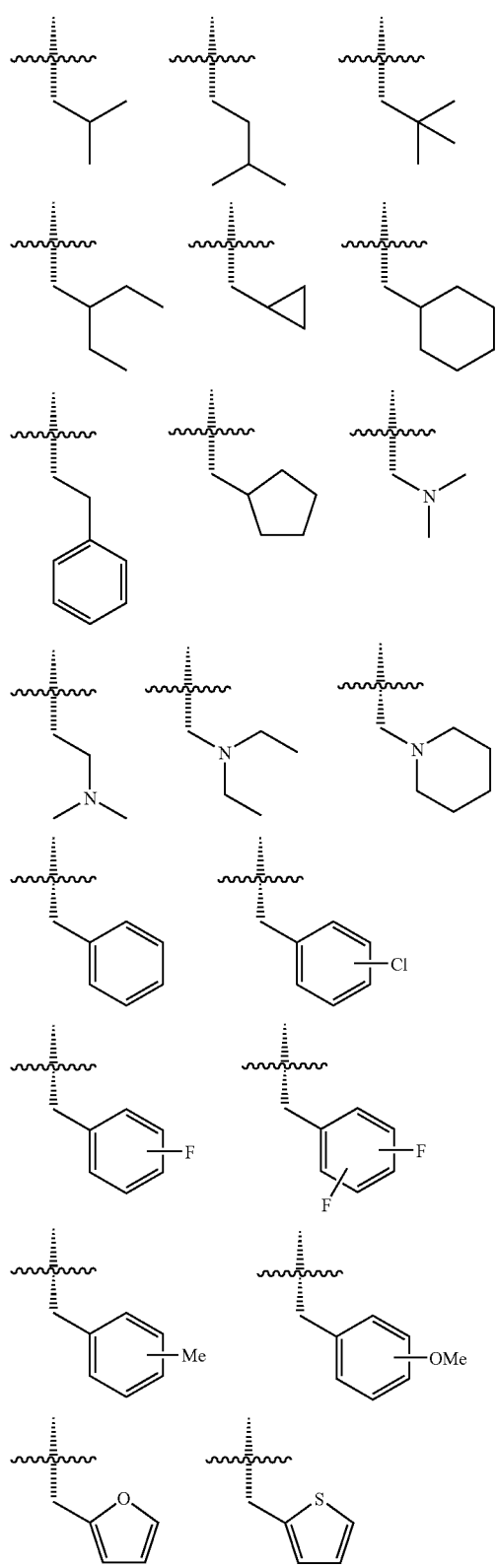
xxxiv) $R^2$ is one of:
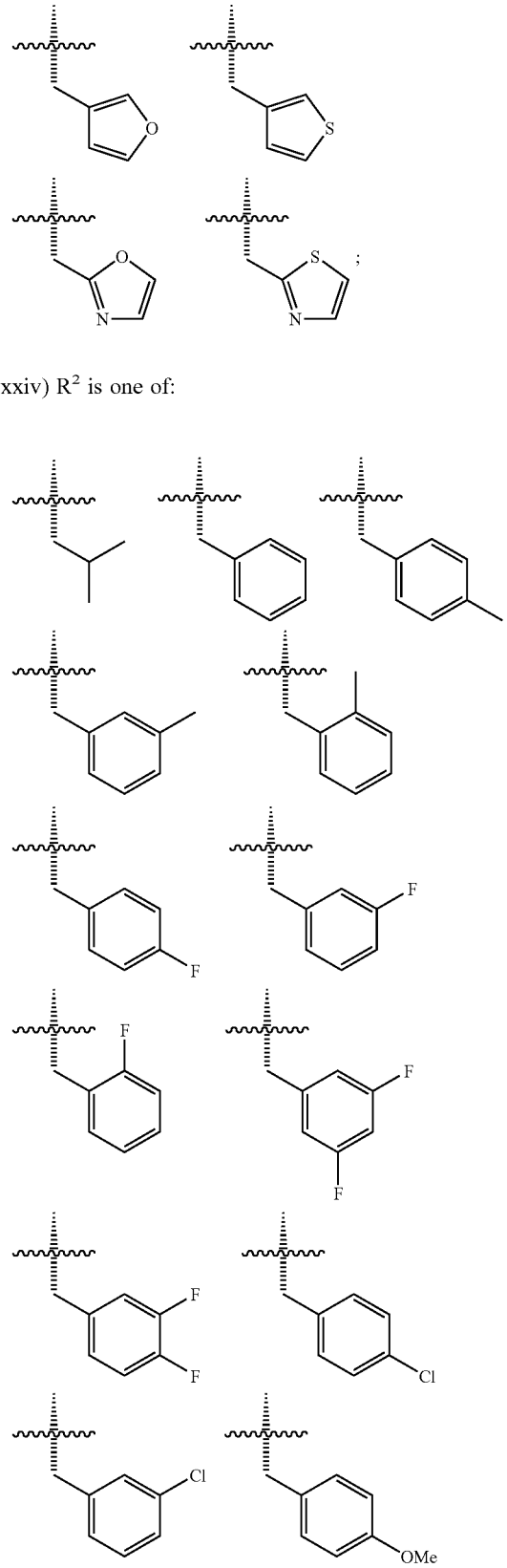

-continued

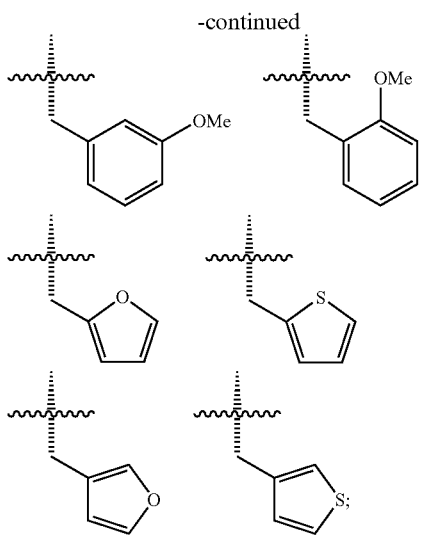

xxxv) R² is one of:

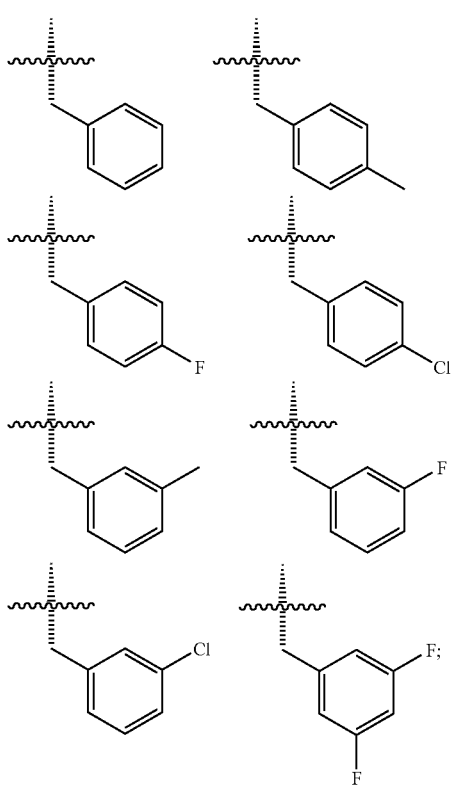

xxxvi) R² is one of:

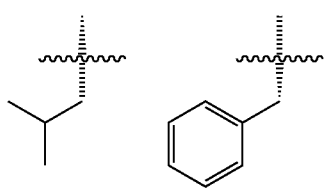

-continued

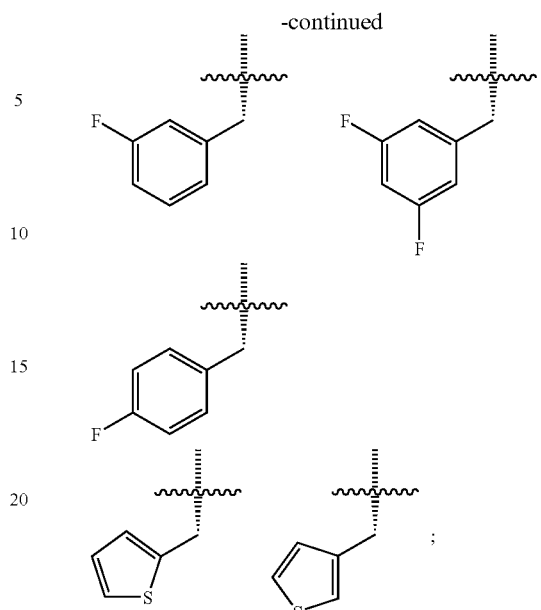

xxxvii) R³ is hydrogen or halogen;
xxxviii) R³ is hydrogen or F;
xxxix) R³ is hydrogen;
xl) R³' is hydrogen, methyl or halogen;
xli) R³' is hydrogen, methyl or F;
xlii) R³' is hydrogen;
xliii) one of R³ and R³' is halogen;
xliv) R³ and R³' are each independently hydrogen or F;
xlv) R³ and R³' are each F;
xlvi) R³ and R³' are each hydrogen;
xlvii) X¹ is —C(=O)—;
xlviii) X¹ is CHR$^{X1A}$ and R$^{X1A}$ is hydrogen or linear or branched substituted or unsubstituted alkyl;
xlix) X¹ is CH₂;
l) X² is CHR$^{X2A}$ and R$^{X2A}$ is hydrogen or linear or branched substituted or unsubstituted alkyl or -alkyl(aryl);
li) X² is CHR$^{X2A}$ and R$^{X2A}$ is methyl, ethyl, propyl, isopropyl, butyl, isobutyl, t-butyl, benzyl or phenethyl;
lii) X² is CHR$^{X2A}$ and R$^{X2A}$ is methyl, ethyl, propyl, isopropyl or phenethyl;
liii) X² is CHMe
liv) X² is —NR$^{X2A}$— and R$^{X2A}$ is hydrogen or linear or branched substituted or unsubstituted alkyl;
lv) X² is —NR$^{X2A}$— and R$^{X2A}$ is C1–C3 alkyl;
lvi) X² is NH;
lvii) X² is NHY where Y is

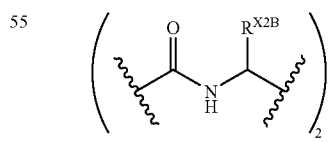

where each occurrence R$^{X2B}$ is independently hydrogen, or an aliphatic, heteroaliphatic, aryl, heteroaryl, -(alkyl)aryl, -(alkyl)heteroaryl, -(heteroalkyl)aryl, or -heteroalkyl)heteroaryl moiety; whereby each of the foregoing aliphatic and heteroaliphatic moieties may be linear or branched, substituted or unsubstituted, cyclic or acyclic, saturated or unsaturated, and each of the foregoing aryl, heteroaryl, -(alkyl)aryl and -(alkyl)heteroaryl moieties may be substituted or unsusbtituted;

lviii) $X^2$ is —CH(Me)Y— where Y is

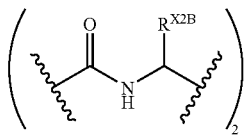

where each occurrence $R^{X2B}$ is hydrogen, or an aliphatic, heteroaliphatic, aryl, heteroaryl, -(alkyl)aryl, -(alkyl)heteroaryl, -(heteroalkyl)aryl, or -heteroalkyl)heteroaryl moiety; whereby each of the foregoing aliphatic and heteroaliphatic moieties may be linear or branched, substituted or unsubstituted, cyclic or acylic, saturated or unsaturated, and each of the foregoing aryl, heteroaryl, -(alkyl)aryl and -(alkyl)heteroaryl moieties may be substituted or unsusbtituted;

lix) $X^2$ is absent;

lx) $X^3$ is $(CHR^{X3A})_k$, —$CH_2NH$—, —$C(=O)NH$—, or —$SO_2$—, wherein each occurrence of $R^{X3A}$ is independently hydrogen, an aliphatic, heteroaliphatic, aryl, heteroaryl, -(alkyl)aryl, -(alkyl)heteroaryl, -(heteroalkyl)aryl, or -(heteroalkyl)heteroaryl moiety, and k is an integer from 1 to 3 and each of the foregoing aryl, heteroaryl, -(alkyl)aryl and -(alkyl)heteroaryl moieties may be substituted or unsusbtituted;

lxi) $X^3$ is absent;

lxii) $X^3$ is —C(=O)NH—;

lxiii) $X^3$ is $CHR^{X3A}$, $X^2$ is —$NR^{X2A}$— and $R^{X2A}$ and $R^{X3A}$ are each independently hydrogen or linear or branched substituted or unsubstituted alkyl;

lxiv) $X^3$ is $CHR^{X3A}$ and $X^2$ is NH; wherein $R^{X3A}$ is hydrogen or linear or branched substituted or unsubstituted alkyl;

lxv) $X^3$ is $CH_2$ and $X^2$ is NH;

lxvi) $X^2$ and $X^3$ are each absent;

lxvii) $X^2$ is $CHR^{X2A}$ and $X^3$ is $CH_2NH$; wherein $R^{X2A}$ is hydrogen or linear or branched substituted or unsubstituted alkyl;

lxviii) $X^2$ is $CHR^{X2A}$ and $X^3$ is —C(=O)NH—; wherein $R^{X2A}$ is hydrogen or linear or branched substituted or unsubstituted alkyl or -alkyl(aryl);

lxix) $R^4$ is substituted or unsubstituted, linear or branched, cyclic or acyclic alkyl, phenyl or —$(CH_2)$phenyl, wherein the phenyl group is optionally substituted with one or more occurrences of $R^{4A}$, wherein $R^{4A}$ is hydrogen, alkyl, heteroalkyl, aryl, heteroaryl, -(alkyl)aryl or -(alkyl)heteroaryl, —$OR^{4B}$, —$SR^{4B}$, —$N(R^{4B})_2$, —$SO_2N(R^{4B})_2$, —$C(=O)N(R^{4B})_2$, halogen, —CN, —$NO_2$, —$C(=O)OR^{4B}$, —$N(R^{4B})C(=O)R^{4C}$ or —$N(R^{4B})SO_2R^{4C}$; wherein each occcurrence of $R^{4B}$ and $R^{4C}$ is independently hydrogen, lower alkyl, lower heteroalkyl, aryl, heteroaryl, -(alkyl)aryl or -(alkyl)heteroaryl;

lxx) $R^4$ is substituted or unsubstituted, linear or branched, cyclic or acyclic alkyl, phenyl or —$(CH_2)$phenyl, wherein the phenyl group is optionally substituted with one or more occurrences of $R^{4A}$, wherein $R^{4A}$ is hydrogen, hydroxyl, alkyl, alkoxy or halogen;

lxxi) $R^4$ is one of:

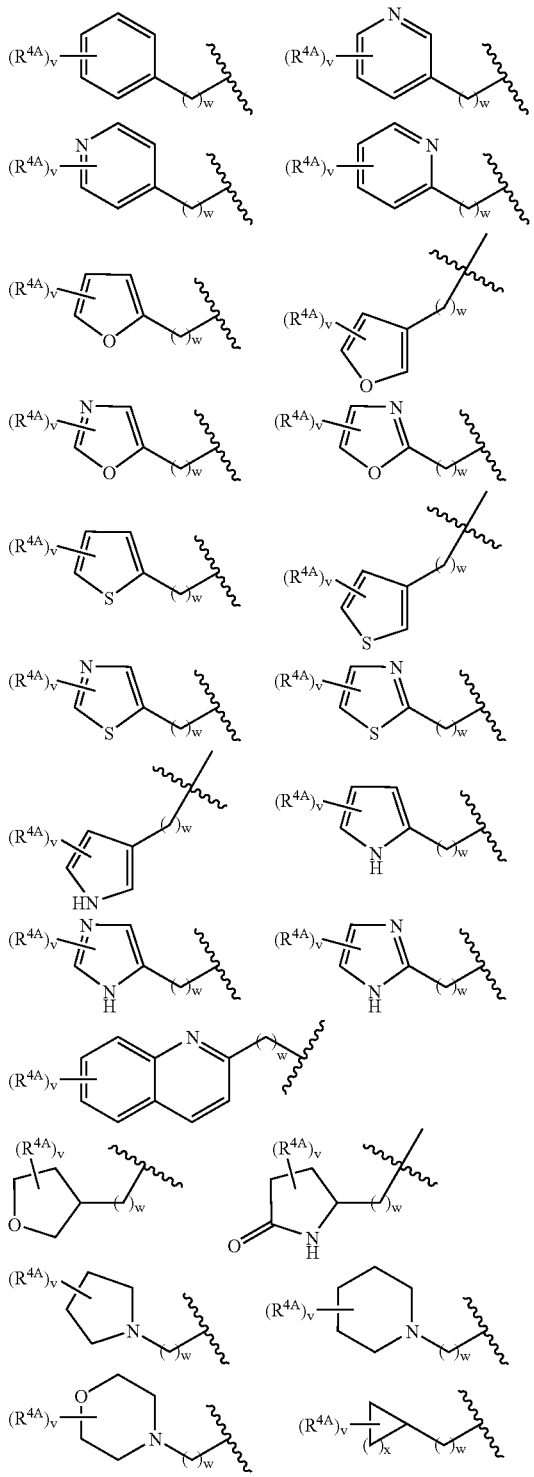

wherein each occurrence of $R^{4A}$ is independently hydrogen, alkyl, heteroalkyl, aryl, heteroaryl, -(alkyl)aryl or -(alkyl)heteroaryl, —$OR^{4B}$, —$SR^{4B}$, —$N(R^{4B})_2$, —$SO_2N(R^{4B})_2$, —$C(=O)N(R^{4B})_2$, halogen, —CN, —$NO_2$, —$C(=O)$ $OR^{4B}$, —$N(R^{4B})C(=O)R^{4C}$, wherein each occcurrence of $R^{4B}$ and $R^{4C}$ is independently hydrogen, lower alkyl, lower heteroalkyl, aryl, heteroaryl, -(alkyl)aryl or -(alkyl)

heteroaryl, wherein v and w are each independently integers from 0 to 3 and x is an integer from 1 to 6; whereby each of the foregoing alkyl and heteroalkyl moieties may be linear or branched, substituted or unsubstituted, cyclic or acyclic, and each of the foregoing aryl, heteroaryl, -(alkyl)aryl and -(alkyl)heteroaryl moieties may be substituted or unsusbtituted;

lxxii) $R^4$ is hydrogen;

lxxiii) $R^4$ is methyl, ethyl, propyl or one of:

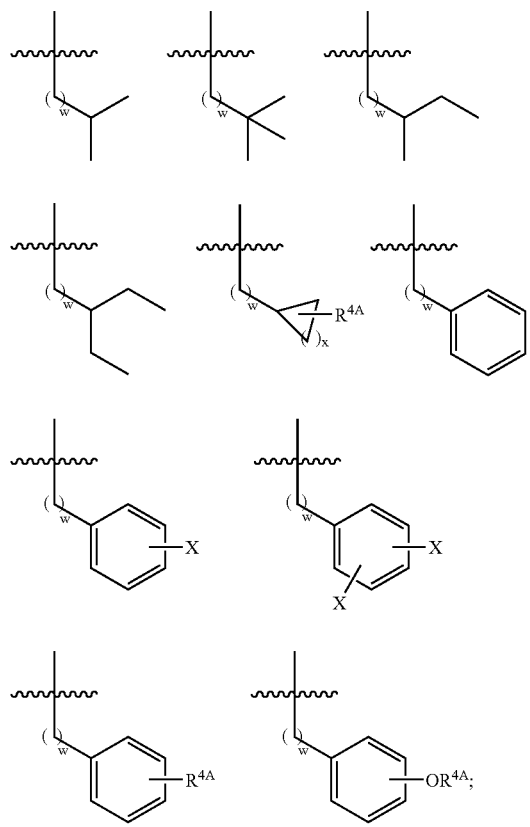

wherein each occcurrence of $R^{4A}$ is independently hydrogen, lower alkyl or $C(=O)OR^{4B}$, wherein $R^{4B}$ is hydrogen, lower alkyl, lower heteroalkyl, aryl, heteroaryl, -(alkyl)aryl or -(alkyl)heteroaryl; each occurrence of X is independently a halogen; w is an integer from 0 to 3 and x is an integer from 1 to 6; whereby each of the foregoing alkyl and heteroalkyl moieties may be linear or branched, substituted or unsubstituted, cyclic or acyclic, and each of the foregoing aryl, heteroaryl, -(alkyl)aryl and -(alkyl)heteroaryl moieties may be substituted or unsusbtituted;

lxxiv) compounds of subset lxxiii) wherein w is 1;

lxxv) compounds of subset lxxiii) wherein w is 0;

lxxvi) compounds of subset lxxiii) wherein x is 1, 3 or 4;

lxxvii) compounds of subset lxxiii) wherein X is chlorine or fluorine;

lxxviii) compounds of subset lxxiii) wherein each occurrence of X is fluorine;

lxxix) compounds of subset lxxiii) wherein $R^{4A}$ is methyl;

lxxx) $R^4$ is methyl, ethyl, propyl, isopropyl or one of:

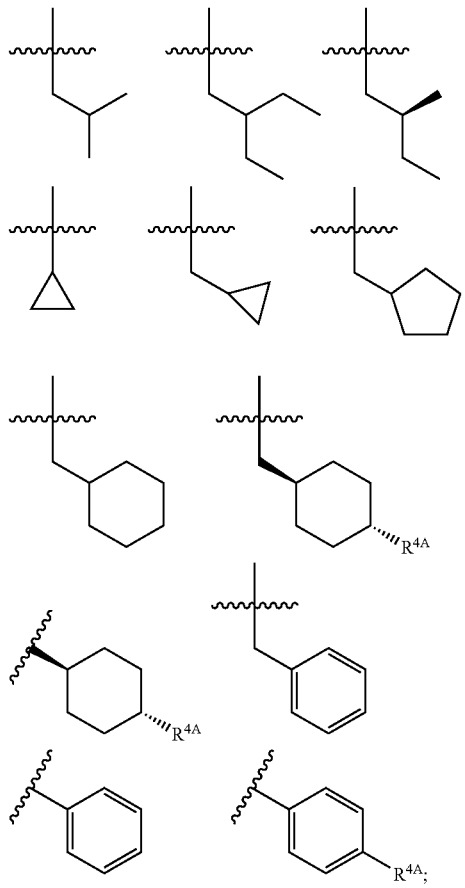

wherein $R^{4A}$ is hydrogen, hydroxyl, lower alkyl, lower alkoxy, halogen, $C(=O)OR^{4B}$, aryl, heteroaryl, -(alkyl)aryl or -(alkyl)heteroaryl, wherein $R^{4B}$ is hydrogen, lower alkyl, lower heteroalkyl, aryl, heteoraryl, -(alkyl)aryl, -(alkyl)heteroaryl, -(heteroalkyl)aryl or -(heteroalkyl)heteroaryl;

lxxxi) $R^4$ is methyl, ethyl, propyl, isopropyl or one of:

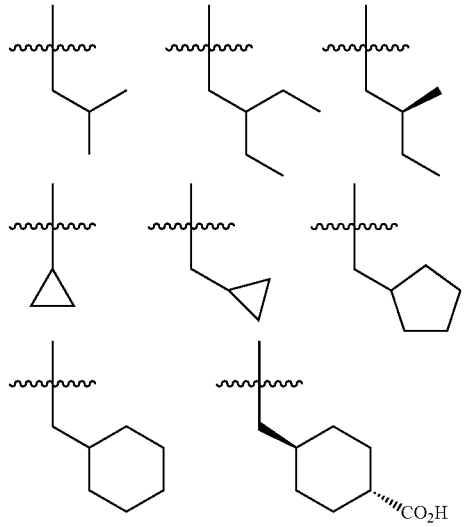

-continued

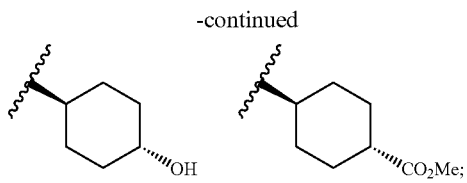

lxxxii) R⁴ is one of:

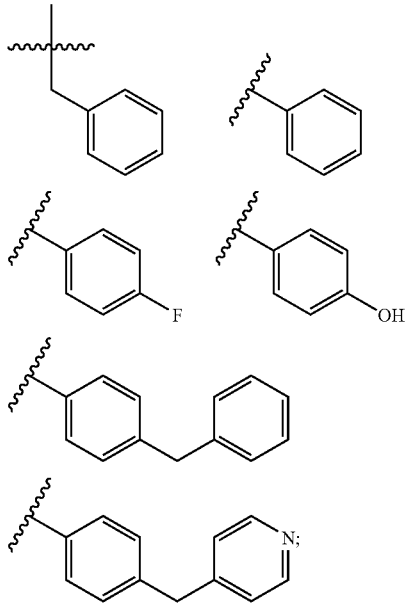

lxxxiii) R⁴ is methyl, ethyl, propyl, isopropyl or one of:

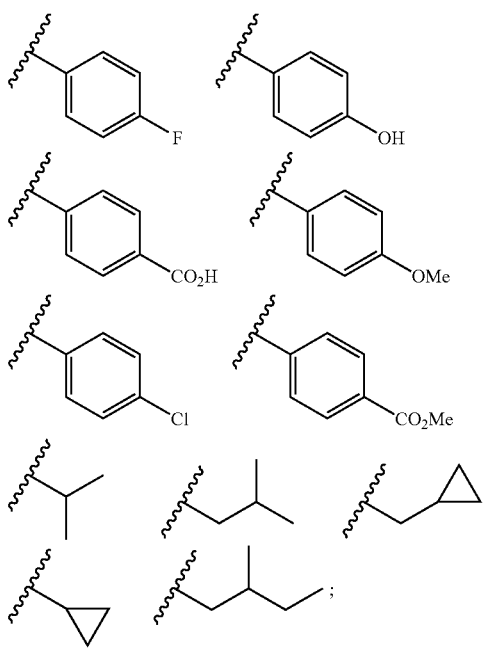

lxxxiv) R⁴ is methyl, ethyl, propyl or one of:

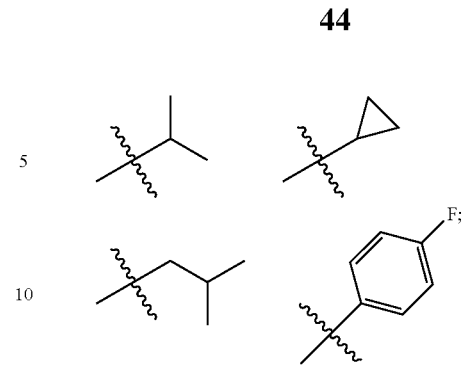

lxxxv) R', R³ and R³' are each hydrogen, X¹ is —C(=O)—, X³ is —C(=O)NH—, R¹ is as described in subset xxiii, R² is as described in subset xxxiv, X² is as described in subset li, and R⁴ is as described in subset lxxxiii;

lxxxvi) R', R³ and R³' are each hydrogen, X¹ is —C(=O)—, X³ is —C(=O)NH—, R¹ is as described in subset xxiv, R² is as described in subset xxxv, X² is as described in subset lii, and R⁴ is as described in subset lxxxiv; and/or lxxxvii) R', R³ and R³' are each hydrogen, X¹ is —C(=O)—, X³ is —C(=O)NH—, R¹ is as described in subset xxiv, R² is as described in subset xxxvi, X² is as described in subset lii, R⁴ is as described in subset lxxxiv.

It will be appreciated that for each of the classes and subclasses described above and herein, any one or more occurrences of aliphatic or heteroaliphatic may independently be substituted or unsubstituted, cyclic or acyclic, linear or branched, saturated or unsaturated and any one or more occurrences of aryl, heteroaryl, cycloaliphatic, cycloheteroaliphatic may be substituted or unsubstituted.

The reader will also appreciate that all possible combinations of the variables described in i)- through lxxxvii) above (e.g., R', R¹, X¹, R², R³, R³', X², X³ and R⁴, among others) are considered part of the invention. Thus, the invention encompasses any and all compounds of formula I generated by taking any possible permutation of variables R', R¹, X¹, R², R³, R³', X², X³ and R⁴, and other variables/substituents (e.g., $R^{X1A}$, $R^{X2A}$, Y, $R^{X3A}$, $R^{4A}$, etc.) as further defined for R', R¹, X¹, R², R³, R³', X², X³ and R⁴, described in i)- through lxxxvii) above.

For example, an exemplary combination of variables described in i)- through lxxxvii) above includes those compounds of Formula I wherein:

R' is hydrogen, alkyl, heteroalkyl, aryl, heteroaryl, -(alkyl)aryl or -(alkyl)heteroaryl;

R¹ is alkyl, heteroalkyl, aryl, heteroaryl, -(alkyl)aryl or -(alkyl)heteroaryl;

X¹ is —C(=O)—, —S(=O)—, —C(=NH)—, —C(=S)—, —NC(=O)—, —NC(=S)—, —N—C(=N—C≡N)—, —NS(O₂)—, —CHR$^{X1A}$—, —SO₂—, —COO—, —C(=O)C(R$^{X1A}$)₂—, or —SC(=O)— wherein each occurrence of R$^{X1A}$ is independently hydrogen, or an aliphatic, heteroaliphatic, aromatic or heteroaromatic moiety;

R² is alkyl, heteroalkyl, aryl, heteroaryl, -(alkyl)aryl or -(alkyl)heteroaryl;

R³ is hydrogen, halogen, alkyl, heteroalkyl, aryl, heteroaryl, -(alkyl)aryl or -(alkyl)heteroaryl;

R³' is hydrogen, halogen, or lower alkyl;

R⁴ is alkyl, heteroalkyl, aryl, heteroaryl, -(alkyl)aryl or -(alkyl)heteroaryl;

$X^2$ is absent, $-NR^{X2A}-$, $-(CHR^{X2A})_j-$, $-NR^{X2A}Y-$, or $-(CHR^{X2A})_jY-$ wherein each occurrence of $R^{X2A}$ is independently hydrogen or an aliphatic, heteroaliphatic, aromatic or heteroaromatic moiety, each occurrence of Y is independently

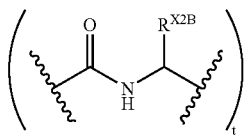

wherein, for each independent occurrence of t, $R^{X2B}$ is hydrogen, or an aliphatic, heteroaliphatic, aromatic or heteroaromatic moiety, and wherein each occurrence of j and t is independently an integer from 1 to 4; and $X^3$ is absent, $-NHCO-$, $-NHSO_2-$, $-NHCONH-$, $-NHCOO-$, $-CH_2NH-$, $-C(=O)-$, $-S(=O)-$, $-C(=NH)-$, $-C(=S)-$, $-NC(=S)N-$, $-N-C(=N-C\equiv N)N-$, $-NS(O_2)N-$, $-SO_2-$, $-CONR^{X3A}-$, $-COO-$, $-(CHR^{X3A})_k-$, $-O-$, or $-NR^{X3A}-$, wherein each occurrence of $R^{X3A}$ is independently hydrogen, an aliphatic, heteroaliphatic, aromatic or heteroaromatic moiety, and k is an integer from 1 to 3.

Other exemplary combinations are illustrated by compounds of the following subgroups I and II:

I. Compounds Having the Structure (and Pharmaceutically Acceptable Derivatives Thereof):

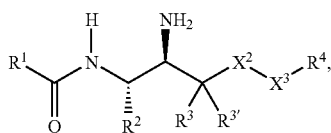

wherein $R^1$, $R^2$, $R^3$, $R^{3'}$, $X^2$, $X^3$ and $R^4$ are as defined generally and in classes and subclasses herein.

In certain embodiments,

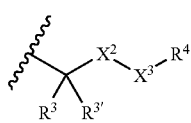

has one of the following structures:

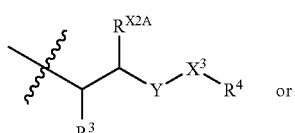

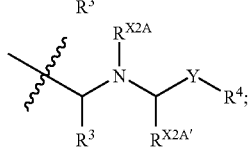

wherein $R^3$ is hydrogen, halogen or an aliphatic, heteroaliphatic, aryl, heteroaryl, -(alkyl)aryl, -(alkyl)heteroaryl, -(heteroalkyl)aryl, or -heteroalkyl)heteroaryl moiety;

$R^4$ is an aliphatic, heteroaliphatic, aryl, heteroaryl, -(alkyl)aryl, -(alkyl)heteroaryl, -(heteroalkyl)aryl, or -heteroalkyl)heteroaryl moiety, or $R^4$, taken together with $R^{X2A'}$ or a substituent present on Y or $X^3$, may form a cycloaliphatic, cycloheteroaliphatic, aryl, or heteroaryl moiety;

$R^{X2A}$ is hydrogen or an aliphatic, heteroaliphatic, aryl, heteroaryl, -(alkyl)aryl, -(alkyl)heteroaryl, -(heteroalkyl)aryl, or -(heteroalkyl)heteroaryl moiety;

$R^{X2A'}$ is hydrogen, or an aliphatic, heteroaliphatic, aryl, heteroaryl, -(alkyl)aryl, -(alkyl)heteroaryl, -(heteroalkyl)aryl, or -(heteroalkyl)heteroaryl moiety, or $R^{X2A'}$ taken together with $R^4$ may form a cycloaliphatic, cycloheteroaliphatic, aryl or heteroaryl moiety;

Y is independently absent or is

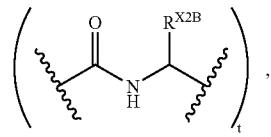

wherein, for each independent occurrence of t, $R^{X2B}$ is hydrogen, or an aliphatic, heteroaliphatic, aryl, heteroaryl, -(alkyl)aryl, -(alkyl)heteroaryl, -(heteroalkyl)aryl, or -heteroalkyl)heteroaryl moiety, or one occurrence of $R^{X2B}$ taken together with $R^4$ may form a cycloaliphatic, cycloheteroaliphatic, aryl or heteroaryl moiety; t is an integer from 1 to 4; and $X^3$ is absent, $-NHCO-$, $-NHSO_2-$, $-NHCONH-$, $-NHCOO-$, $-CH_2NH-$, $-C(=O)-$, $-S(=O)-$, $-C(=NH)-$, $-C(=S)-$, $-NC(=S)N-$, $-N-C(=N-C\equiv N)N-$, $-NS(O_2)N-$, $-SO_2-$, $-C(=O)NR^{X3A}-$, $-C(=S)NR^{X3A}-$, $-COO-$, $(CHR^{X3A})_k-$, $-O-$, $-CH_2NR^{X3A}-$, or $-NR^{X3A}-$, wherein each occurrence of $R^{X3A}$ is independently hydrogen, an aliphatic, heteroaliphatic, aryl, heteroaryl, -(alkyl)aryl, -(alkyl)heteroaryl, -(heteroalkyl)aryl, or -heteroalkyl)heteroaryl moiety, or $R^{X3A}$ taken together with $R^4$ may form a cycloaliphatic, cycloheteroaliphatic, aryl or heteroaryl moiety, and k is an integer from 1 to 3.

In certain embodiments,

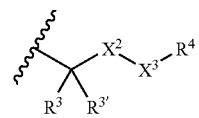

has one of the following structures:

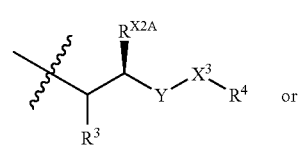

-continued

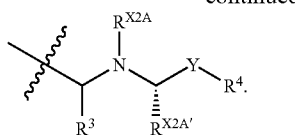

In certain embodiments,

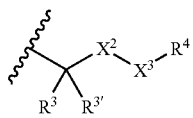

has one of the following structures:

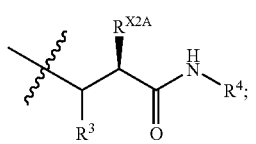

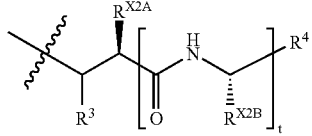

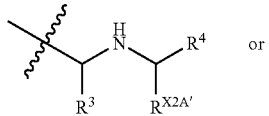

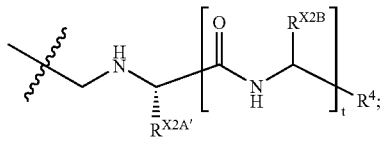

wherein $R^3$, $R^4$, $R^{X2A}$, $R^{X2A'}$, $R^{X2B}$ and t are as defined above and in classes and subclasses herein.

In certain embodiments,

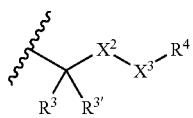

has one of the following structures:

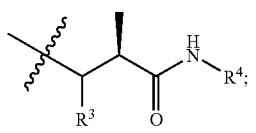

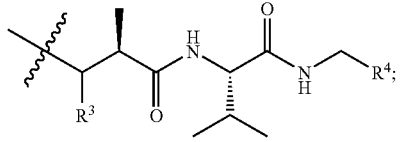

-continued

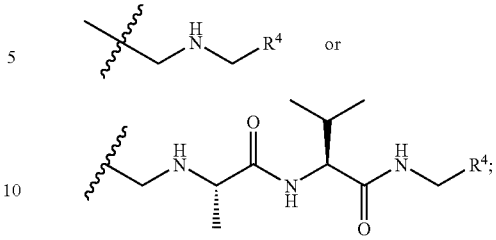

wherein $R^3$ and $R^4$ are as defined above and in classes and subclasses herein.

II. Compounds Having the Structure (and Pharmaceutically Acceptable Derivatives Thereof):

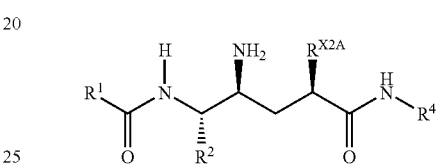

wherein $R^1$, $R^2$, $R^{X2A}$ and $R^4$ are as defined generally and in classes and subclasses herein.

In certain embodiments for compounds as described in subgroups I–II above, $R^1$ is a substituted or unsubstituted aryl, heteroaryl, -(alkyl)aryl, -(alkyl)heteroaryl or heterocyclic moiety. In certain exemplary embodiments, $R^1$ has one of the following structures:

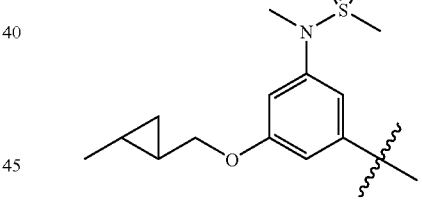

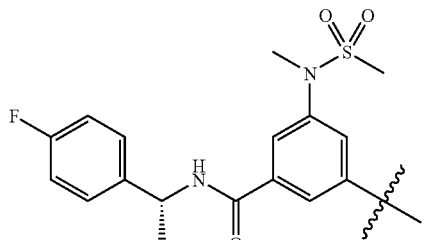

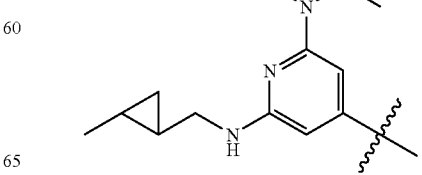

-continued

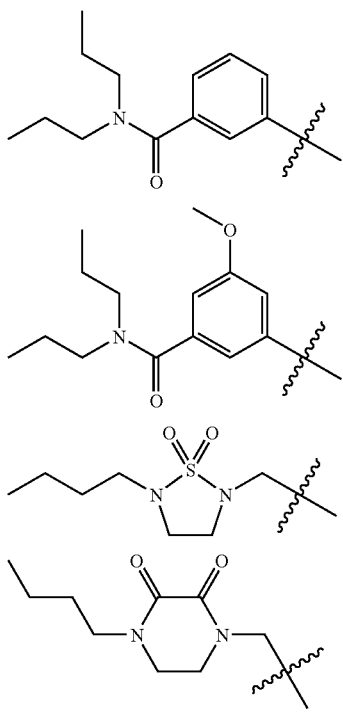

In certain embodiments, for compounds as described in subgroups I–II above, $R^2$ has one of the following structures:

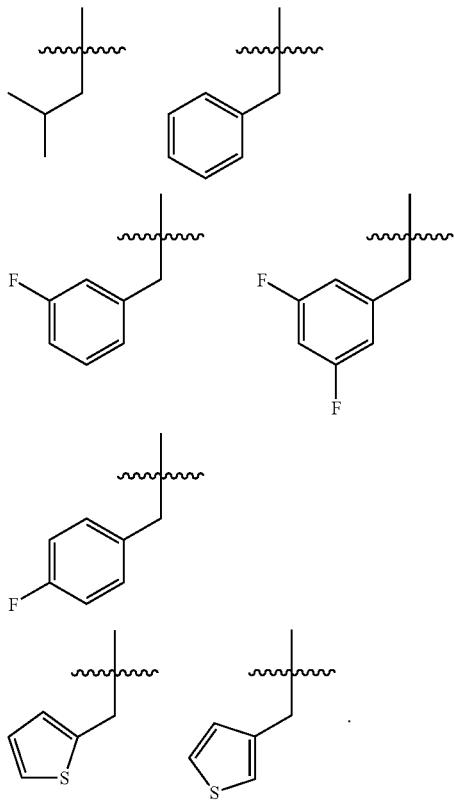

In certain embodiments, for compounds as described in subgroup I above, $R^3$ is halogen. In certain exemplary embodiments, $R^3$ is F. In certain other embodiments, $R^3$ is hydrogen.

In certain embodiments for compounds as described in subgroups I and II above, $R^4$ is substituted or unsubstituted, linear or branched, cyclic or acyclic alkyl, phenyl or —(CH$_2$)phenyl, wherein the phenyl group is optionally substituted with one or more occurrences of $R^{4A}$, wherein $R^{4A}$ is hydrogen, alkyl, heteroalkyl, aryl, heteroaryl, -(alkyl)aryl or —(alkyl)heteroaryl, —OR$^{4B}$, —SR$^{4B}$, —N(R$^{4B}$)$_2$, —SO$_2$N(R$^{4B}$)$_2$, —C(=O)N(R$^{4B}$)$_2$, halogen, —CN, —NO$_2$, —C(=O)OR$^{4B}$, —N(R$^{4B}$)C(=O)R$^{4C}$, wherein each occcurrence of $R^{4B}$ and $R^{4C}$ is independently hydrogen, lower alkyl, lower heteroalkyl, aryl, heteroaryl, -(alkyl)aryl, -(alkyl)heteroaryl, -(heteroalkyl)aryl, -(heteroalkyl)heteroaryl. In certain other exemplary embodiments, $R^4$ is substituted or unsubstituted, linear or branched, cyclic or acyclic alkyl, phenyl or —(CH$_2$)phenyl, wherein the phenyl group is optionally substituted with one or more occurrences of $R^{4A}$, wherein $R^{4A}$ is hydrogen, hydroxyl, alkyl, alkoxy or halogen. In certain exemplary embodiments, $R^4$ has one of the following structures:

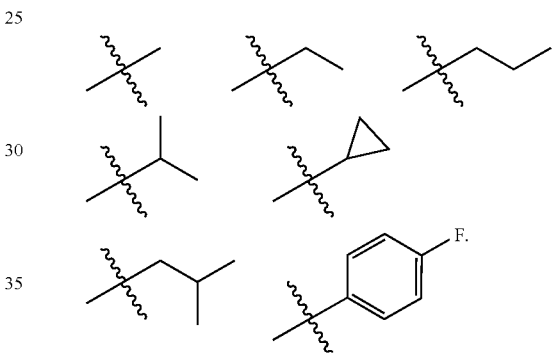

In certain exemplary embodiments, for compounds as described in subgroups I and II above, $R^{X2A}$ is a substituted or unsubstituted, linear or branched lower alkyl moiety. In certain other exemplary embodiments, $R^{X2A}$ is methyl, ethyl, propyl, isopropyl or phenethyl.

It will also be appreciated that for each of the subgroups I–II described above, a variety of other subclasses are of special interest, including, but not limited to those classes described above i)–lxxxvii) and classes, subclasses and species of compounds described above and in the examples herein.

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of formula (I) under different conditions and may exist as one or a combination of polymorphs of compound of general formula (I) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

2) Synthetic Overview:

The practitioner has a a well-established literature of peptide chemistry to draw upon, in combination with the information contained herein, for guidance on synthetic strategies, protecting groups, and other materials and methods useful for the synthesis of the compounds of this invention, including compounds containing the various R', $R^1$, $R^2$, $R^3$, $R^{3'}$ and $R^4$ substituents and $X^1$, $X^2$ and $X^3$ moieties.

The various patent documents and other references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

As described above, the present invention provides novel compounds, specifically compounds having the following general structure:

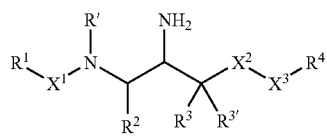

(I)

and pharmaceutically acceptable derivatives thereof, wherein $R^1$, $R^2$, $R^3$, $R^{3'}$, R', $X^1$, $X^2$, $X^3$ and $R^4$ are as defined generally above and in classes and subclasses herein.

It will be appreciated that for compounds as generally described above, certain classes of compounds are of special interest. For example, one class of compounds of special interest includes those compounds wherein the compound has the stereochemistry as shown in Formula ($I^4$):

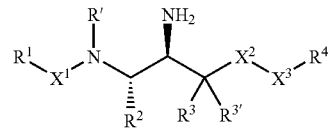

($I^A$)

In yet another aspect of the invention, methods for producing intermediates useful for the preparation of compounds of formulae (I) and ($I^4$) are provided, embodiments of said methods being depicted generally in Schemes A and $A_1$:

Scheme A

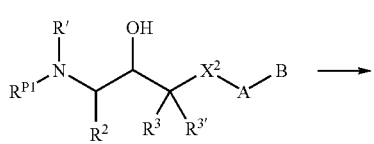

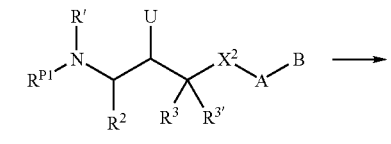

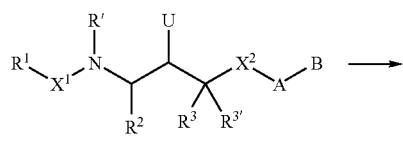

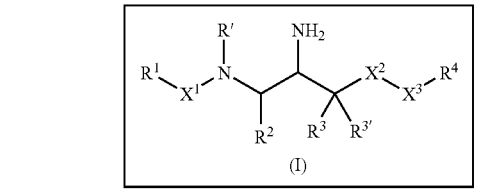

(I)

Scheme $A_1$

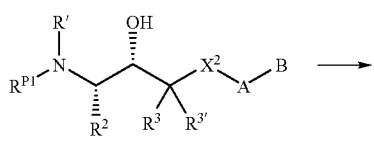

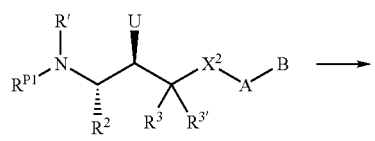

-continued

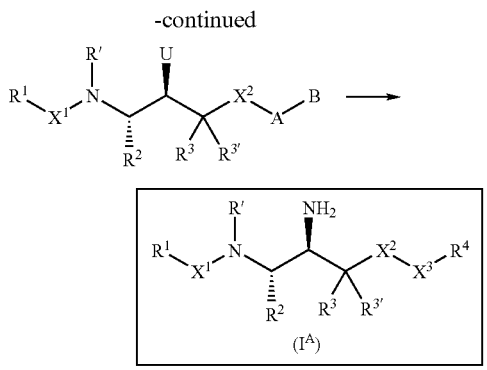

Alternatively, substituent R³' may be introduced at a later stage in the synthesis, as depicted for example in Schemes A₂ and A₃:

Scheme A₂

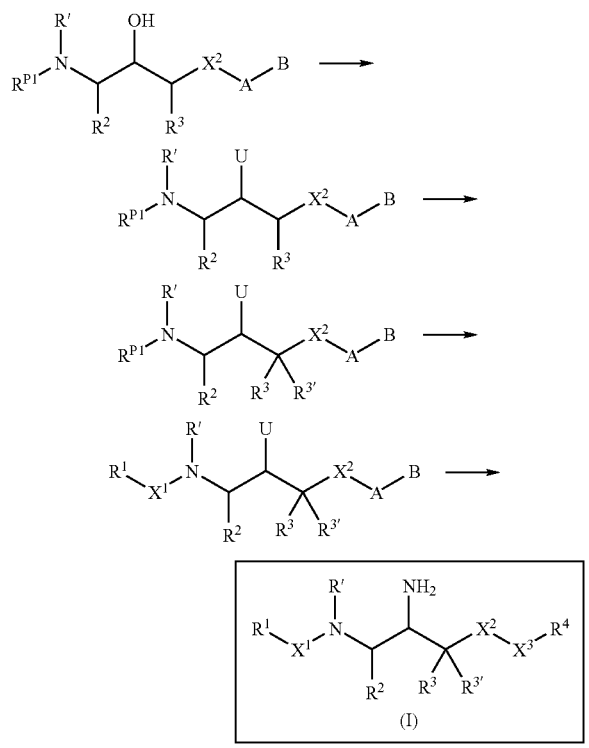

Scheme A₃

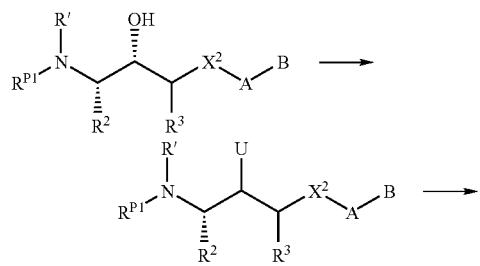

-continued

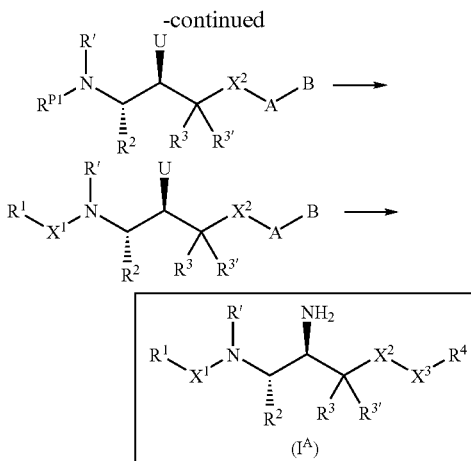

In certain embodiments, the inventive method comprises
i) providing a compound having the structure:

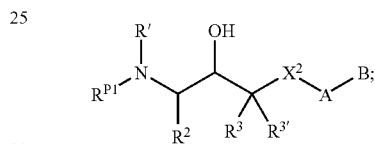

wherein R', R², R³, R³' and X² are as defined generally above and in classes and subclasses herein, $R^{P1}$ is a nitrogen protecting group;

A is absent, —NHCO—, —NHSO₂—, —NHCONH—, —NHCOO—, —CH₂NH—, —C(=O)—, —S(=O)—, —C(=NH)—, —C(=S)—, —NC(=S)N—, —N—C(=N—C≡N)N—, —NS(O₂)N—, —SO₂—, —C(=O)NR⁵—, —C(=S)NR⁵—, —COO—, —(CHR⁵)$_k$—, —O—, —CH₂NR⁵— or —NR⁵—, wherein each occurrence of R⁵ is independently hydrogen, an aliphatic, heteroaliphatic, aryl, heteroaryl, -(alkyl)aryl, -(alkyl)heteroaryl, -(heteroalkyl)aryl, or -heteroalkyl)heteroaryl moiety, and k is an integer from 1 to 3; and B is a protecting group, or an aliphatic, heteroaliphatic, aryl, heteroaryl, -(alkyl)aryl or -(alkyl)heteroaryl moiety, or is —VR$^C$, wherein V is —O—, —NR$^D$—, —C(=O)—, —S(=O)— or —SO₂—, wherein each occurrence of R$^C$ and R$^D$ is independently hydrogen, a protecting group or an aliphatic, heteroaliphatic, aryl, heteroaryl, -(alkyl)aryl or -(alkyl)heteroaryl moiety;

ii) reacting the compound of step (i) under suitable conditions to generate a compound having the structure:

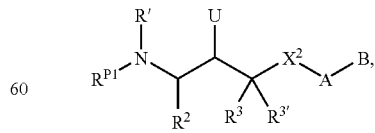

wherein U is —NHR$^{P2}$ or —N₃, wherein R$^{P2}$ is a nitrogen protecting group;

iii) reacting the compound of step (ii) with suitable reagents to generate a compound having the structure:

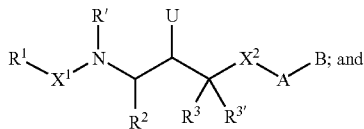

iv) reacting the compound of step (iii) with suitable reagents to generate the free amine having the structure:

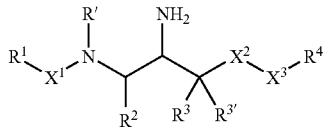

(I)

wherein R', R$^1$, R$^2$, R$^3$, R$^{3'}$, R$^4$, X$^1$, X$^2$ and X$^3$ are as defined generally above and in classes and subclasses herein.

In certain embodiments, the present invention encompasses methods for the preparation of compounds having the general formula (I$^4$), and classes and subclasses herein.

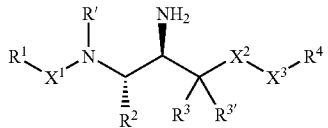

(I$^A$)

In certain embodiments, the method comprises:
i) providing a compound having the structure:

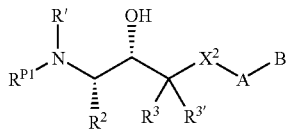

wherein R', R$^2$, R$^3$, R$^{3'}$ and X$^2$ are as defined above,
R$^{P1}$ is a nitrogen protecting group;
A is absent, —NHCO—, —NHSO$_2$—, —NHCONH—, —NHCOO—, —CH$_2$NH—, —C(=O)—, —S(=O)—, —C(=NH)—, —C(=S)—, —NC(=S)N—, —N—C(=N—C≡N)N—, —NS(O$_2$)N—, —SO$_2$—, —C(=O)NR$^5$—, —C(=S)NR$^5$—, —COO—, —(CHR$^5$)$_r$—, —O—, —CH$_2$NR$^5$— or —NR$^5$—, wherein each occurrence of R$^5$ is independently hydrogen, an aliphatic, heteroaliphatic, aryl, heteroaryl, -(alkyl)aryl, -(alkyl)heteroaryl, -(heteroalkyl)aryl, or -heteroalkyl)heteroaryl moiety, and k is an integer from 1 to 3; and
B is a protecting group, or an aliphatic, heteroaliphatic, aryl, heteroaryl, -(alkyl)aryl or -(alkyl)heteroaryl moiety, or is —VR$^C$, wherein V is —O—, —NR$^D$—, —C(=O)—, S(=O) or —SO$_2$—, wherein each occurrence of R$^C$ and R$^D$ is independently hydrogen, a protecting group or an aliphatic, heteroaliphatic, aryl, heteroaryl, -(alkyl)aryl or -(alkyl)heteroaryl moiety;
ii) reacting the compound of step (i) under suitable conditions to generate a compound having the structure:

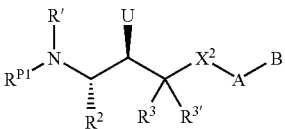

wherein U is —NHR$^{P2}$ or —N$_3$, wherein R$^{P2}$ is a nitrogen protecting group;
iii) reacting the compound of step (ii) with suitable reagents to generate a compound having the structure:

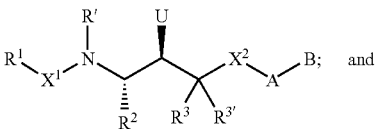

iv) reacting the compound of step (iii) with suitable reagents to generate the free amine having the structure (I$^4$):

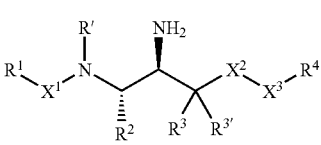

(I$^A$)

wherein R', R$^1$, R$^2$, R$^3$, R$^{3'}$, R$^4$, X$^1$, X$^2$ and X$^3$ are as defined generally above and in classes and subclasses herein.

In yet another aspect of the invention, methods for producing intermediates useful for the preparation of compounds of formulas (I') and (I'$^4$) are provided, embodiments of said methods being depicted generally in Schemes A$_4$ and A$_5$:

Scheme A$_4$

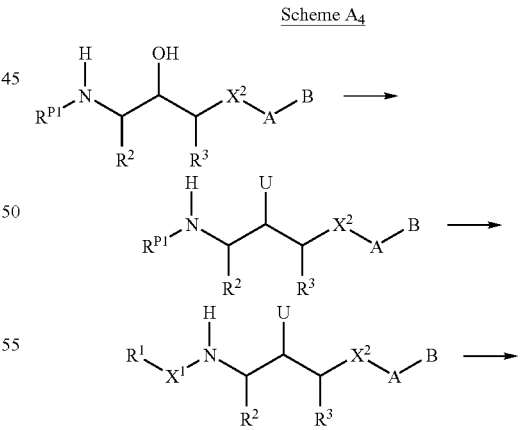

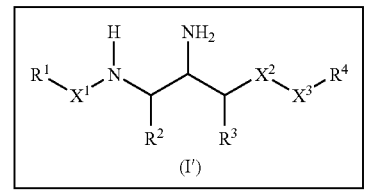

(I')

Scheme A$_5$

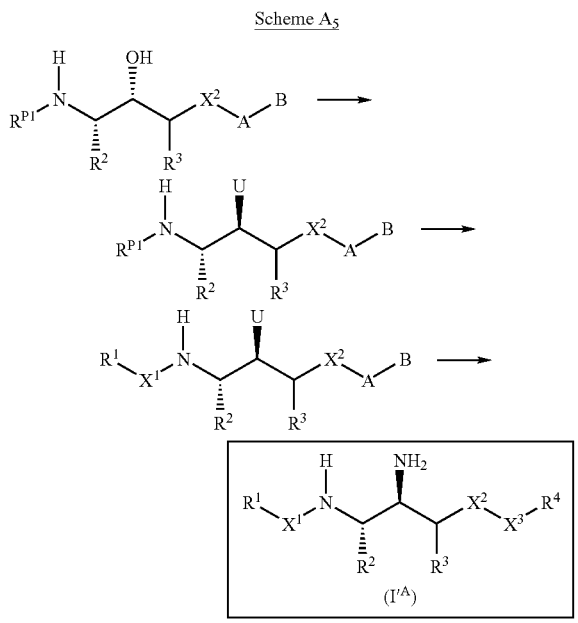

(I'A)

In certain embodiments, the inventive method comprises
i) providing a compound having the structure:

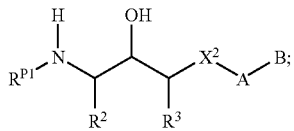

wherein $R^2$, $R^3$, and $X^2$ are as defined above,
$R^{P1}$ is a nitrogen protecting group;
A is absent, —NHCO—, —NHSO$_2$—, —NHCONH—, —NHCOO—, —CH$_2$NH—, —C(=O)—, —S(=O)—, —C(=NH)—, —C(=S)—, —NC(=S)N—, —N—C(=N—C≡N)N—, —NS(O$_2$)N—, —SO$_2$—, —C(=O)NR$^5$—, —C(=S)NR$^5$—, —COO—, —(CHR$^5$)$_r$—, —O—, —CH$_2$NR$^5$— or —NR$^5$—, wherein each occurrence of R$^5$ is independently hydrogen, an aliphatic, heteroaliphatic, aryl, heteroaryl, -(alkyl)aryl, -(alkyl)heteroaryl, -(heteroalkyl)aryl, or -(heteroalkyl)heteroaryl moiety, and k is an integer from 1 to 3; and
B is a protecting group, or an aliphatic, heteroaliphatic, aryl, heteroaryl, -(alkyl)aryl or -(alkyl)heteroaryl moiety, or is —VR$^C$, wherein V is —O—, —NR$^D$—, —C(=O)—, —S(=O)— or —SO$_2$—, wherein each occurrence of R$^C$ and R$^D$ is independently hydrogen, a protecting group or an aliphatic, heteroaliphatic, aryl, heteroaryl, -(alkyl)aryl or -(alkyl)heteroaryl moiety;
ii) reacting the compound of step (i) under suitable conditions to generate a compound having the structure:

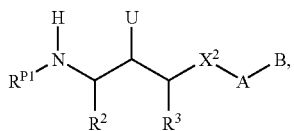

wherein U is —NHR$^{P2}$ or —N$_3$, wherein R$^{P2}$ is a nitrogen protecting group;
iii) reacting the compound of step (ii) with suitable reagents to generate a compound having the structure:

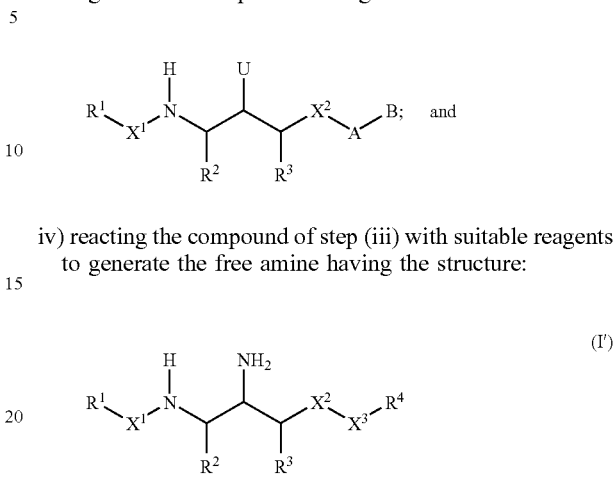

and iv) reacting the compound of step (iii) with suitable reagents to generate the free amine having the structure:

(I')

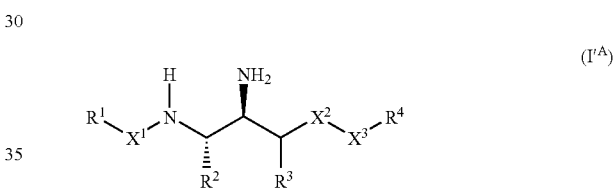

wherein $R^1$, $R^2$, $R^3$, $R^4$, $X^1$, $X^2$ and $X^3$ are as defined generally above and in classes and subclasses herein.

In certain embodiments, the present invention encompasses methods for the preparation of compounds having the general formula (I'$^A$), and classes and subclasses herein.

(I'$^A$)

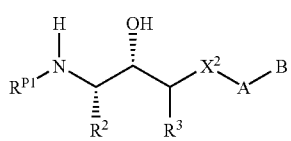

In certain embodiments, the method comprises:
i) providing a compound having the structure:

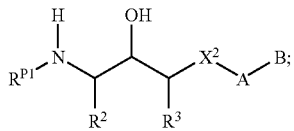

wherein $R^2$, $R^3$, and $X^2$ are as defined above,
$R^{P1}$ is a nitrogen protecting group;
A is absent, —NHCO—, —NHSO$_2$—, —NHCONH—, —NHCOO—, —CH$_2$NH—, —C(=O)—, —S(=O)—, —C(=NH)—, —C(=S)—, —NC(=S)N—, —N—C(=N—C≡N)N—, —NS(O$_2$)N—, —SO$_2$—, —C(=O)NR$^5$—, —C(=S)NR$^5$—, —COO—, —(CHR$^5$)$_r$—, —O—, —CH$_2$NR$^5$— or —NR$^5$—, wherein each occurrence of R$^5$ is independently hydrogen, an aliphatic, heteroaliphatic, aryl, heteroaryl, -(alkyl)aryl, -(alkyl)heteroaryl, -(heteroalkyl)aryl, or -(heteroalkyl)heteroaryl moiety, and k is an integer from 1 to 3; and
B is a protecting group, or an aliphatic, heteroaliphatic, aryl, heteroaryl, -(alkyl)aryl or -(alkyl)heteroaryl moiety, or is —VR$^C$, wherein V is —O—, —NR$^D$—, —C(=O)—, —S(=O)— or —SO$_2$—, wherein each occurrence of R$^C$ and R$^D$ is independently hydrogen, a protecting group or an aliphatic, heteroaliphatic, aryl, heteroaryl, -(alkyl)aryl or -(alkyl)heteroaryl moiety;

ii) reacting the compound of step (i) under suitable conditions to generate a compound having the structure:

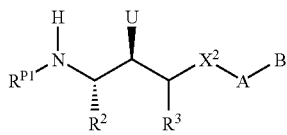

wherein U is —NHR$^{P2}$ or —N$_3$, wherein R$^{P2}$ is a nitrogen protecting group;

iii) reacting the compound of step (ii) with suitable reagents to generate a compound having the structure:

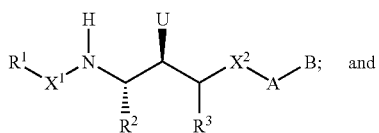

iv) reacting the compound of step (iii) with suitable reagents to generate the free amine having the structure (I'$^A$):

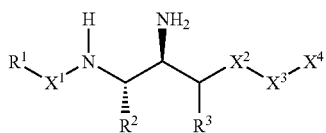

(I'A)

wherein R$^1$, R$^2$, R$^3$, R$^4$, X$^1$, X$^2$ and X$^3$ are as defined generally above and in classes and subclasses herein.

In certain exemplary embodiments, compounds (and methods of synthesis thereof) are provided wherein the compounds have the general formula (I'''$^A$) as shown in Scheme B below:

Scheme B

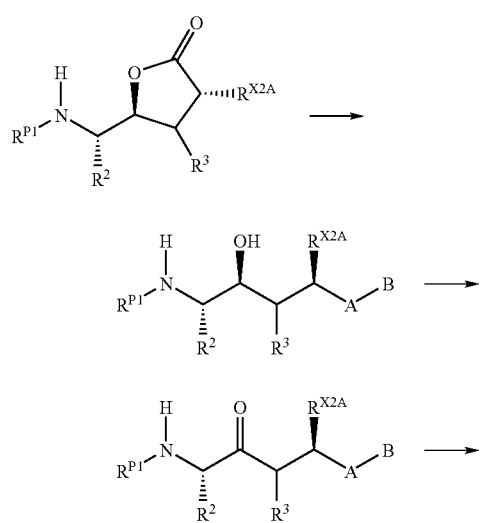

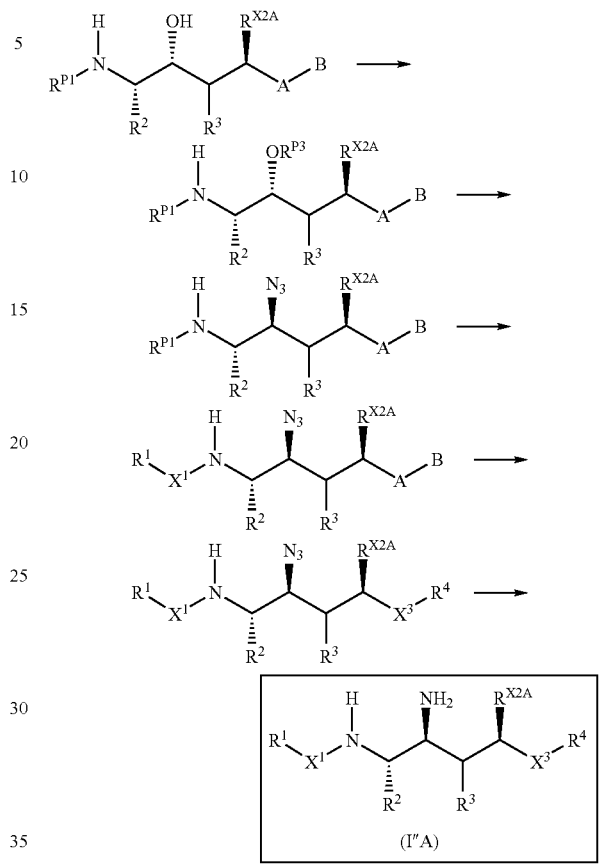

(I''A)

wherein each of R$^1$, X$^1$, RP$^1$, R$^2$, X$^3$, and R$^4$ are as defined above and R$^{P3}$ is an oxygen protecting group.

It will be appreciated that in certain embodiments, as depicted in Scheme B, step i) involves providing a oxo-tetrahydro-furan-2-yl (as described in the Examples herein). Subsequent ring opening, protection, oxidation and stereoselective reduction yields the desired compound of provided in step i). Subsequent reduction to an azide in step ii) and reaction with a suitable reagent (to yield —X$^1$—R$^1$) is also effected. Finally, reaction with a suitable reagent to generate —X$^3$—R$^4$ and deprotection yields the desired compound. It will be appreciated that a variety of methods can be utilized to effect these transformations, including those detailed in the specification herein, and additional general guidance as also described herein.

Additionally, it will appreciated that compounds having the general structures depicted above, wherein X$^3$ is SO$_2$ can be effected using the methodology generally described herein and also methodology described in U.S. Pat. No. 5,585,397, the entire contents of which are hereby incorporated by reference.

Numerous suitable prodrug moieties, and information concerning their selection, synthesis and use are well known in the art. Examples of prodrug moieties of interest include, among others, prodrug moieties that can be attached to primary or secondary amine-containing functionalities. For instance, prodrug moieties of interest include those that can be attached to group —NH$_2$. Examples of such prodrug moieties include the following:

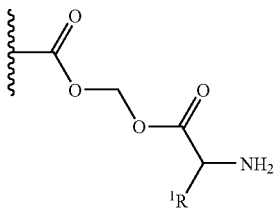

For the synthesis of the prodrug groups, see Borchardt, R. T. et. al., J. Org. Chem. 1997, 43, 3641-3652.

$R^1$ = all natural, unnatural amino acids

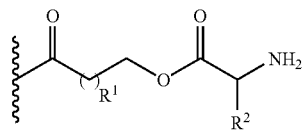

For the synthesis of the prodrug groups, see Zhou, X-X. et. al., PCT WO 99/51613.

$R^1$ = C1–C4 alkyl, cycloalkyl, oxyalkyl, aminoalkyl, etc.
$R^2$ = all natural, unnatural amino acids

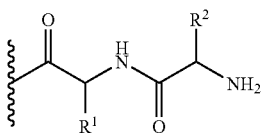

For the synthesis of the prodrug groups, see Ezra, A. et. al., J. Med Chem. 2000, 43, 3641-3652.

$R^1$, $R^2$ = all natural, unnatural amino acids

The present invention encompasses any prodrug form of the compounds described herein. Although certain other exemplary prodrug moieties generated from the inventive compounds amino group are detailed herein, it will be appreciated that the present invention is not intended to be limited to these prodrug moieties; rather, a variety of additional prodrug moieties can be readily identified by a person skilled in the relevant art.

3) Pharmaceutical Compositions

As discussed above, certain of the compounds as described herein exhibit activity generally as inhibitors of aspartyl proteases and more specifically as inhibitors of β-secretase enzyme activity, and have the ability to halt or reduce the production of Aβ from APP and reduce or eliminate the formation of β-amyloid deposits in the brain. Thus, the compounds are useful for treating humans or animals suffering from a condition characterized by a pathological form of β-amyloid peptide, such as β-amyloid plaques, and for helping to prevent or delay the onset of such a condition. Thus, in certain embodiments, compounds of the invention are useful for treating Alzheimer's disease, for helping prevent or delay the onset of Alzheimer's disease, for treating patients with MCI (mild cognitive impairment) and preventing or delaying the onset of Alzheimer's disease in those who would progress from MCI to AD, for treating Down's syndrome, for treating humans who have Hereditary Cerebral Hemmorhage with Amyloidosis of the Dutch-Type, for treating cerebral amyloid angiopathy and preventing its potential consequences, i.e. single and recurrent lobal hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type Alzheimer's disease. The compounds and compositions of the invention are particularly useful for treating or preventing Alzheimer's disease. When treating or preventing these diseases, the compounds of the invention can either be used individually or in combination.

Accordingly, in another aspect of the present invention, pharmaceutical compositions are provided, which comprise any one of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an approved agent for the treatment of Alzheimer's Disease, or it may be any one of a number of agents undergoing approval in the Food and Drug Administration that ultimately obtain approval for the treatment any disorder suffering from a condition characterized by a pathological form of β-amyloid peptide. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot may form are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. These dosage may form are made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. For example, compounds of the invention can be used in combination, with each other, or with other therapeutic agents or approaches used to treat or prevent the conditions described above and herein. Exemplary agents include, but are not limited to: acetylcholine esterase inhibitors such as tacrine (tetrahydroaminoacridine, marketed as COGNEX®), donepezil hydrochloride (marketed as Aricept® and rivastigmine (marketed as Exelon®); gamma-secretase inhibitors; anti-inflammatory agents such as cyclooxygenase II inhibitors; anti-oxidants such as Vitamin E and ginkolides; immunological approaches, such as, for example, immunization with Aβ peptide or administration of anti-Aβ peptide antibodies; statins; and direct or indirect neurotropic agents such as Cerebrolysin®V, AIT-082 (Emilieu, 2000, *Arch. Neurol.* 57:454), and other neurotropic agents of the future. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another Alzheimer's agent), or they may achieve different effects (e.g., control of any adverse effects). In certain embodiments, the pharmaceutical compositions of the present invention further comprises one or more additional therapeutically active ingredients (e.g., palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs.

4) Research Uses, Pharmaceutical Uses and Methods of Treatment

Research Uses

According to the present invention, the inventive compounds may be assayed in any of the available assays known in the art for identifying compounds having protease inhibitory activity. For example, the assay may be cellular or non-cellular, in vivo or in vitro, high- or low-throughput format, etc.

In certain exemplary embodiments, compounds of this invention were assayed for their ability to inhibit aspartyl proteases, more specifically BACE.

Thus, in one aspect, compounds of this invention which are of particular interest include those which:
are inhibitors of aspartyl proteases;
exhibit the ability to inhibit BACE (β-secretase enzyme activity);
exhibit the ability to inhibit Aβ peptide production;
exhibit the ability to halt or reduce the production of Aβ from APP and reduces or eliminates the formation of β-amyloid deposits in the brain;
are useful for treating mammals (e.g., humans) or animals suffering from a condition characterized by a pathological form of β-amyloid peptide, such as β-amyloid plaques, and for helping to prevent or delay the onset of such a condition;
exhibit a favorable therapeutic profile (e.g., safety, efficacy, and stability).

In certain embodiments, compounds of the invention are aspartyl protease inhibitors. In certain exemplary embodiments, inventive compounds are selective BACE inhibitors. In certain exemplary embodiments, inventive compounds have $^{BACE}K_i^{app} \leq 10$ μM. In certain other embodiments, inventive compounds have $^{BACE}K_i^{app} \leq 7.5$ μM. In certain other embodiments, inventive compounds have $^{BACE}K_i^{app} \leq 5$ μM. In certain other embodiments, inventive compounds have $^{BACE}K_i^{app} \leq 2.5$ μM. In certain other embodiments, inventive compounds have $^{BACE}K_i^{app} \leq 1$ μM. In certain other embodiments, inventive compounds have $^{BACE}K_i^{app} \leq 750$ nM. In certain other embodiments, inventive compounds have $^{BACE}K_i^{app} \leq 500$ nM. In certain other embodiments, inventive compounds have $^{BACE}K_i^{app} \leq 250$ nM. In certain other embodiments, inventive compounds have $^{BACE}K_i^{app} \leq 100$ nM. In certain other embodiments, inventive compounds have $^{BACE}K_i^{app} \leq 80$ nM. In certain other embodiments, inventive compounds have $^{BACE}K_i^{app} \leq 60$ nM. In certain other embodiments, inventive compounds have $^{BACE}K_i^{app} \leq 50$ nM. In certain other embodiments, inventive compounds have $^{BACE}K_i^{app} \leq 30$ nM. In certain other embodiments, inventive compounds have $^{BACE}K_i^{app} \leq 20$ nM. In certain other embodiments, inventive compounds have $^{BACE}K_i^{app} \leq 10$ nM.

In certain embodiments, $^{CatD}K_i^{app}$ for compounds of the invention is $\geq 2$ fold greater than $^{BACE}K_i^{app}$. In certain other embodiments, $^{CatD}K_i^{app}$ for compounds of the invention is $\geq 3$ fold greater than $^{BACE}K_i^{app}$. In certain other embodiments, $^{CatD}K_i^{app}$ for compounds of the invention is $\geq 4$ fold greater than $^{BACE}K_i^{app}$. In certain other embodiments, $^{CatD}K_i^{app}$ for compounds of the invention is $\geq 5$ fold greater than $^{BACE}K_i^{app}$. In certain embodiments, $^{CatD}K_i^{app}$ for compounds of the invention is $\geq 7.5$ fold greater than $^{BACE}K_i^{app}$. In certain embodiments, $^{CatD}K_i^{app}$ for compounds of the invention is $\geq 10$ fold greater than $^{BACE}K_i^{app}$. In certain embodiments, $^{CatD}K_i^{app}$ for compounds of the invention is $\geq 25$ fold greater than $^{BACE}K_i^{app}$. In certain embodiments, $^{CatD}K_i^{app}$ for compounds of the invention is $\geq 50$ fold greater than $^{BACE}K_i^{app}$. In certain embodiments, $^{CatD}K_i^{app}$ for compounds of the invention is $\geq 75$ fold greater than $^{BACE}K_i^{app}$. In certain embodiments, $^{CatD}K_i^{app}$ for compounds of the invention is $\geq 100$ fold greater than $^{BACE}K_i^{app}$. In certain embodiments, $^{CatD}K_i^{app}$ for compounds of the invention is $\geq 150$ fold greater than $^{BACE}K_i^{app}$. In certain embodiments, $^{CatD}K_i^{app}$ for compounds of the invention is $\geq 200$ fold greater than $^{BACE}K_i^{app}$. In certain embodiments, $^{CatD}K_i^{app}$ for compounds of the invention is $\geq 250$ fold greater than $^{BACE}K_i^{app}$. In certain embodiments, $^{CatD}K_i^{app}$ for compounds of the invention is $\geq 300$ fold greater than $^{BACE}K_i^{app}$. In certain embodiments, $^{CatD}K_i^{app}$ for compounds of the invention is $\geq 500$ fold greater than $^{BACE}K_i^{app}$. In certain embodiments, $^{CatD}K_i^{app}$ for compounds of the invention is $\geq 1000$ fold greater than $^{BACE}K_i^{app}$.

In certain exemplary embodiments, inventive compounds have $^{Cell}IC_{50}$ values $\leq 10$ μM. In certain other embodiments, inventive compounds have $^{Cell}IC_{50}$ values $\leq 7.5$ μM. In certain other embodiments, inventive compounds have $^{Cell}IC_{50}$ values $\leq 5$ μM. In certain other embodiments, inventive compounds have $^{Cell}IC_{50}$ values $\leq 2.5$ μM. In certain other embodiments, inventive compounds have $^{Cell}IC_{50}$ values $\leq 1$ μM. In certain other embodiments, inventive compounds have $^{Cell}IC_{50}$ values $\leq 750$ nM. In certain other embodiments, inventive compounds have $^{Cell}IC_{50}$ values $\leq 500$ nM. In certain other embodiments, inventive compounds have $^{Cell}IC_{50}$ values $\leq 250$ nM. In certain other embodiments, inventive compounds have $^{Cell}IC_{50}$ values $\leq 100$ nM. In certain other embodiments, inventive compounds have $^{Cell}IC_{50}$ values $\leq 80$ nM. In certain other embodiments, inventive compounds have $^{Cell}IC_{50}$ values $\leq 60$ nM. In certain other embodiments, inventive compounds have $^{Cell}IC_{50}$ values $\leq 50$ nM. In certain other embodiments, inventive compounds have $^{Cell}IC_{50}$ values $\leq 30$ nM. In certain other embodiments, inventive compounds have $^{Cell}IC_{50}$ values $\leq 20$ nM. In certain other embodiments, inventive compounds have $^{Cell}IC_{50}$ values $\leq 10$ nM.

Pharmaceutical Uses and Methods of Treatment

As discussed above, without wishing to be bound by any particular theory, certain of the compounds as described herein exhibit activity generally as inhibitors of aspartyl proteases and more specifically as inhibitors of β-secretase enzyme activity. In certain embodiments compounds exhibit the ability to halt or reduce the production of Aβ from APP and reduce or eliminate the formation of β-amyloid deposits in the brain and thus the compounds are useful for treating humans or animals suffering from a condition characterized by a pathological form of β-amyloid peptide, such as β-amyloid plaques, and for helping to prevent or delay the onset of such a condition (e.g., Alzheimer's Disease). Thus, in certain embodiments, compounds of the invention are useful for treating Alzheimer's disease, for helping prevent or delay the onset of Alzheimer's disease, for treating patients with MCI (mild cognitive impairment) and preventing or delaying the onset of Alzheimer's disease in those who would progress from MCI to AD, for treating Down's syndrome, for treating humans who have Hereditary Cerebral Hemmorhage with Amyloidosis of the Dutch-Type, for treating cerebral amyloid angiopathy and preventing its potential consequences, i.e. single and recurrent lobal hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type Alzheimer's disease. The compounds and compositions of the invention are particularly useful for treating or preventing Alzheimer's disease. When treating or preventing these diseases, the compounds of the invention can either be used individually or in combination.

In certain embodiments, the method involves the administration of a therapeutically effective amount of the compound or a pharmaceutically acceptable derivative thereof to a subject (including, but not limited to a human or animal) in need of it.

As described in more detail herein, in certain embodiments, compounds of the invention are useful as inhibitors of aspartyl proteases. Generally, compounds of the invention exhibit the ability to inhibit aspartyl protease enzyme activity and thus compounds of the invention generally are useful for the treatment of disorders mediated by aspartyl protease enzyme activity. More specifically, compounds of the invention exhibit activity as inhibitors of β-secretase enzyme activity and A β peptide production. Thus, in certain embodiments, the present invention provides compounds useful for the treatment of disorders mediated by a pathological form of β-amyloid peptide, such as , amyloid plaques, and for helping to prevent or delay the onset of such a condition.

Thus, in certain embodiments, compounds of the invention are useful for treating Alzheimer's disease, for helping prevent or delay the onset of Alzheimer's disease, for treating patients with MCI (mild cognitive impairment) and preventing or delaying the onset of Alzheimer's disease in those who would progress from MCI to AD, for treating Down's syndrome, for treating humans who have Hereditary Cerebral Hemmorhage with Amyloidosis of the Dutch-Type, for treating cerebral amyloid angiopathy and preventing its potential consequences, i.e. single and recurrent lobal hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type Alzheimer's disease. The compounds and compositions of the invention are particularly useful for treating or preventing Alzheimer's disease. When treating or preventing these diseases, the compounds of the invention can either be used individually or in combination.

Thus, as described above, in another aspect of the invention, a method for the treatment of disorders useful for the treatment (or prevention) of disorders mediated by a pathological form of β-amyloid peptide, such as β amyloid plaques, is provided comprising administering a therapeutically effective amount of a compound of Formula (I) or ($I^4$), or any classes and subclasses of these compounds as described herein, to a subject in need thereof. It will be appreciated that the compounds and compositions, according to the method of the present invention, may be administered using any amount and any route of administration effective for the treatment of disorders by a pathological form of β-amyloid peptide, such as β amyloid plaques. Thus, the expression "effective amount" as used herein, refers to a sufficient amount of agent to inhibit the production of A β peptide, and to exhibit a therapeutic effect. The exact amount required will vary from subject to subject, depending on the species, age, and general condition of the subject, the severity of the infection, the particular therapeutic agent, its mode of administration, and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, 155–173, 2001, which is incorporated herein by reference in its entirety).

Another aspect of the invention relates to a method for inhibiting β-secretase activity in a biological sample or a patient, which method comprises administering to the patient, or contacting said biological sample with a compound of formula I or a composition comprising said compound.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50–100 mg/kg) can be administered to a subject. In certain embodiments, compounds are administered orally or parenterally.

TREATMENT KIT

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

EXAMPLE 1

This example describes the enzyme assay for determining the apparent $K^i$ of the compounds of the present invention.

The BACE enzyme used for inhibition analyses, BACE-HT, was produced from baculovirus-infected insect cells, and corresponded to the pro form of the soluble N-terminal protease domain (residues 22–454, starting from the N-terminal methionine), followed by a short linker and C-terminal 6×His tag.

Compounds were tested for their ability to inhibit BACE hydrolysis of the internally quenched fluorescent substrate, FS-1 (Ermolieff et al., Biochemistry 39:12450–12456 (2000)):

FS1: NH$_2$-Arg-Glu(EDANS)-Glu-Val-Asn-Leu-↓-Asp-Ala-Glu-Phe-Lys(DABCYL)-Arg-COOH

FS-2: MOCAc-Ser-Glu-Val-Asn-Leu-↓-Asp-Ala-Glu-Phe-Lys(DNP)-Arg-Arg-COOH where EDANS is 5-((2-aminoethyl)amino)napthalene-1-sulfonic acid; DABCYL is 4-((4-dimethylamino)phenyl) azo)benzoic acid; MOCAc is 7-methoxycoumarin-4-yl) acetic acid; and DNP is 2,4-dinotriphenylacetic acid.

FS-1 and FS-2 correspond to the Swedish APP β-site sequence, flanked by either an EDANS or MOCAc fluorophore on the N-terminus and a DABCYL or DNP quenching group near the C-terminus. In the intact state, the DABCYL or DNP group quenches the EDANS or MOCAc (respectively) fluorescence by virtue of their close proximity. In the intact state, the DABCYL group quenches the EDANS fluorescence by virtue of their close proximity. Upon cleavage at the site indicated by the arrow by BACE, the quenching is relieved and fluorescence is observed using $\lambda_{excitation}$=350 nm and $\lambda_{emission}$=490 nm or $\lambda_{excitation}$=328 nm and $\lambda_{emission}$=440 nm (MOCAc). For determination of apparent inhibition constant ($K_i^{app}$) for various inhibitors, the initial rates of FS-1 hydrolysis in the presence of various concentrations of inhibitors were measured and fit to the Morrison equation (Williams and Morrison, Methods Enzymol. 63: 437–467 (1979)):

$$v = v_0 \cdot \frac{[E]_0 - [I]_0 - K_i^{app} + \sqrt{([E]_0 - [I]_0 - K_i^{app})^2 + 4[E]_0 K_i^{app}}}{2[E]_0}$$

where v is the initial rate measured in the presence of $[I]_0$, the inhibitor concentration, using an enzyme concentration $[E]_0$. $v_0$ is the initial rate measured in the absence of inhibitor.

Inhibitors were resuspended in DMSO and serially diluted in DMSO at 20× final assay concentration. Compound dilutions (5 µL) were transferred to Black non-treated 96-well microtiter plates, and resuspended in 85 µL 35.3 µM FS1 substrate in 100 mM sodium acetate buffer, pH 4.5, containing 5.9% DMSO (i.e. 10% final DMSO in assay). Following brief equilibration to room temperature, the reactions were initiated by the addition of 10 µL BACE-HT (100 nM final concentration) and brief mixing. The increase in EDANS fluorescence over time was monitored on a Gemini XS fluorometric plate reader using Softmax pro software. Initial rates were fit to the Morrison equation and $K_i^{app}$'s determined using Graphpad Prism software. A representative range of $K_i^{app}$'s for the compounds is between 1–1000 nM. The range of $K_i^{app}$'s for preferred compounds is 0.1–500 nM.

EXAMPLE 2

This example describes an illustrative set of cell-based assays for testing the ability of the compounds of the present invention to inhibit the secretion of the Aβ peptide from cells expressing high levels of the human amyloid precursor protein ("APP").

A representative set of such cells include A-204 rhabdomyosarcoma cells, human embryonic kidney 293 cells transiently transfected with APP, Chinese hamster ovary cells stably transfected with APP(CHO2B7), and H4 neuroglioma cells stably transfected with APP(H4 β695 wt). The A-204 cells and HEK 293 cells were obtained from ATCC. For HEK 293 transient transfections, a pcDNA3 plasmid containing the human APP gene was obtained from Invitrogen, and cells were transfected with FuGENE 6 transfection reagent (Roche) following manufacturer's protocols. The CHO2B7 and H4 β695 wt lines were obtained from Mayo Clinic (J. Neuroscience Methods 108(2): 171–9 (2001)).

The following media were used for the cell lines: DMEM+glucose, glutamine, sodium pyruvate, pyridoxine-HCl, antibiotics, and 10% FBS (A-204 cells); DMEM+glucose, glutamine, sodium pyruvate, pyridoxine-HCl, non-essential amino acids, antibiotics, and 10% FBS (HEK 293 cells); Ham's F-12+antibiotics, 10% FBS, and 400 µg/ml Zeocin (CHO2B7 cells); and Opti-MEM (Invitrogen)+antibiotics, 10% FBS, and 500 µg/ml geneticin (H4 β695 wt cells).

In the assay, cells were pre-treated with compounds for 1–2 hours to "wash out" any Aβ in the secretory pathway prior to incubation with compounds for the conditioning period required to generate detectable concentrations of Aβ. The production of secreted Aβ in cultured cells was monitored by sandwich ELISA, using the anti-Aβ monoclonal antibodies 6E10 and 4G8 (Signet Laboratories). The antibody 6E10 (specific to amino acids 1–17 of Aβ) was immobilized to the plate and used for capture, and a biotinylated version of the antibody 4G8 (specific to amino acids 17–24 of Aβ) was used for detection, via subsequent treatment with Neutravidin-horseradish peroxidase conjugate and development with luminescent substrate.

Cells were plated at $2.5 \times 10^5$ cells/well (HEK293 cells in 24 well poly-D-lysine coated plate), $1.3 \times 10^5$ cells/well (A-204 cells) (48 well plates) or $5 \times 10^4$ cells/well (CHO2B7 and H4APP cells) (96 well plates) in appropriate media (500 μL per well for 24 well plates, 300 μL per well for 48 well plates, 150 μL per well for 96 well plates) and grown at 37° C. and 5% $CO_2$ for 16–20 h. Media was aspirated and replaced with appropriate media plus 0.1% DMSO and various concentrations of inhibitors, prepared by resuspension of the appropriate volume of a 1000× solution of inhibitor in DMSO with media on a separate plate. Cells and inhibitors were incubated for 1–2 hours, followed by aspiration of the media and replacement with fresh media solutions having the same concentrations of inhibitors. After a 4–24 hour incubation period (depending on cell type), conditioned media were collected and 100 μL of each sample applied to wells of Nunc Maxisorp white 96-well plates that had been previously coated with 10 μg/mL 6E10 antibody in 50 mM $Na_2CO_3$, (pH 9.0) overnight at 4° C., blocked with Superblock in PBS (Pierce Chemicals; PBS=10 mM sodium phosphate+150 mM NaCl, pH 7.4) for 1 hour at room temperature, and washed 3 times in wash buffer (PBS plus 0.05% Tween 20). Binding was allowed to take place overnight at 4° C., and plates were then washed 8 times and treated with 100 μL/well of 10 nM biotinylated 4G8 antibody in binding buffer (superblock in PBS plus 0.05% Tween 20) for 1 hour at room temperature. Plates were washed 8 times, treated with 100 μL/well of 1.5 μg/Neutravidin-horseradish peroxidase conjugate (Pierce Chemicals) for 40 minutes at room temperature, washed an additional 8 times, and developed with 100 μL/well Supersignal luminescent substrate (Pierce Chemicals) for 2 minutes. Luminescence was measured on a Gemini XS fluorescence/luminescence plate reader, and translated into Aβ concentrations using an internal standard curve of known Aβ concentrations (Aβ 1–40 obtained from Oncogene). In general, $IC_{50}$'s of the compounds of the present invention range from about 5× to about 15× the observed $K_i^{app}$'s against the BACE enzyme as determined using the method of Example 1.

EXAMPLE 3

This example describes permeability experiments using MDCK cells.

MDCK cells, derived from canine kidney, were obtained from American Type Culture Collection (ATCC, Rockville, Md.). Cells were cultured in DMEM medium supplemented with 10% fetal bovine serum, 1 mM sodium pyruvate and 0.01 mg/ml gentamicin. Cells were maintained in a humidified atmosphere with 5% $CO^2$ at 37° C. For transport studies, cells were plated at a density of $50 \times 10^3$ cells/cm$^2$ on 0.4 μm pore size Transwell™ polyester membranes (Corning, Corning, N.Y.). Culture medium was replaced every two days until a tight cell monolayer was formed as measured by preliminary R123 permeability measurements. Compounds, 10 μM, were placed in either the apical or basolateral compartment and the amount of drug in the opposite chamber was measured using LC/MS/MS or fluorometry. The permeability coefficient was calculated using the following equation:

$$P_{app} = (1/AC_0)dQ/dt$$

where A=surface area of the cell monolayers, $C_0$ is the initial concentration and dQ/dt represents the amount of drug flux in a specified time.

EXAMPLE 4

This example describes pharmacokinetic experiments for determining peak plasma and peak brain concentrations using Adult Swiss Weber mice. The peak brain concentration determination also served as a measure for assessing whether the compounds were able to cross the blood brain barrier.

Figure 1B:
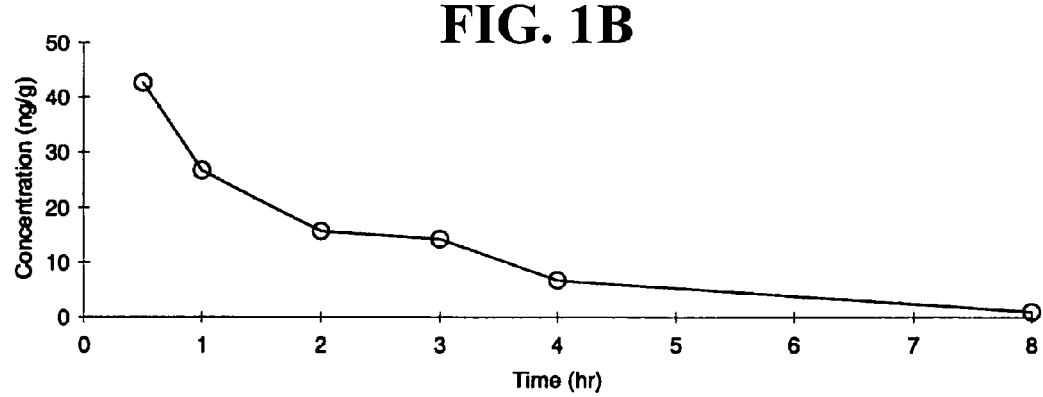
FIG. 1B depicts a brain concentration curve for an exemplary inventive compound.

Adult Swiss Webster mice were administered compounds via tail vein injection. Plasma and brain tissue were collected at 0, 0.5, 1, 2, 3, 4, and 8 hrs. Blood was collected via cardiac puncture. Subsequently, animals were perfused intra-cardially with ice-cold saline; the brain was homogenized in 10 volumes of ice-cold Tris-buffered saline (20 mM Tris, 137 mM NaCl, pH 7.6) and was then frozen at −20° C. Following extraction, compound concentrations in plasma and brain homogenates were measured by LC/MS/MS. Peak plasma and brain concentrations ($C_{max}$) and time to achieve these concentrations ($T_{max}$) were measured directly from concentration versus time profiles. Descriptive pharmacokinetic parameters were calculated using the WinNonlin software package (Pharsight Inc., Mountain View Calif.). FIGS. 1A and 1B are the plasma and brain concentration curves respectively for one of the compounds of the present invention (where each data point is an average concentration from three mice). This compound has a molecular weight of 626, has a $K_i^{app}$ of about 35 nM with a 125 fold selectivity over Cat D, and has an $IC_{50}$ in cells of about 220 nM.

EXAMPLE 5

This example compares the biological properties of a hydroxy-containing compound with an amino-containing compound. The two compounds are of the structure

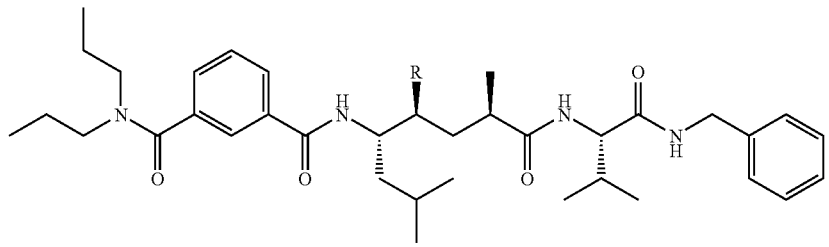

where R is either OH or NH$_2$. In a surprising and unexpected finding, the amino-containing compound possesses several superior biological properties over its hydroxy-containing counterpart.

As it can be seen in the following Table, the amino compound is more potent in cells, is more selective for the BACE enzyme, and show superior ADME properties than its hydroxy counterpart.

| Compound | BACE K$_i$ | IC$_{50}$ (H4 cells) | Cat D K$_i$ | % recovery liver microsomes |
|---|---|---|---|---|
| R = OH | 150 nM | 2000 nM | 20 nM | 0% at 60 minutes |
| R = NH$_2$ | 180 nM | 740 nM | 610 nM | 43% at 60 minutes |

Although both compounds show similar activity against the BACE enzyme (180 nM versus 150 nM), the amino compound is significantly more potent in cells (740 nM versus 2000 nM). Moreover, the amino compound displays over a three fold preference for BACE over Cat D. In contrast, the hydroxy counterpart displays a 7.5 fold preference for Cat D over BACE. In addition, although both the amino and hydroxy compounds were stable in human plasma (100% recovery at 1 hour), the amino compound is much more stable in liver microsomes than its hydroxy counterpart.

These trends appear to be a general phenomenon and have been observed in several scaffolds in addition to one exemplified above.

The K$_i$ for BACE and the IC$_{50}$ determinations were performed as described in Examples 1 and 2 respectively.

The Ki determination for Cat D was performed using the assay conditions derived from Haque et al., *J. Med. Chem.* 42: 1428–1440 (1999) and the following substrate: DABCYL-GLu-Arg-Nle-Phe-Leu-Ser-Phe-Pro-EDANS
where Nle is norleucine and DABCYL and EDANS are as previously defined.

Plasma stability was determined by incubating the compounds in human plasma at a concentration of 1 μM at 37° C. for 0, 30 and 60 minutes. Reactions were stopped by addition of acetonitrile. Protein was precipitated by centrifugation (3000 rpm×10 min) then supernatants were analyzed for remaining parent compound by LC/MS/MS.

Metabolic stability was determined by incubating the compounds with human liver microsomes (100 μg/ml) in 100 mM Tris buffer pH 7.4 for 5 minutes at 37° C. Metabolic reactions were started by addition of NADPH to give a final concentration of 1 μM. Reactions were stopped after 30 and 60 minutes by addition of acetonitrile. Protein was precipitated by centrifugation (3000 rpm×10 min) then supernatants were analyzed for remaining parent compound by LC/MS/MS.

General Description of Synthetic Strategy:

According to the present invention, any available techniques can be used to make or prepare the inventive compounds or compositions including them. For example, a variety of solution phase synthetic methods such as those discussed in detail below may be used. Alternatively or additionally, the inventive compounds may be prepared using any of a variety combinatorial techniques, parallel synthesis and/or solid phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1–17, John Wiley and Sons, New York, N.Y., 1991; Rodd 1989 "Chemistry of Carbon Compounds", vols. 1–5 and supps, Elsevier Science Publishers, 1989; "Organic Reactions", vols 1–40, John Wiley and Sons, New York, N.Y., 1991; March 2001, "Advanced Organic Chemistry", 5th ed. John Wiley and Sons, New York, N.Y.; and Larock 1989, "Comprehensive Organic Transformations", VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

General Reaction Procedures:

Unless mentioned specifically, reaction mixtures were stirred using a magnetically driven stirrer bar. An inert atmosphere refers to either dry argon or dry nitrogen. Reactions were monitored either by thin layer chromatography, by proton nuclear magnetic resonance (NMR) or by high-pressure liquid chromatography (HPLC), of a suitably worked up sample of the reaction mixture.

General Work Up Procedures:

Unless mentioned specifically, reaction mixtures were cooled to room temperature or below then quenched, when necessary, with either water or a saturated aqueous solution of ammonium chloride. Desired products were extracted by partitioning between water and a suitable water-immiscible solvent (e.g. ethyl acetate, dichloromethane, diethyl ether). The desired product containing extracts were washed appropriately with water followed by a saturated solution of brine. On occasions where the product containing extract was deemed to contain residual oxidants, the extract was washed with a 10% solution of sodium sulphite in saturated aqueous sodium bicarbonate solution, prior to the aforementioned washing procedure. On occasions where the product containing extract was deemed to contain residual acids, the extract was washed with saturated aqueous sodium bicarbonate solution, prior to the aforementioned washing procedure (except in those cases where the desired product itself had acidic character). On occasions where the product containing extract was deemed to contain residual bases, the extract was washed with 10% aqueous citric acid solution, prior to the aforementioned washing procedure (except in those cases where the desired product itself had basic character). Post washing, the desired product containing extracts were dried over anhydrous magnesium sulphate, and then filtered. The crude products were then isolated by removal of solvent(s) by rotary evaporation under reduced pressure, at an appropriate temperature (generally less than 45° C.).

General Purification Procedures:

Unless mentioned specifically, chromatographic purification refers to flash column chromatography on silica, using a single solvent or mixed solvent as eluent. Suitably purified desired product containing elutes were combined and concentrated under reduced pressure at an appropriate temperature (generally less than 45° C.) to constant mass. Final compounds were dissolved in 50% aqueous acetonitrile, filtered and transferred to vials, then freeze-dried under high vacuum before submission for biological testing.

Synthesis of Exemplary Compounds:

The practitioner has a well-established literature of amino acid and peptide chemistry to draw upon, in combination with the information contained in the many examples which follow, for guidance on synthetic strategies, protecting groups, and other materials and methods useful for the synthesis of the compounds of this invention, including compounds containing the various $R^1$, $R^2$ and $R^3$ substituents and $X^1$, $X^2$ and $X^3$ moieties. Described generally below, are procedures and general guidance for the synthesis of compounds as described generally and in subclasses and species herein. In addition, synthetic guidance for the synthesis of amino acid derivatives and peptide analogues (and protease inhibitors more generally) can be found in U.S. Pat. Nos. 5,585,397; 5,916,438 and 5,413,999; U.S. application Ser. No. 10/462,127 filed Jun. 16, 2003 and Published PCT application WO 02/02505, the entire contents of which are hereby incorporated by reference. A derivative of Formula I, or a pharmaceutically-acceptable derivative or salt thereof, may be prepared using any of the available relevant chemical transformations, combined with protection and deprotection as desired or required. Such processes, when used to prepare a derivative of the formula I, or a pharmaceutically-acceptable salt thereof, are illustrated by the following representative examples. The various starting materials are either commercially available or may be obtained by standard procedures of organic chemistry. The preparation of such starting materials is described within the accompanying non-limiting Examples.

Unless otherwise indicated, starting materials are either commercially available, as indicated or are obtained through laboratory synthesis by anyone reasonably familiar with the art.

EXAMPLE 6

This example describes the synthesis of amino acids and amino-acid like compounds of the formula

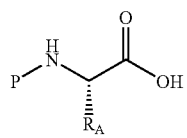

where P is a protecting group and $R_A$ is substituted or unsubstituted aliphatic or aromatic moiety. These compounds were made as described in *J. Org. Chem.* 64: 3322 (1999) and described by Scheme 1.

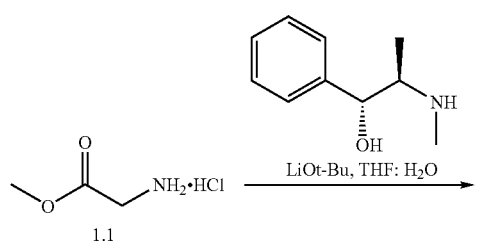

Scheme 1

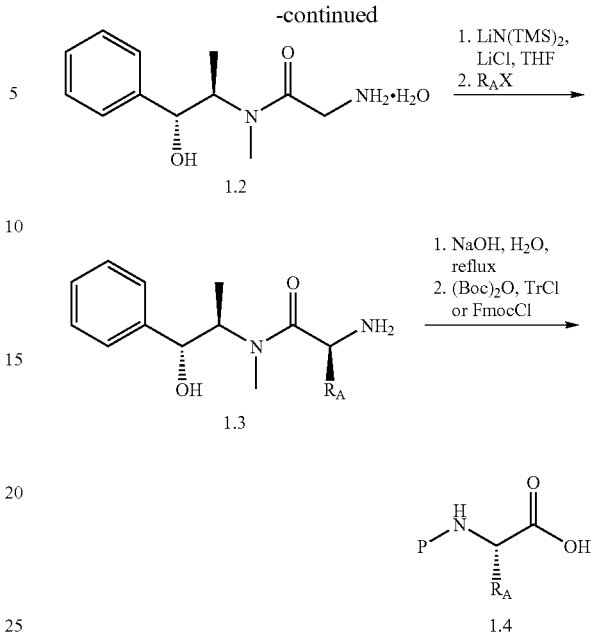

Compound 1.2 was prepared by the treatment of (R,R)-(−)-pseudoephedrine (1 eq) and glycine methyl ester hydrochloride 1.1 (1.3 eq) in tetrahydrofuran (THF) with lithium tert-butoxide (1.4 eq) and worked up with water. Enolization of compound 1.2 in LiCl (3.2 eq) in THF by LHMDS (3.2 eq) and alkylation of $R_A X$ yields compound 1.3. Hydrolysis of compound 1.3 under basic condition (NaOH, H$_2$O, refluxed) followed by protection of the amine gives compound 1.4.

EXAMPLE 7

This example describes the synthesis of compounds of the formula

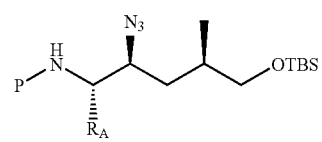

where $R_A$ is as defined in Example 6. These compounds were prepared according to Scheme 2 and the procedure below.

Scheme 2

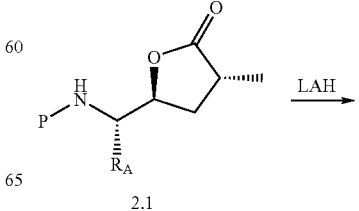

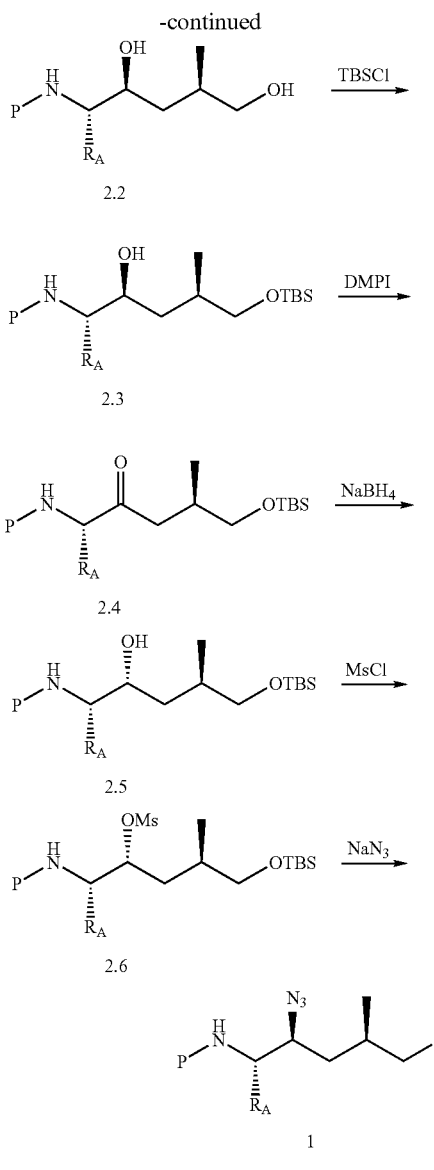

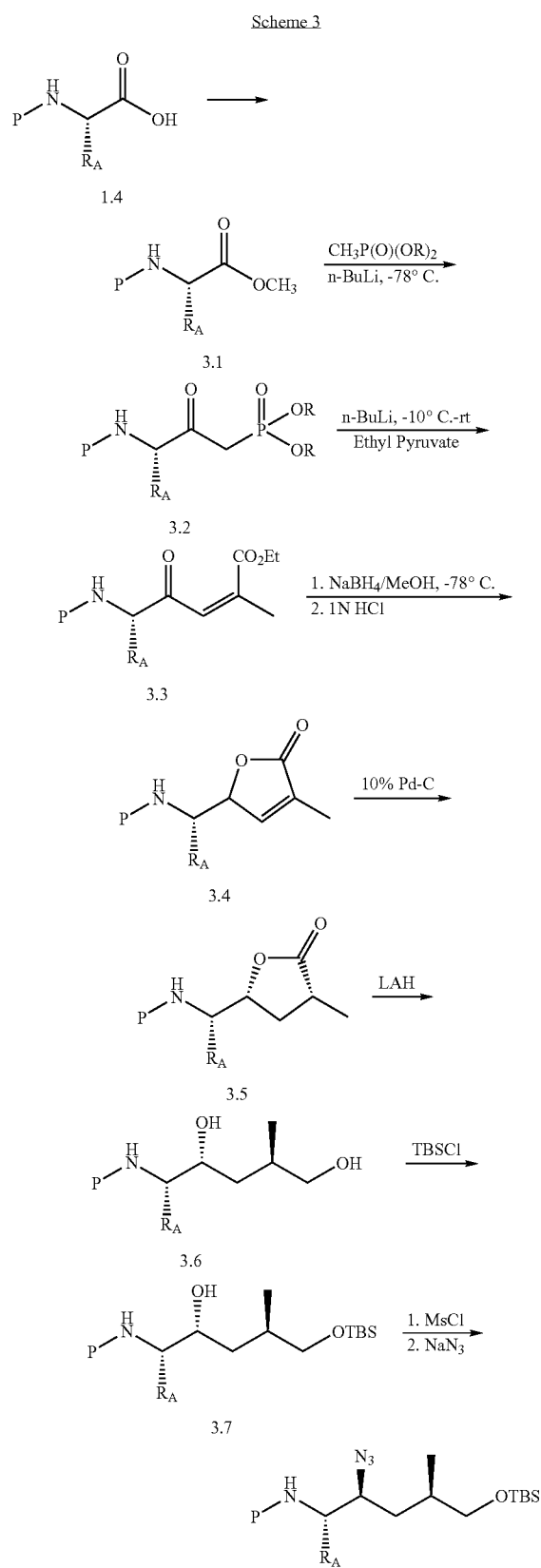

Scheme 3

Compound 2.1 is prepared by the procedure described *J. Am. Chem. Soc.* 122: 3522 (2000) starting with the corresponding N-protected compound made by Example 6 or purchased from commercial sources. Reduction of lactone 2.1 by lithium aluminum hydride ("LAH") yields the corresponding diol 2.2, which was followed by the protection of the primary alcohol by tert-butyl-dimethyl silyl chloride ("TBSCl"; 1 eq), imidazole in $CH_2Cl_2$ to afford compound 2.3. Oxidation of the secondary alcohol by Dess-Martin periodinane to ketone 2.4, and reduction of ketone 2.4 by NaBH4 afford alcohol 2.5. The mesylate 2.6 is obtained by the treatment of alcohol 2.5 with mesyl chloride. The addition of sodium azide to the mesylate 2.6 affords compound 1.

EXAMPLE 8

An alternate procedure to prepare compound 1 is described in Scheme 3 and the procedure below.

Methyl ester 3.1 is prepared by esterfication of the corresponding compound 1.4 (Example 6). The ketophosphonate 3.2 is made from methyl ester 3.1 by Claisen condensation with litho-dimethyl methylphosphonate. The Wadsworth-Emmons reaction of ketophosphonate 3.2 with ethyl pyruvate affords olefin 3.3, which is followed by the reduction by NaBH₄ to afford lactone 3.4. Hydrogenation of lactone 3.4 followed by reduction of LAH yields diol 3.6. The protection of primary alcohol gives TBS ether 3.7. The mesylation of 3.7 follow by the addition of sodium azide to the mesylate affords compound 1.

EXAMPLE 9

Another alternate procedure to prepare compound 1 is described in Scheme 4 and the procedure below.

Scheme 4

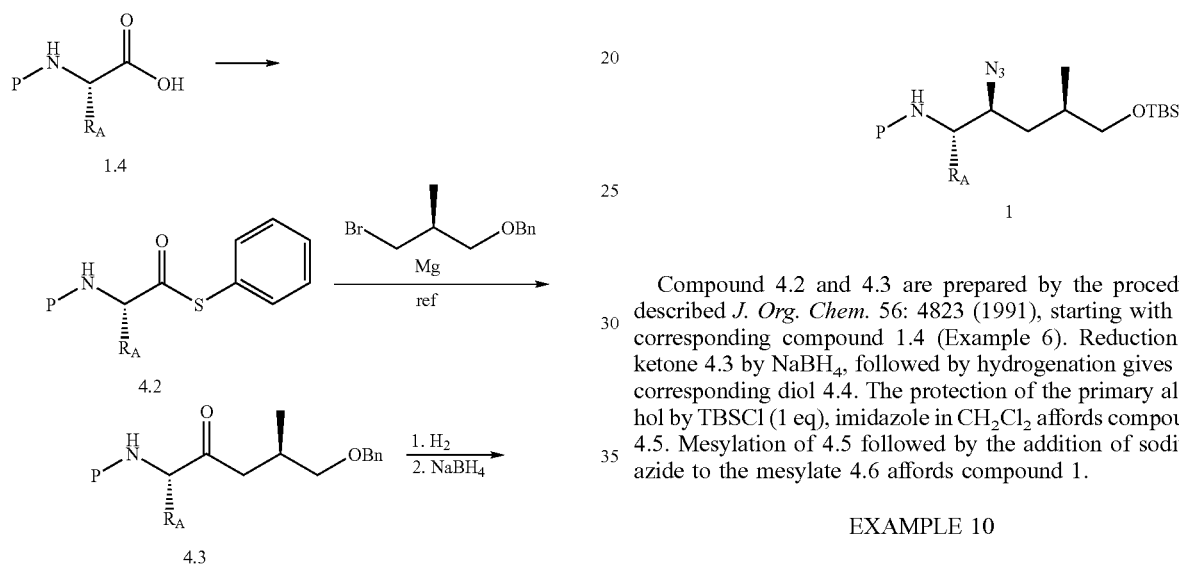

Compound 4.2 and 4.3 are prepared by the procedure described *J. Org. Chem.* 56: 4823 (1991), starting with the corresponding compound 1.4 (Example 6). Reduction of ketone 4.3 by NaBH₄, followed by hydrogenation gives the corresponding diol 4.4. The protection of the primary alcohol by TBSCl (1 eq), imidazole in CH₂Cl₂ affords compound 4.5. Mesylation of 4.5 followed by the addition of sodium azide to the mesylate 4.6 affords compound 1.

EXAMPLE 10

This example describes the synthesis of

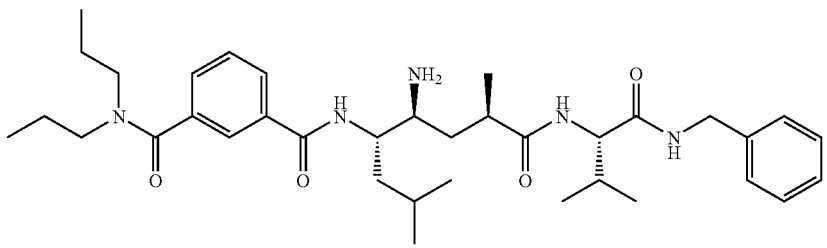

which was prepared according to Scheme 5 and the procedure below.

Scheme 5

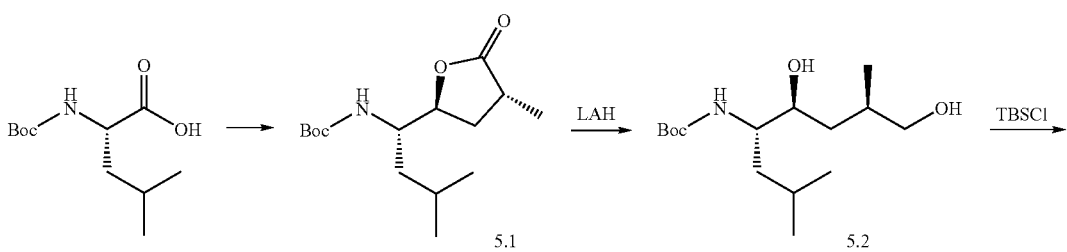

-continued
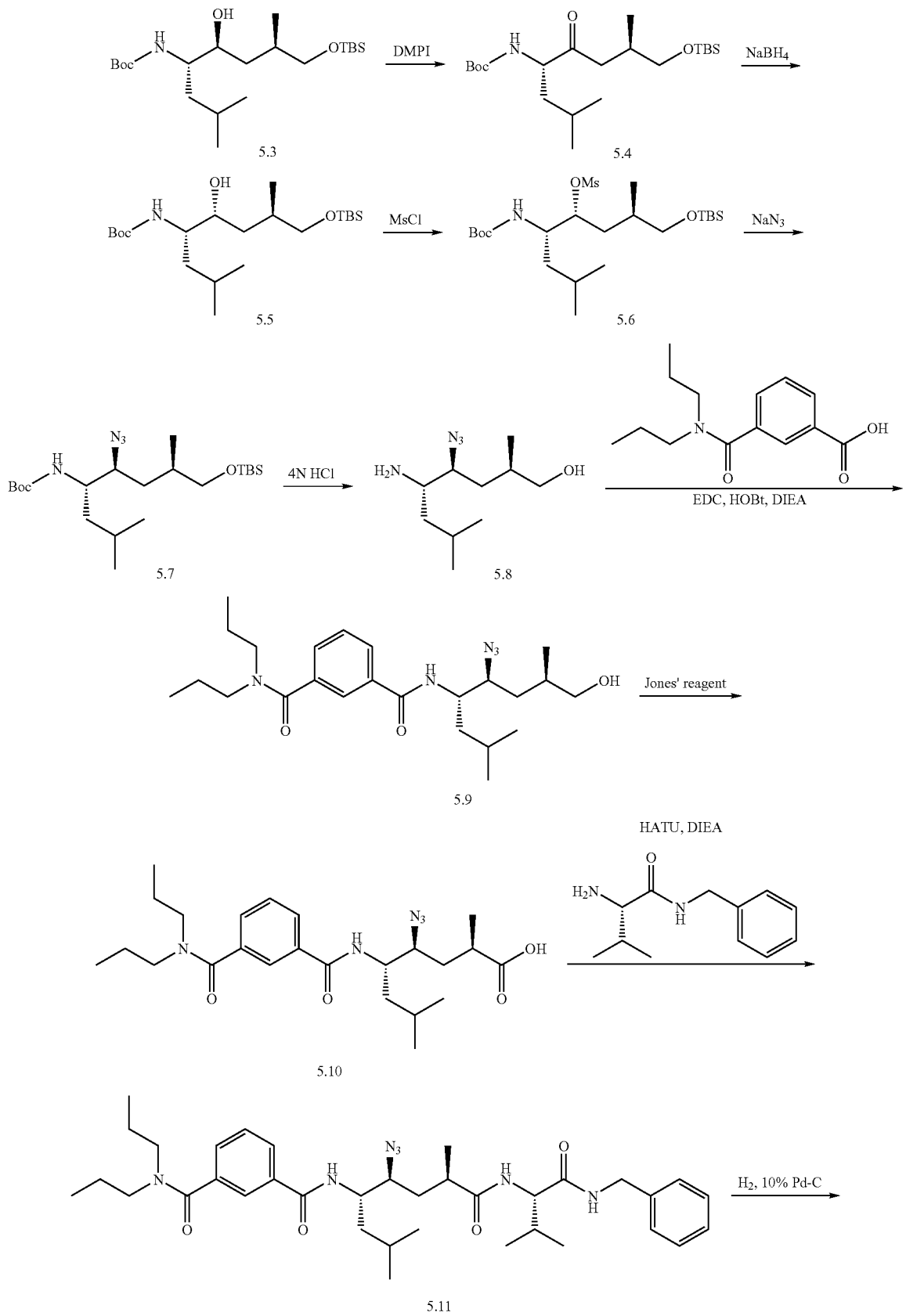

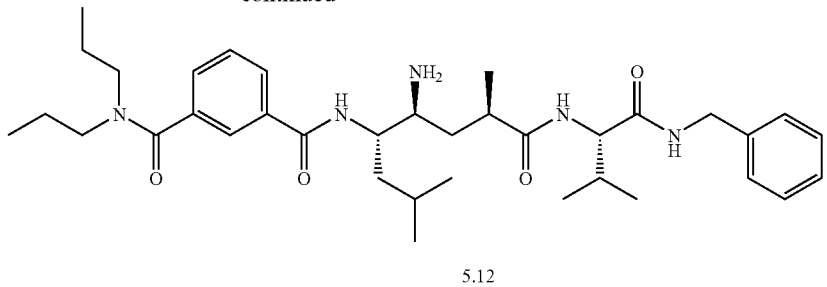

5.12 a) Compound 5.1 ([3-Methyl-1-(4-methyl-5-oxo-tetrahydro-furan-2-yl)-butyl]-carbamic acid tert-butyl ester) was prepared by the procedure described in *J. Am. Chem. Soc.* 122: 3522 (2000).

b) A solution of LiAlH$_4$ (40 mL, 1 M in THF) was added dropwise to 5.7 g of compound 5.1 in 40 ml of THF at 0° C. The reaction solution was warmed to room temperature, stirred for 1.5 hours and cooled to 0° C. A solution of 15% NaHSO$_4$ in water was added dropwise to the reaction mixture until no further precipitate was formed (6 ml of NaHSO$_4$). The reaction mixture was filtered, and concentrated, and the product 5.2 (5.4 g, 93% yield) was used for next reaction without further purification. LCMS: 290 (M+1).

c) TBSCl(2.82 g, 18.8 mmol) was added to the solution of diol 5.2 (5.4 g, 18.8 mmol) and imidazole (2.6 g, 38.2 mmol) in 30 ml of CH$_2$Cl$_2$. After 30 minutes of stirring, the solvent was removed under reduced pressure. The reaction mixture was purified by column chromatography (40% ether/hexanes) to afford 6.5 g (88% yield) of compound 5.3. LCMS: 404(M+1). $^1$H NMR(CDCl$_3$)δ: 4.7(1H, broad s), 3.72(1H, m), 3.6–3.4(3H, m), 3.2(1H, broad s), 1.93 (1H, m), 1.7–1.55 (2H, m), 1.45(10H, m), 1.35–1.25 (2H, m), 0.95–0.85 (18H, m), 0.04 (6H, s).

d) A solution of Dess-Martin periodatate (5.5 g, 13 mmol in 5.5 mL CH$_2$Cl$_2$) was added to a solution of compound 5.3 (3.5 g, 8.68 mmol) in 30 mL of CH$_2$Cl$_2$. After stirring for 15 minutes, the reaction mixture was purified by column (20% ether/hexanes) to afford compound 5.4 (3.2 g, 91%). LCMS: 402(M+1).

e) To a solution of ketone 5.4 (3.2 g, 8.0 mmol) in 50 mL of MeOH, NaBH$_4$ (0.3 g) was added at −78° C. The reaction mixture was stirred for 10 minutes at −30° C., and was concentrated under reduced pressure. The reaction mixture was then extracted by ether (3×50 mL) water (50 mL) and washed with brine (50 mL), and then concentrated to afford compound 5.5 (2.6 g, 81% yield) as 20:1 ratio of syn and anti isomer (determined by $^1$H NMR). LCMS: 404(M+1).

f) Mesyl chloride (1.1 g, 9.7 mmol) was added to the solution of alcohol 5.5 (2.6 g, 6.5 mmol) and triethylamine (2 mL) in chloroform (20 mL) at 0° C. The resulting mixture was stirred for 60 minutes, then purified by column chromatography (20% ether/hexanes) to afford mesylate 5.6 (2.5 g, 80%). LCMS: 482 (M+1).

g) Sodium azide (3.4 g) was added to a solution of mesylate 5.6 (2.5 g) in dimethylformamide ("DMF"; 20 mL). The reaction mixture was stirred for overnight at 75° C. and extracted (ether 5×50 mL/Water 50 mL). The combined organic solution was dried, concentrated and purified by column chromatography (10%, ether/haxanes) to afford desired product 5.7 (1.05 g, 55%), which used as common intermediate LCMS: 429(M+1) $^1$H NMR (CDCl$_3$)δ: 4.43 (1H, broad), 3.77(1H, m), 3.63 (1H, m), 3.49(2H, m), 1.85 (1H, m), 1.7–1.6 (2H, m), 1.45(10H, m), 1.35–1.25 (2H, m), 1.0–0.88(18H, m), 0.05(6H, s) and syn isomer (0.19 g).

h) A solution of 4N HCl in dioxane was added to a solution of compound 5.7 in MeOH. After stirring at room temperature for 60 minutes, the volatiles were removed by reduced pressure to afford compound 5.8, which was without further purification.

i) Method 1: To a mixture of compound 5.8 and N,N-dipropyl-isophthalamic acid in DMF, 1-(3-dimethylaminopropyl)-3-ethylcarbodiimide hydrochloride ("EDC")/1-hydroxybenzotriazole hydrate("HOBt")/diisopropylethylamine ("DIEA") was added. The resulting solution was stirred at room temperature overnight. 1N HCl (2 mL) was added, followed by addition of EtOAc (80 mL). After stirring for 10 minutes, the organic layer was separated, washed with brine and dried over MgSO$_4$. After removal of solvents, the residue was purified by column chromatography to afford compound 5.9. Method 2: To a mixture of compound 5.8 and N,N-dipropyl-isophthalamic acid in CH$_2$Cl$_2$, 2-(1H-azabenzotriazole-1-yl)-1,3,3-tetramethyluronium hexafluorophosphate("HATU")/DIEA was added. The resulting mixture was stirred at room temperature for 2 hours. The volatiles were removed by reduced pressure and purified by column chromatography to afford compound 5.9.

j) Compound 5.9 was oxidized by Jone's reagent, after worked up and purified by column to give acid 5.10. LCMS: 460(M+1) $^1$H NMR(CD$_3$OD)δ: 7.92(1H, d), 7.80 (1H, s), 7.5–7.6(2H, m), 4.33(1H, m), 3.59(1H, m), 3.51 (2H, t), 3.22 (3H, t), 2.70 (1H, m), 1.98(1H, m), 1.80–1.35 (8H, m), 1.20(3H, t), 1.06–0.9(9H, m), 0.75(3H, t).

k) Method 1: To a mixture of compound 5.10 and 2-amino-N-benzyl-3-methyl-butyramide in DMF, EDC/HOBt/DIEA was added. The resulting solution was stirred at room temperature overnight. 1N HCl (2 mL) was added, followed by addition of EtOAc (80 mL). After stirring for 10 minutes, the organic layer was separated, washed with brine and dried over MgSO$_4$. After removal of solvents, the residue was purified by column chromatography to afford compound 5.11. Method 2: To a mixture of compound 5.10 and 2-amino-N-benzyl-3-methyl-butyramide in CH$_2$Cl$_2$, HATU/DIEA was added. The resulting mixture was stirred at room temperature for 2 hours, the volatiles were removed by reduced pressure and purified by column chromatography to afford compound 5.11.

l) Method 1: Compound 5.11 is treated with 1M PhMe$_3$ in THF, and the resulting mixture is stirred for several hours until compound 5.11 is consumed. The reaction mixture is concentrated and 1N HCl is added. The resulting mixture is stirred overnight after which 20% NaOH(aq) is added dropwise until the pH of the solution reaches 12–13.

Method 2: Hydrogenation of compound 5.11 by 10% Pd—C in MeOH yields compound 5.12 which is purified by preparative HPLC.
EXAMPLE 11
This example describes the synthesis of
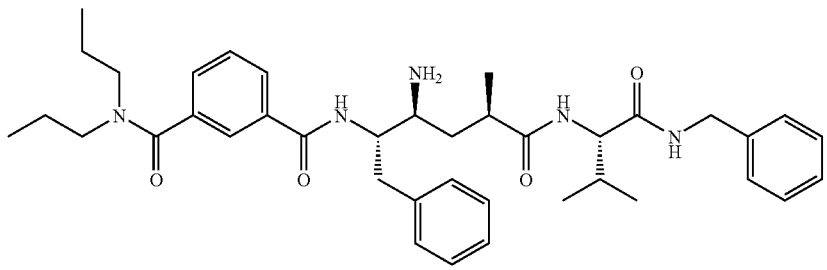
which was prepared according to Scheme 6 and the procedure below.
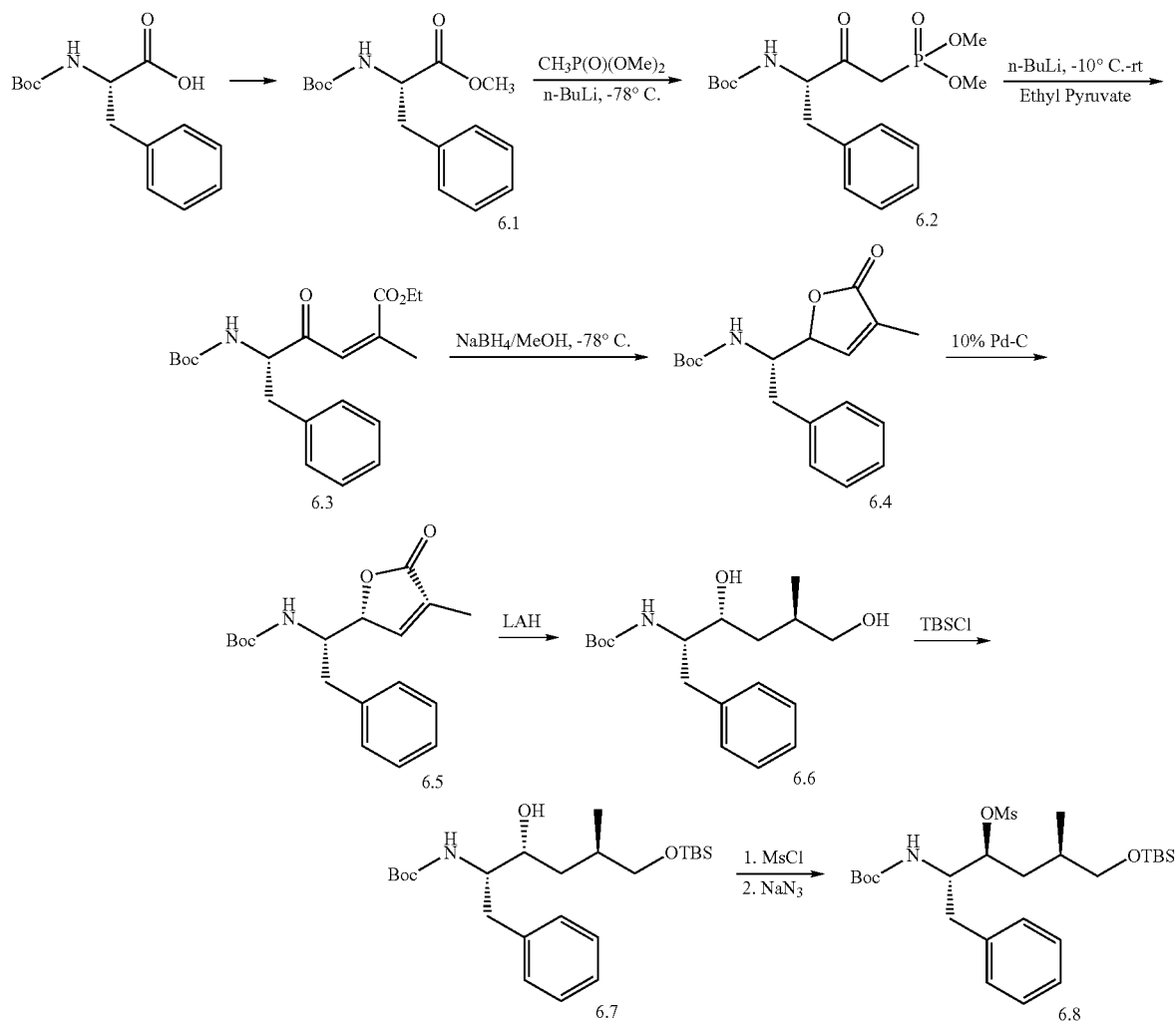

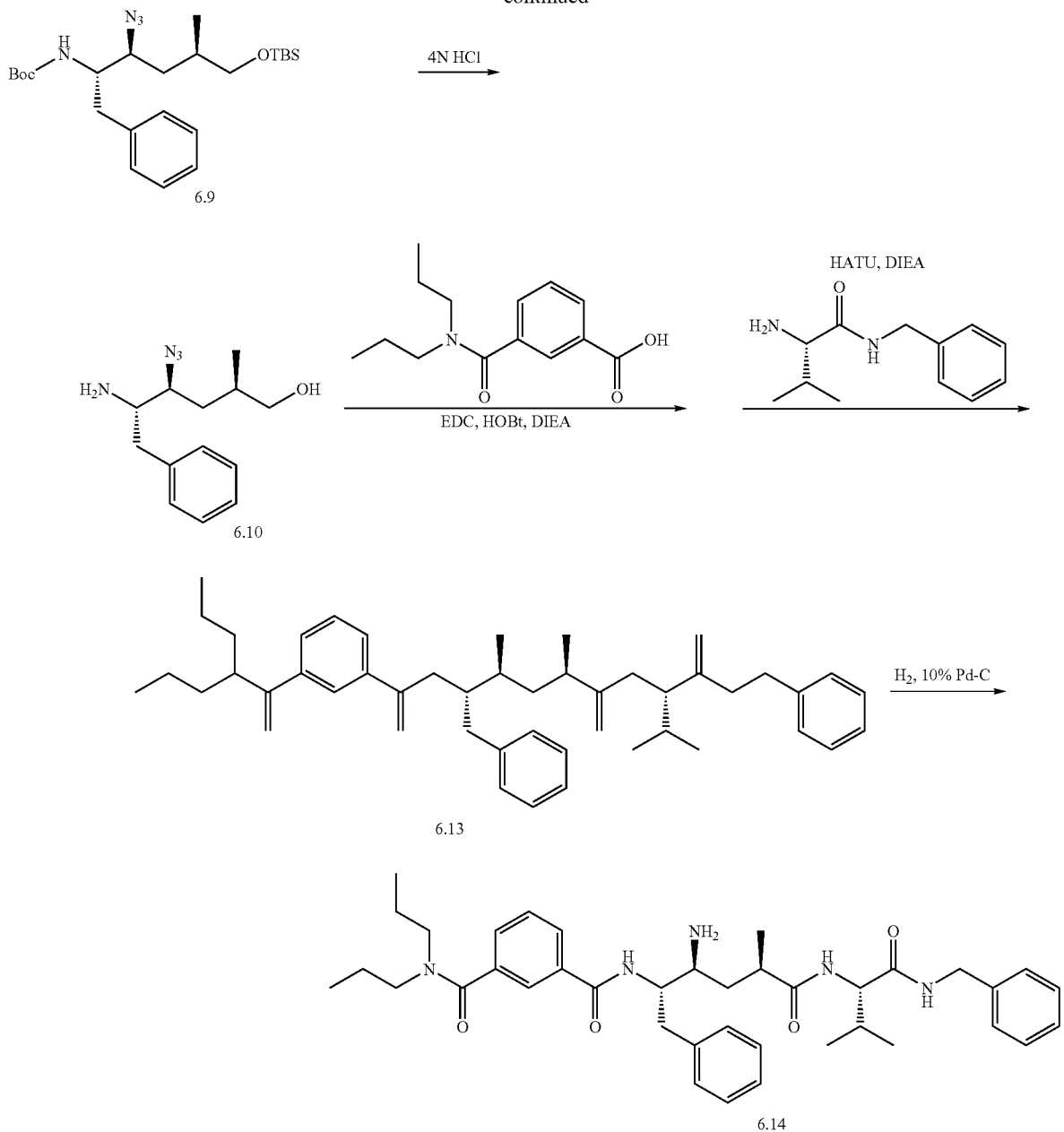

a) A solution of dimethyl methylphosphonate 6.1 (34.1 g, 215.4 mmol) in THF (250 mL) in a nitrogen atmosphere was cooled to −78° C. and then was added 2.0 M solution of butyllithium (107 mL, 215.4 mmol) via canula in 20 minutes. The solution was stirred at −78° C. for 20 minutes, and a THF (150 mL) solution of N-boc-L-phenylalanine methyl ester (10.0 g, 35.8 mmol) was slowly added via dropping funnel. The mixture was stirred at −78° C. for 1 hour. The reaction was then quenched with 10% AcOH (250 mL) and warmed to room temperature. The solution was extracted with EtOAc, and the combined organic extracts were washed with saturated aqueous $NaHCO_3$ and brine and then dried over $MgSO_4$. Solvents were evaporated and the excess dimethyl methylphosphonate was removed by rotary evaporator under high vacuum in a 90° C. water bath. The resulted oily product 6.2 containing 5–10% dimethyl methylphosphonate (shown by $^1H$ NMR) was used without purification. $^1H$ NMR (400 MHz, CDCl3) δ ppm 1.29 (m, 6H) 1.35 (s, 9H) 2.92 (dd, J=14.24, 8.39 Hz, 1H) 3.03 (dd, J=22.38, 13.73 Hz, 1H) 3.22 (m, 2H) 4.10 (m, 4H) 4.55 (d, J=5.59 Hz, 1H) 5.38 (d, J=7.88 Hz, 1H) 7.20 (m, 5H); MS: 422 (MNa+)

b) A solution of the crude phosphonate 6.2 above (16.8 g, ca. 35.8 mmol) in THF (100 mL) in a nitrogen atmosphere was cooled to 0° C. and then was added 1.6 M solution of butyllithium (22.4 mL, 35.8 mmol) via syringe in 10 minutes. The solution was stirred at 0° C. for 30 minutes, and ethyl pyruvate (7.1 mL, 63.2 mmol) was added slowly. Stirring was continued at 0° C. for 1 hour and at room temperature overnight. The reaction was quenched with saturated aqueous NH$_4$Cl (100 mL) and diluted with EtOAc (400 mL). The organic layer was separated, washed with brine and then dried over MgSO$_4$. Solvents were evaporated and the residue was purified by column chromatography (silica gel, Hexane-EtOAc 5:1) to give oily pure product 6.3 (9.0 g, 70% starting from 1). $^1$H NMR (400 MHz, ACETONE-D6) δ ppm 1.24 (t, J=7.12 Hz, 3H) 1.33 (s, 9H) 2.00 (d, J=1.27 Hz, 3H) 2.86 (m, 1H) 3.19 (dd, J=13.99, 5.09 Hz, 1H) 4.18 (q, J=7.12 Hz, 2H) 4.53 (m, 1H) 6.13 (d, J=7.88 Hz, 1H) 6.51 (d, J=1.27 Hz, 1H) 7.22 (m, 5H); MS: 384 (MNa+).

c) To a solution of compound 6.3 (8.4 g, 23.2 mmol) in MeOH (200 mL) cooled to −78° C. was added sodium borohydride (1.7 g, 46.4 mmol). The mixture was stirred and warmed to −15° C. in 3 hours, and then kept at the same temperature overnight. 1N aqueous HCl (100 mL) was added to the cold reaction mixture, and the volatiles were removed by rotary evaporator. The resulted mixture was extracted with EtOAc. The combined extracts were washed with saturated aqueous NaHCO$_3$ and brine and dried over MgSO$_4$. After removal of solvents, the residue was purified by column chromatography (silica gel, Hexane-EtOAc 3:1) to give pure product 6.4 (4.3 g, 58%) and its 5-epimer (3.0 g, 41%) both as white solid. $^1$H NMR (400 MHz, CDCl$_3$) δ ppm 1.36 (s, 9H) 1.88 (s, 3H) 2.80 (d, J=6.61 Hz, 2H) 4.05 (m, 1H) 4.68 (d, J=8.39 Hz, 1H) 4.92 (s, 1H) 6.91 (s, 1H) 7.23 (m, 5H); MS: 340 (Na$^+$).

d) Lactone 6.4 (3.5 g, 11.0 mmol) was dissolved in THF (300 mL), and to this solution 10% Pd/C (350 mg) was added. The mixture was stirred under an atmosphere of H$_2$ (balloon) for 5 hours, followed by filtration and concentration in vacuo, to provide product 6.5 (3.5 g, 99%) as white solid. $^1$H NMR (400 MHz, CDCl$_3$) δ ppm 1.26 (d, J=7.12 Hz, 3H) 1.35 (s, 9H) 1.71 (m, 1H) 2.42 (m, 1H) 2.64 (m, 1H) 2.87 (m, 1H) 3.01 (m, 1H) 3.92 (m, 1H) 4.25 (m, 1H) 4.46 (m, 1H) 7.24 (m, 5H); MS: 342 (MNa+).

e) To a solution of compound 6.5 (3.5 g, 11.0 mmol) in THF (50 mL) cooled to 0° C. was added 0.5 M LiAlH$_4$ in DME (22.0 mL, 11.0 mmol). The mixture was stirred at 0° C. for 0.5 hours and warmed to room temperature. Stirring was continued until TLC indicated the reduction was completed. The mixture was cooled to 0° C. and 1N NaHSO$_4$ (30 mL) was added slowly. After stirring for 30 minutes at room temperature, the mixture was extracted with EtOAc. The combined extracts were washed with saturated aqueous NaHCO$_3$ and brine and dried over MgSO$_4$. After removal of solvents, the residue was purified by column chromatography (silica gel, Hexane-EtOAc 1:1) to yield pure product 6.6 (2.7 g, 76%) as white solid. $^1$H NMR (400 MHz, CDCl$_3$) δ ppm 0.82 (d, J=6.61 Hz, 3H) 1.19 (s, 9H) 1.26 (m, 1H) 1.41 (m, 1H) 1.75 (m, J=15.13, 5.72 Hz, 1H) 2.46 (dd, J=13.61, 10.05 Hz, 1H) 2.93 (dd, J=13.73, 3.05 Hz, 1H) 3.30 (m, 2H) 3.50 (m, 2H) 7.10 (m, 5H); MS: 324 (MH$^+$).

f) To a solution of compound 6.6 (1.0 g, 3.10 mmol) in DCM (15 mL) was added imidazole (422 mg, 6.20 mmol) and TBSCl (578 mg, 3.72 mmol) sequentially at 0° C. After stirring at 0° C. for 1 hour, H$_2$O (10 mL) was added to quench the reaction. The organic layer was separated and the aqueous layer was extracted with DCM. The combined DCM solution was washed with H$_2$O and dried over MgSO$_4$. After removal of solvents, the residue was purified by column chromatography (silica gel, Hexane-EtOAc 3:1) to afford pure product 6.7 (1.34 g, 98%) as white solid. $^1$H NMR (400 MHz, CDCl$_3$) δ ppm 0.08 (s, 6H) 0.87 (d, J=6.87 Hz, 3H) 0.91 (s, 9H) 1.32 (s, 9H) 1.49 (m, J=6.36 Hz, 2H) 1.80 (m, 1H) 2.77 (m, 1H) 2.89 (m, 1H) 3.40 (m, 1H) 3.58 (dd, J=10.05, 4.20 Hz, 1H) 3.68 (s, 1H) 3.81 (s, 1H) 4.18 (m, J=12.33, 4.96 Hz, 1H) 4.78 (d, J=8.65 Hz, 1H) 7.21 (m, 5H); MS: 438 (MH+), 460 (MNa+).

g) To a solution of compound 6.7 (1.2 g, 2.75 mmol) in chloroform (10 mL) was added triethylamine (0.8 mL, 5.5 mmol) and methanesulfonyl chloride ("MsCl"; 0.32 mL, 4.12 mmol) sequentially at 0° C. After stirring at 0° C. for 1 hour, 1 N HCl (5 mL) was added to quench the reaction. The organic layer was separated and the aqueous layer was extracted with CH$_2$Cl$_2$. The combined CH$_2$Cl$_2$ solution was washed with H$_2$O and dried over MgSO$_4$. After removal of solvents, the residue was purified by column chromatography (silica gel, Hexane-EtOAc 3:1) to afford pure product 6.8 (1.34 g, 95%) as colorless oil. $^1$H NMR (400 MHz, CDCl$_3$) δ ppm 0.04 (s, 6H) 0.88 (m, 12H) 1.32 (s, 9H) 1.37 (m, 1H) 1.79 (m, 1H) 1.95 (m, 1H) 2.66 (dd, J=13.22, 10.68 Hz, 1H) 2.90 (dd, J=14.24, 4.83 Hz, 1H) 3.03 (s, 3H) 3.40 (m, 1H) 3.52 (m, 1H) 4.16 (s, 1H) 4.87 (d, J=8.65 Hz, 1H) 4.96 (d, J=9.16 Hz, 1H) 7.23 (m, 5H); MS: 515 (MNa+).

h) Mesylate 6.8 (1.34 g, 2.60 mmol) was dissolved in anhydrous DMF (300 mL). To this stirred solution was added NaN$_3$ (2.50 g, 39.0 mmol). The mixture was heated to 60° C. with an oil bath and stirred at this temperature for 8 hours. The solvent was evaporated in vacuo and then H$_2$O (20 mL) was added to dissolve the solid. The solution was extracted with ether, and the combined extracts were dried over MgSO$_4$. After removal of solvents, the residue was purified by column chromatography (silica gel, Hexane-EtOAc 10:1) to afford pure product 6.9 (0.72 g, 60%) as colorless oil. $^1$H NMR (400 MHz, CDCl$_3$) δ ppm −0.05 (s, 3H) −0.03 (s, 3H) 0.74 (d, J=6.87 Hz, 3H) 0.84 (s, 9H) 1.39 (s, 9H) 1.43 (m, 1H) 1.63 (m, 1H) 1.73 (m, 1H) 2.75 (dd, J=13.61, 8.77 Hz, 1H) 2.92 (m, 1H) 3.37 (m, 2H) 3.53 (t, J=7.12 Hz, 1H) 3.91 (q, J=8.22 Hz, 1H) 4.65 (d, J=9.66 Hz, 1H) 7.25 (m, 5H); MS: 485 (MNa+).

i) Azide 6.9 (109 mg, 0.24 mmol) was treated with 4N HCl in dioxane (5 mL). After stirring for 1 hour, the mixture was concentrated in vacuo and the resulted crude product 6.10 was used for the next step without purification. To a solution of the crude compound 6.10 in DMF (1 mL) was added N,N-dipropyl-isophthalamic acid (58 mg, 0.24 mmol), diisopropylethylamine (0.3 mL, 1.42 mmol), HOBt (54 mg, 0.35 mmol) and EDC (68 mg, 0.35 mmol) sequentially. The mixture was stirred at room temperature for 8 hours. 1N HCl (2 mL) was added, followed by addition of EtOAc (80 mL). After stirring for 10 minutes, the organic layer was separated, washed with brine and dried over MgSO₄. After removal of solvents, the residue was purified by column chromatography (silica gel, DCM-MeOH 19:1) to afford pure product 6.11 (113 mg, 81% starting from 6.9) as colorless oil. ¹H NMR (400 MHz, CD₃OD) δ ppm 0.60 (t, J=7.12 Hz, 3H) 0.81 (d, J=6.61 Hz, 3H) 0.89 (t, J=7.25 Hz, 3H) 1.32 (m, 1H) 1.43 (m, 2H) 1.64 (m, 3H) 1.75 (m, 1H) 2.84 (m, 1H) 2.94 (m, 1H) 3.06 (m, 2H) 3.32 (m, 4H) 3.61 (m, 1H) 4.41 (m, 1H) 7.06 (m, 1H) 7.16 (q, J=7.46 Hz, 4H) 7.40 (m, 2H) 7.55 (s, 1H) 7.67 (d, J=7.12 Hz, 1H); MS: 480 (MH+).

j) To a solution of compound 6.11 (57 mg, 0,12 mmol) in acetone (1 mL) was added Jones' reagent (2.7M, 88 mM, 0,24 mmol). After stirring at room temperature for 20 minutes, iPrOH (40 mL) was added. Stirring was continued for 10 minutes and the reaction mixture was diluted with acetone (20 mL), followed by filtration over celite. The solution was dried (Na2SO4) and concentrated. The resulted crude product 6.12 was used for next step without purification.

k) To a DMF (0.5 mL) solution of the crude acid 6.12 was added 2-amino-N-benzyl-3-methyl-butyramide (20 mg, 0.075 mmol), diisopropylethylamine (0.1 mL, 0.45 mmol) and HATU (38 mg, 0.10 mmol) sequentially. The mixture was stirred at room temperature for 2 hours, and then purified by HPLC to provide pure product 6.13 (26 mg, 76% starting from compound 6.11) as white solid. ¹H NMR (400 MHz, METHANOL-D) δ ppm 0.57 (t, J=7.25 Hz, 3H) 0.76 (m, 6H) 0.87 (t, J=7.25 Hz, 4H) 0.98 (d, J=6.61 Hz, 3H) 1.41 (m, 3H) 1.59 (m, 2H) 1.90 (m, 2H) 2.66 (m, 1H) 2.79 (dd, J=13.73, 9.66 Hz, 1H) 2.94 (dd, J=13.99, 5.60 Hz, 1H) 3.03 (m, 2H) 3.22 (s, 1H) 3.36 (m, 3H) 3.99 (d, J=7.63 Hz, 1H) 4.25 (s, 2H) 4.40 (s, 1H) 7.10 (m, 10H) 7.38 (q, J=7.97 Hz, 2H) 7.53 (s, 1H) 7.65 (d, J=6.87 Hz, 1H); MS: 682 (MH+).

l) To a solution of compound 6.13 (19 mg, 0.0279 mmol) in MeOH (5 mL) 10% Pd—C (6 mg) was added. The mixture was stirred under an atmosphere of H₂ for 30 minutes, followed by filtration and concentration. The resulting crude product was purified by preparative TLC to afford pure product 6.14 (16 mg, 88%) as white solid. ¹H NMR (400 MHz, METHANOL-D) δ ppm 0.61 (t, J=7.25 Hz, 3H) 0.76 (d, J=6.61 Hz, 6H) 0.88 (m, 4H) 0.98 (d, J=6.87 Hz, 3H) 1.28 (m, 1H) 1.42 (m, 2H) 1.62 (m, 2H) 1.79 (m, 1H) 1.91 (m, 1H) 2.65 (dd, J=14.62, 6.23 Hz, 1H) 2.75 (m, 2H) 2.91 (m, 1H) 3.07 (m, 2H) 3.37 (m, 2H) 4.00 (d, J=7.38 Hz, 1H) 4.27 (m, 2H) 7.05 (t, J=7.12 Hz, 1H) 7.16 (m, 9H) 7.40 (m, 2H) 7.58 (s, 1H) 7.71 (d, J=7.38 Hz, 1H); MS: 656 (MH+).

EXAMPLE 12

The example describes the synthesis of compounds of the formula

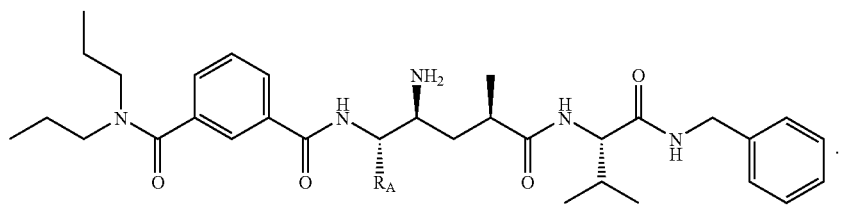

These compounds are prepared according the procedure of Example 10 or Example 11 except for using other amino acids and amino acid like compound of the formula

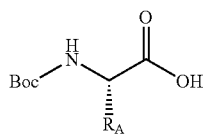

as a reagent instead of

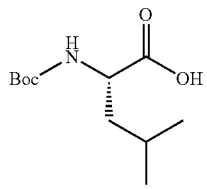

(Example 10) or

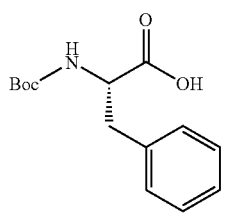

(Example 11). Illustrative examples of amino acids and amino acid like compounds and their corresponding products are shown in Table 1.

TABLE 1

| Reagent | Product |
|---|---|
| Boc-NH-CH(CH2-(3,5-difluorophenyl))-COOH | dipropylamide-isophthaloyl-NH-CH(CH2-(3,5-difluorophenyl))-CH(NH2)-CH(CH3)-CO-NH-CH(iPr)-CO-NH-CH2-Ph |
| Boc-NH-CH(CH2-(4-fluorophenyl))-COOH | dipropylamide-isophthaloyl-NH-CH(CH2-(4-fluorophenyl))-CH(NH2)-CH(CH3)-CO-NH-CH(iPr)-CO-NH-CH2-Ph |
| Boc-NH-CH(CH2-(3-fluorophenyl))-COOH | dipropylamide-isophthaloyl-NH-CH(CH2-(3-fluorophenyl))-CH(NH2)-CH(CH3)-CO-NH-CH(iPr)-CO-NH-CH2-Ph |
| Boc-NH-CH(CH2-(2-fluorophenyl))-COOH | dipropylamide-isophthaloyl-NH-CH(CH2-(2-fluorophenyl))-CH(NH2)-CH(CH3)-CO-NH-CH(iPr)-CO-NH-CH2-Ph |
| Boc-NH-CH(CH2-(3,4-difluorophenyl))-COOH | dipropylamide-isophthaloyl-NH-CH(CH2-(3,4-difluorophenyl))-CH(NH2)-CH(CH3)-CO-NH-CH(iPr)-CO-NH-CH2-Ph |

TABLE 1-continued

| Reagent | Product |
| --- | --- |
| (structure: Boc-NH-CH(CH2-2,4-difluorophenyl)-COOH) | (structure with 2,4-difluorobenzyl side chain) |
| (structure: Boc-NH-CH(CH2-2,3-difluorophenyl)-COOH) | (structure with 2,3-difluorobenzyl side chain) |
| (structure: Boc-NH-CH(CH2-4-methylphenyl)-COOH) | (structure with 4-methylbenzyl side chain) |
| (structure: Boc-NH-CH(CH2-3-methylphenyl)-COOH) | (structure with 3-methylbenzyl side chain) |
| (structure: Boc-NH-CH(CH2-4-methoxyphenyl)-COOH) | (structure with 4-methoxybenzyl side chain) |

TABLE 1-continued

| Reagent | Product |
|---|---|
| 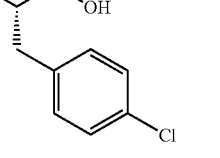 | 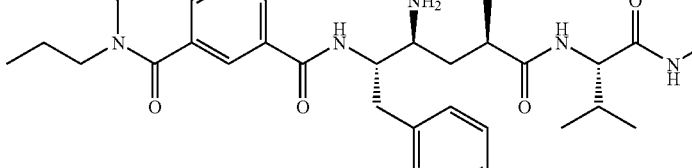 |
| 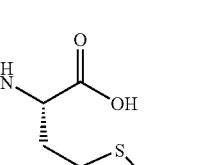 | 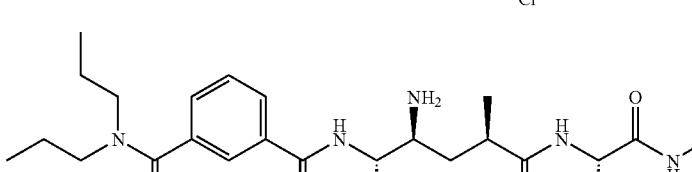 |
| 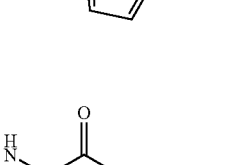 | 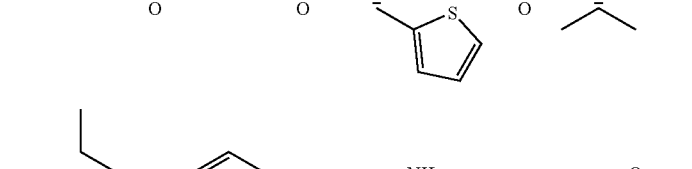 |
| 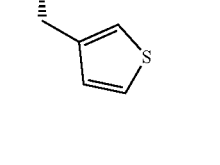 | 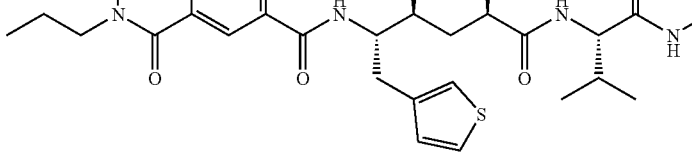 |

EXAMPLE 13

This example describes the synthesis of

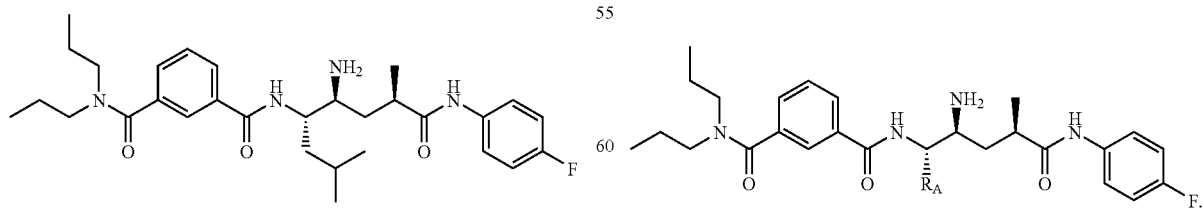

which was prepared according to Example 10 except for using 4-fluoroaniline instead of 2-amino-N-benzyl-3-methyl-butyramide in step k. MS (M+1) 527.

EXAMPLE 14

The example describes the synthesis of compounds of the formula

These compounds are prepared according to Example 13 except for using amino acids and amino acid-like compounds of the formula

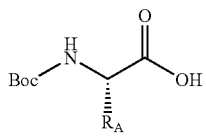

instead of

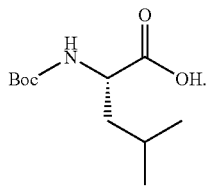

Exemplary amino acids and amino acid-like compounds are shown in Table 1.

EXAMPLE 15

This example describes the synthesis of

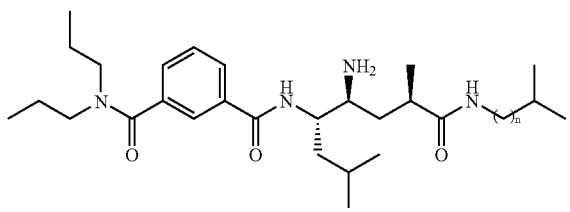

which is prepared according to Example 10 except for using isopropylamine instead of 2-amino-N-benzyl-3-methyl-butyramide in step k when n=0 and for using isobutylamine instead of 2-amino-N-benzyl-3-methyl-butyramide in step k when n=1.

EXAMPLE 16

The example describes the synthesis of compounds of the formula

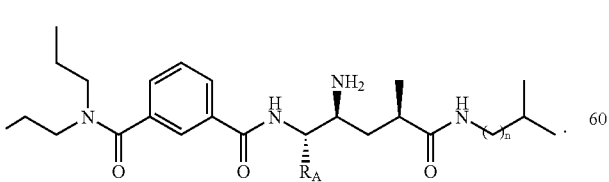

These compounds are prepared according to Example 15 except for using amino acids and amino acid-like compounds of the formula

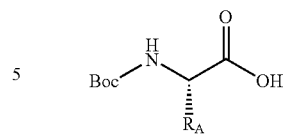

instead of

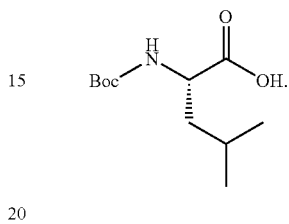

EXAMPLE 17

This example describes the synthesis of

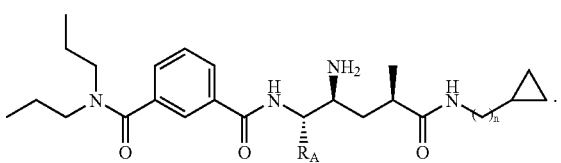

which was prepared according to Example 10 except for using cyclopropylamine instead of 2-amino-N-benzyl-3-methyl-butyramide in step k when n=0 and cyclopropyl-methyl amine instead 2-amino-N-benzyl-3-methyl-butyramide in step k when n=1.

Example 18

This example describes the synthesis of compounds of the formula

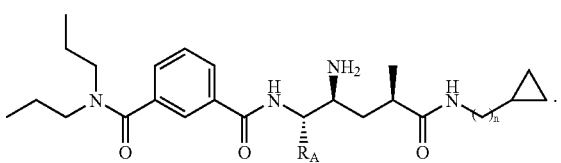

These compounds are prepared according to Example 17 except for using amino acids and amino acid-like compounds of the formula

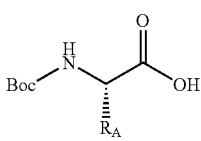

instead of

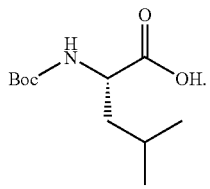

Example 19

This example describes the synthesis of

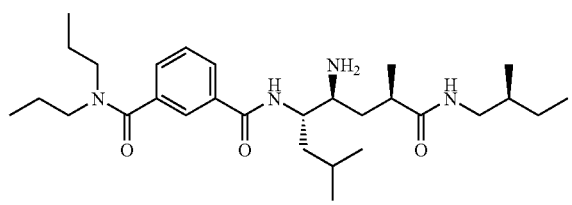

which was prepared according to Example 10 except for 2-methyl-butylamine instead of 2-amino-N-benzyl-3-methyl-butyramide in step k.

EXAMPLE 20

The example describes the synthesis of compounds of the formula

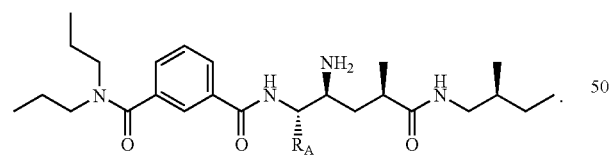

These compounds are prepared according to Example 19 except for using amino acids and amino acid-like compounds of the formula

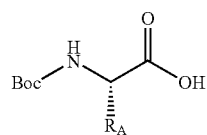

instead of

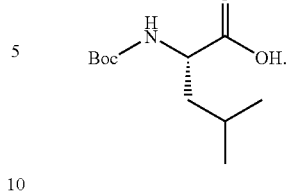

EXAMPLE 21

This example describes the synthesis of

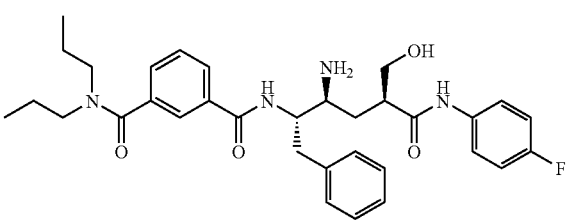

which is prepared according to Example 11 except for using 3-benzyloxy-2-oxo propanic acid methyl ester, which is prepared from 3-hydroxyl-2-oxo propanic acid instead of ethyl pyruvate in the step b, and 4-fluoroaniline instead of 2-amino-N-benzyl-3-methyl-butyramine in the step j.

EXAMPLE 22

This example describes the synthesis of compounds of the formula

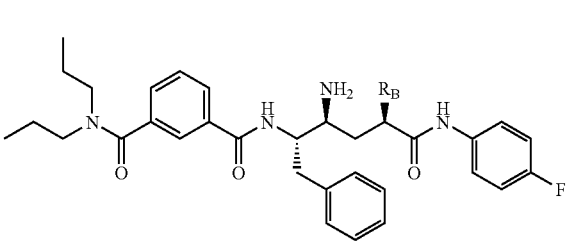

wherein $R_B$ is a substituted or unsubstituted aliphatic or aromatic moiety. These compounds are prepared according to Example 21 except for using 2-oxo-acid esters of the formula $ROC(=O)C(=O)R_B$ (wherein R is lower alkyl and $R_B$ is as defined above) instead of 3-benzyloxy-2-oxo-propanic acid methyl ester. Exemplary esters and their corresponding products are shown in Table 2.

TABLE 2

| Ester | Product |
|---|---|
| 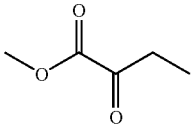 | 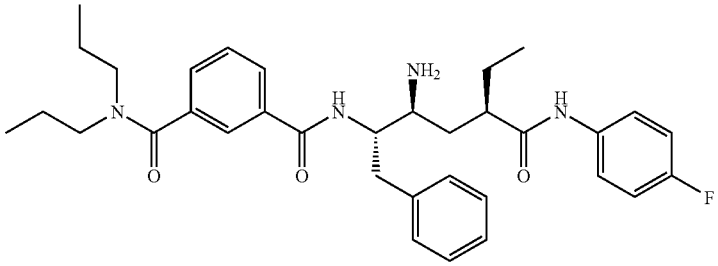 |
| 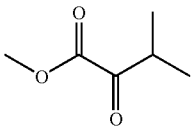 | 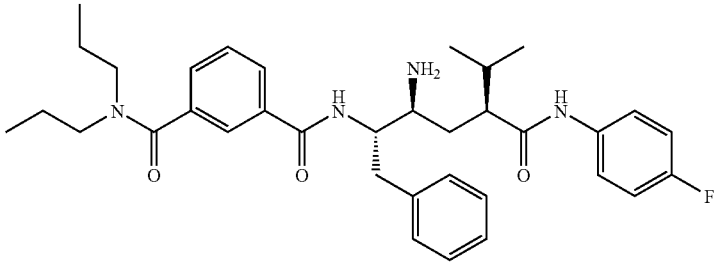 |
| 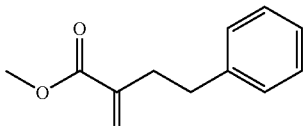 | 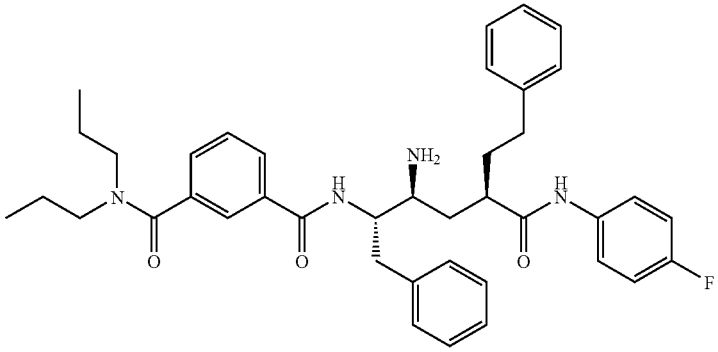 |

EXAMPLE 23

The example describes the synthesis of compounds of the formula

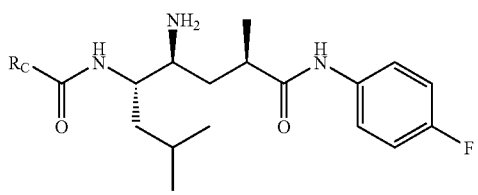

where $R_C$ is substituted or unsubstituted aliphatic or aromatic moiety. These compounds are prepared according to Example 10 except for using acids of the formula $R_C$COOH as a reagent instead of N,N-dipropyl-isophthalamic acid in step i and using 4-fluoroanaline instead of 2-amino-N-benzyl-3-methyl-butyramide in step k. Illustrative examples of acids and their corresponding products are shown in Table 3.

TABLE 3
| R<sub>C</sub>COOH | Product |
|---|---|
| 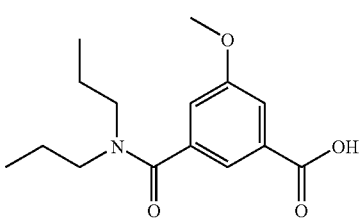 | 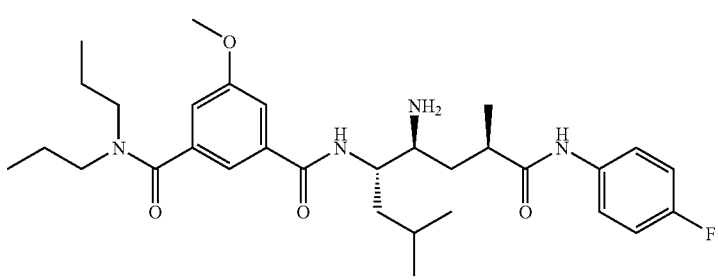 |
| 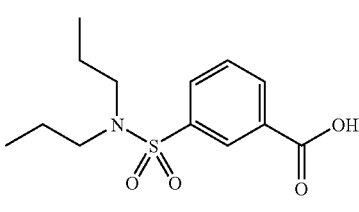 | 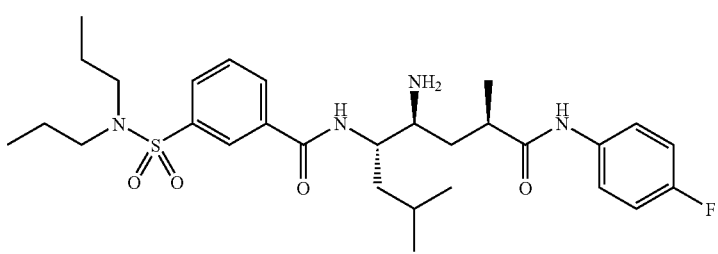 |
| 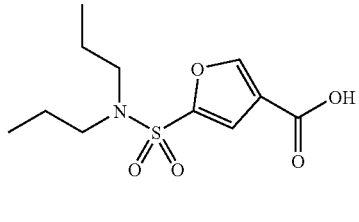 | 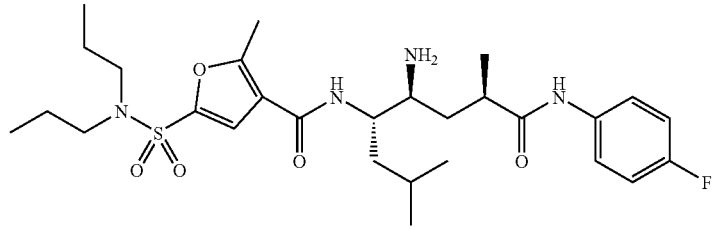 |
| 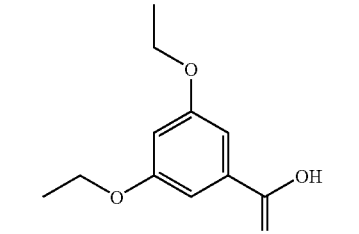 | 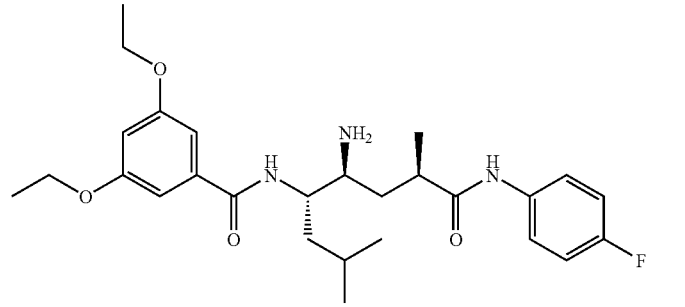 |
| 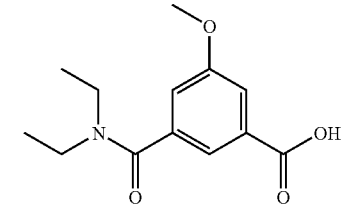 | 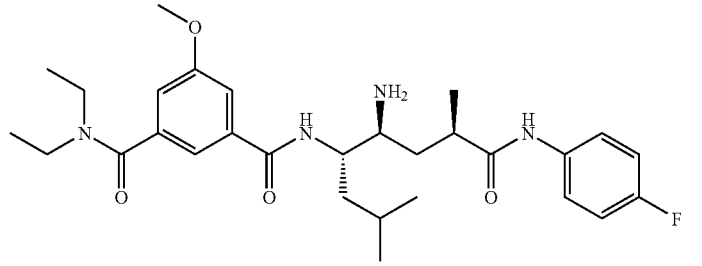 |

TABLE 3-continued

| R$_C$COOH | Product |
|---|---|
| 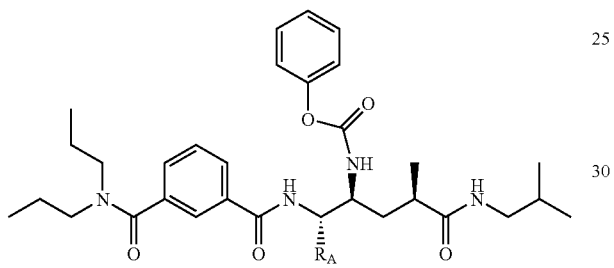 | |

EXAMPLE 24

This example describes the synthesis of the compounds of the formula which are prepared according to Scheme 7 and the procedure below.

The Compounds-7.1 are prepared according to Example 16. These compounds are then reacted with phenyl chloroformate and DIEA to yield compounds 7.2. In certain embodiments, compounds 7.2 can be used as prodrug forms of their corresponding compounds 7.1.

EXAMPLE 25

This example describes the synthesis of compounds of the formula

Scheme 7

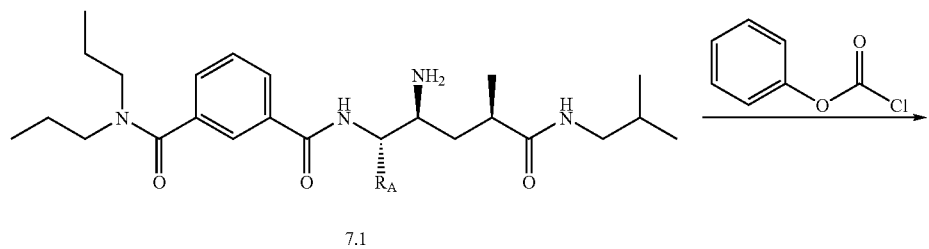

7.1

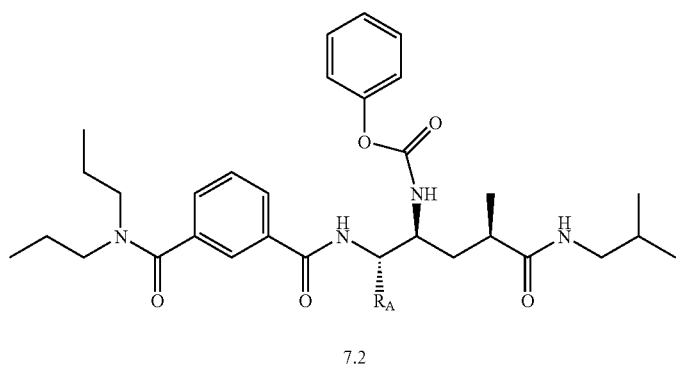

7.2

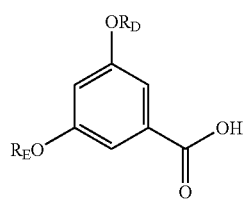

wherein $R_D$ and $R_E$ are each independently substituted or unsubstituted aliphatic or aromatic moieties. These compounds are prepared according to Scheme 8 and the procedure below.

Scheme 8

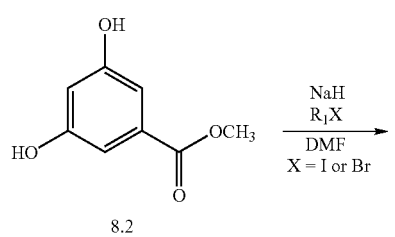

8.2

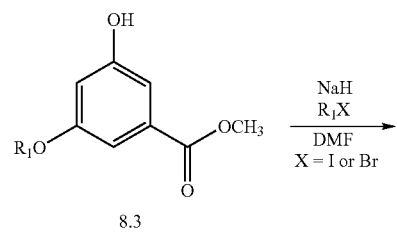

8.3

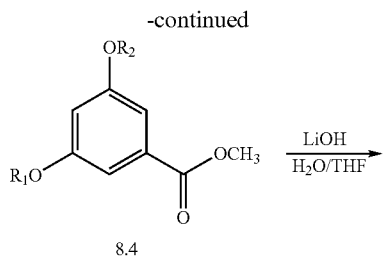

8.4

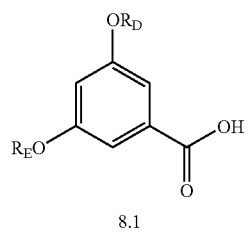

8.1

Compound 8.2 is treated with NaH in DMF, and halide $R_DX$ (1 eq) is added to the reaction mixture to yield aryl ether 8.3. Compound 8.3 is then treated with NaH in DMF, and halide $R_EX$ (1 eq) is added. The reaction mixture is hydrolized (LiOH, H2O/THF) to give acid 8.1. Compounds 8.1, acids of the formula $R_C$COOH, are used to make additional compounds of the invention. Table 4 shows exemplary compounds 8.1's.

TABLE 4

| $R_DX$ | $R_EX$ | $R_C$COOH |
|---|---|---|
| ethyl-I | ethyl-I | 3,5-diethoxybenzoic acid |
| isopropyl-I | isopropyl-I | 3,5-diisopropoxybenzoic acid |

TABLE 4-continued

| R_DX | R_EX | R_CCOOH |
|---|---|---|
| isopropyl-I | ethyl-I | 3-ethoxy-5-isopropoxybenzoic acid |
| sec-butyl-Br | CH₃I | 3-methoxy-5-(pentan-3-yloxy)benzoic acid |
| sec-butyl-Br | ethyl-I | 3-ethoxy-5-(pentan-3-yloxy)benzoic acid |
| sec-butyl-Br | isopropyl-I | 3-isopropoxy-5-(pentan-3-yloxy)benzoic acid |
| sec-butyl-Br | sec-butyl-Br | 3,5-bis(pentan-3-yloxy)benzoic acid |
| sec-butyl-Br | cyclopropyl-Br | 3-cyclopropoxy-5-(pentan-3-yloxy)benzoic acid |

TABLE 4-continued
| R_DX | R_EX | R_CCOOH |
|---|---|---|
| 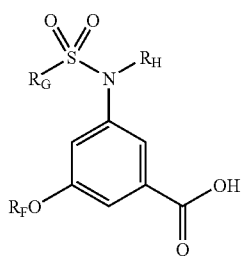 | | |
EXAMPLE 26
This example describes the synthesis of compounds of the formula
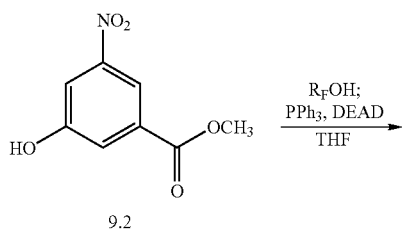
wherein $R_F$, $R_G$, and $R_H$ are each independently substituted or unsubstituted aliphatic or aromatic. These compounds are prepared according to Scheme 9 and the procedure below.
Scheme 9
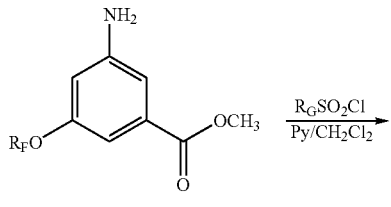
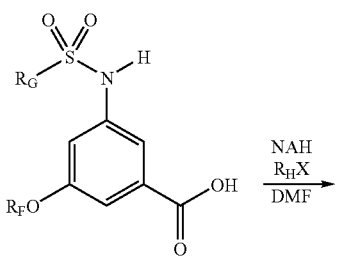
9.2
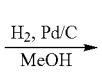
9.3
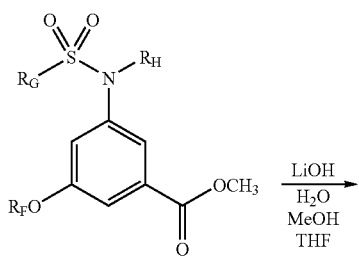
9.6

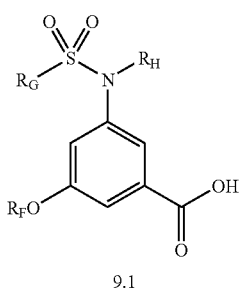

9.1

Mitsunobu reaction of compound 9.2 and the corresponding alcohol gives aryl ether 9.3. Hydrogenation of 9.3 reduces nitro group to aniline 9.4, which is followed by treatment of sulfonyl chloride to give the corresponding sulfonamide 9.5. Alkylation of sulfonamide 9.5 with halide (NaH, $R_HX$, 1 eq) gives 9.6, followed by basic hydrolysis (LiOH, H2O/THF/MeOH) to give acid 9.1. Compounds 9.1, acids of the formula $R_C$COOH, are used to make additional compounds of the invention. Table 5 shows exemplary compounds 9.1's.

TABLE 5

TABLE 5-continued

| R_FX | R_GSO_2Cl | R_HX | R_CCOOH |
|---|---|---|---|
| ethyl-I | MeSO_2Cl | CH_3I | 3-(N-methyl-methylsulfonamido)-5-ethoxybenzoic acid |
| cyclopropyl-Br | MeSO_2Cl | CH_3I | 3-(N-methyl-methylsulfonamido)-5-cyclopropoxybenzoic acid |
| cyclopropylmethyl-Br | MeSO_2Cl | CH_3I | 3-(N-methyl-methylsulfonamido)-5-(cyclopropylmethoxy)benzoic acid |
| 3-pentyl-Br | MeSO_2Cl | CH_3I | 3-(N-methyl-methylsulfonamido)-5-(pentan-3-yloxy)benzoic acid |
| isopropyl-I | MeSO_2Cl | CH_3I | 3-(N-methyl-methylsulfonamido)-5-isopropoxybenzoic acid |
| n-propyl-Br | MeSO_2Cl | CH_3I | 3-(N-methyl-methylsulfonamido)-5-propoxybenzoic acid |

TABLE 5-continued

| R_FX | R_GSO_2Cl | R_HX | R_C-COOH |
|---|---|---|---|
| (methylcyclopropyl-CH2-X) | PhSO_2Cl | —I | 3-[N-methyl(phenylsulfonyl)amino]-5-(methylcyclopropylmethoxy)benzoic acid |
| (methylcyclopropyl-CH2-X) | PhSO_2Cl | ethyl-I | 3-[N-ethyl(phenylsulfonyl)amino]-5-(methylcyclopropylmethoxy)benzoic acid |
| CH_3I | PhSO_2Cl | CH_3I | 3-[N-methyl(phenylsulfonyl)amino]-5-methoxybenzoic acid |
| ethyl-I | PhSO_2Cl | CH_3I | 3-[N-methyl(phenylsulfonyl)amino]-5-ethoxybenzoic acid |
| cyclopropyl-Br | PhSO_2Cl | CH_3I | 3-[N-methyl(phenylsulfonyl)amino]-5-cyclopropoxybenzoic acid |
| cyclopropyl-CH2-Br | PhSO_2Cl | CH_3I | 3-[N-methyl(phenylsulfonyl)amino]-5-(cyclopropylmethoxy)benzoic acid |

TABLE 5-continued

| $R_F$X | $R_G$SO$_2$Cl | $R_H$X | $R_C$COOH |
|---|---|---|---|
| ![sec-butyl-Br] | PhSO$_2$Cl | CH$_3$I | [structure] |
| ![iPr-I] | PhSO$_2$Cl | CH$_3$I | [structure] |
| ![propyl-Br] | PhSO$_2$Cl | CH$_3$I | [structure] |

EXAMPLE 27

This example describes the synthesis of compounds of the formula wherein $R_F$ is substituted or unsubstituted aliphatic or aromatic moiety. These compounds are prepared according to Scheme 10 and the procedure below.

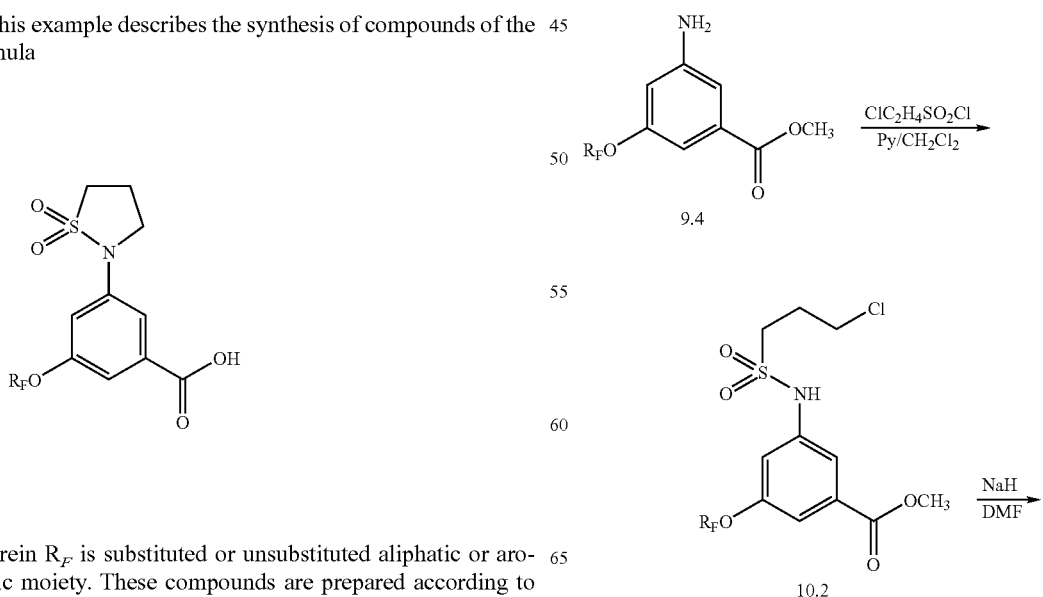

-continued

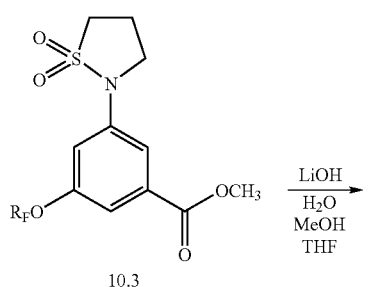
10.3

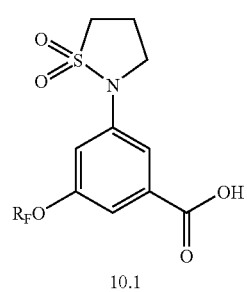
10.1

Aniline 9.4 (Example 35) is treated which sulfonyl chloride to yield sulfonamide 10.2, which is followed by the treatment of NaH to afford cyclic sulfonamide 10.3. Basic hydrolysis (LiOH, H₂O/THF/MeOH) of compound 10.3 gives acid 10.1. Compounds 10.1, acids of the formula R$_C$COOH, are used to make additional compounds of the invention. Table 6 shows exemplary compounds 10.1's.

TABLE 6

| R$_F$ | R$_C$COOH |
|---|---|
|  | 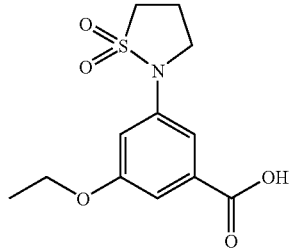 |
|  | 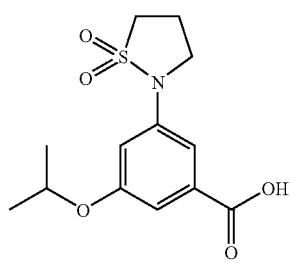 |

TABLE 6-continued

| R$_F$ | R$_C$COOH |
|---|---|
| — | 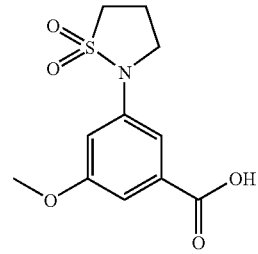 |
| 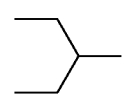 | 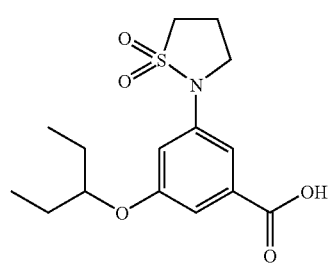 |
|  | 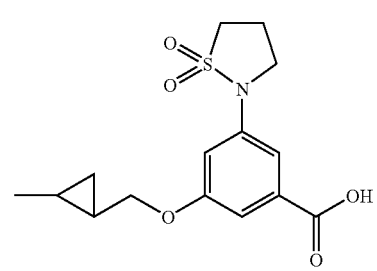 |
|  | 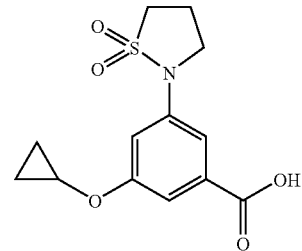 |
| 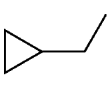 | 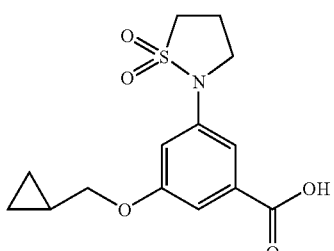 |
|  | 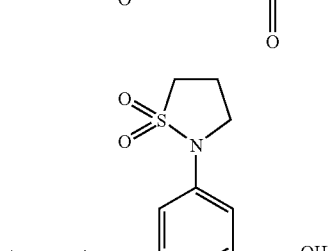 |

EXAMPLE 28

This example describes the preparation of compounds of the formula

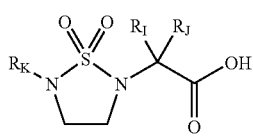

5

10 wherein $R_I$, $R_J$, and $R_K$ are each independently substituted or unsubstituted aliphatic or aromatic moiety. These compounds are prepared according to Scheme 11 and the procedure below.

20

Scheme 11

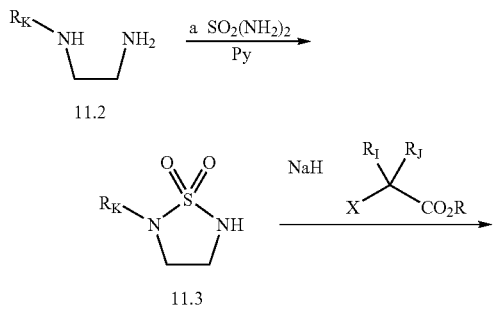

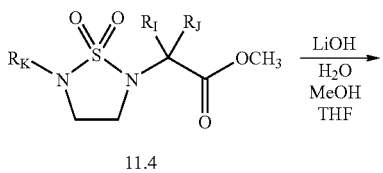

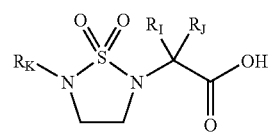

11.1

The treatment of diamine 11.2 with sulfamine a under refluxing pyridine affords sulfamine 11.3, which is followed by alkylation of a-halo alkyl ester to give compound 11.4. Basic hydrolysis (LiOH, $H_2O$/THF/MeOH) of ester gives acid 11.1. Compounds 11.1, acids of the formula $R_C$COOH, are used to make additional compounds of the invention. Table 7 shows exemplary compounds 11.1's.

TABLE 7

| $XCR_IR_JCOOCH_3$ | $R_KNHCH_2CH_2NH_2$ | $R_CCOOH$ |
|---|---|---|
| Br~CO₂Me | ~NH~NH₂ (butyl) | structure with butyl-N ring-CH₂COOH |
| Br~CO₂Me | ~NH~NH₂ (propyl) | structure with propyl-N ring-CH₂COOH |
| Br~CO₂Me | ~NH~NH₂ (isobutyl) | structure with isobutyl-N ring-CH₂COOH |
| Br~CO₂Me | ~NH~NH₂ (cyclopropylmethyl) | structure with cyclopropylmethyl-N ring-CH₂COOH |

TABLE 7-continued

| XCR$_I$R$_J$COOCH$_3$ | R$_K$NHCH$_2$CH$_2$NH$_2$ | R$_C$COOH |
|---|---|---|

TABLE 7-continued

| XCR₁R₁COOCH₃ | R_KNHCH₂CH₂NH₂ | R_CCOOH |
|---|---|---|

TABLE 7-continued

| XCR$_I$R$_J$COOCH$_3$ | R$_K$NHCH$_2$CH$_2$NH$_2$ | R$_C$COOH |
|---|---|---|

TABLE 7-continued
| XCR$_I$R$_J$COOCH$_3$ | R$_K$NHCH$_2$CH$_2$NH$_2$ | R$_C$COOH |
|---|---|---|
| 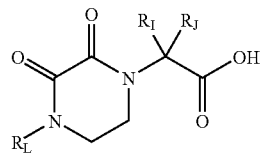 | | |
EXAMPLE 29
This example describes the synthesis of compounds of the formula
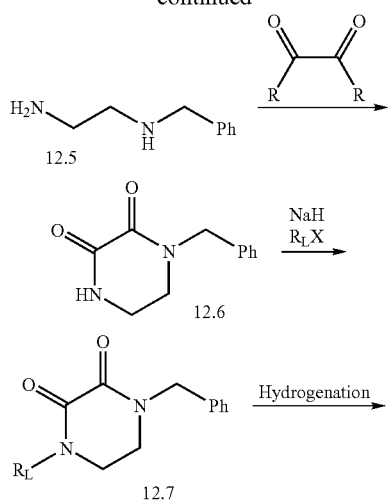
wherein R$_I$, R$_J$, and R$_L$ are each independently substituted or unsubstituted aliphatic or aromatic moiety. These compounds are prepared according to Scheme 12 and the procedure below.
Scheme 12
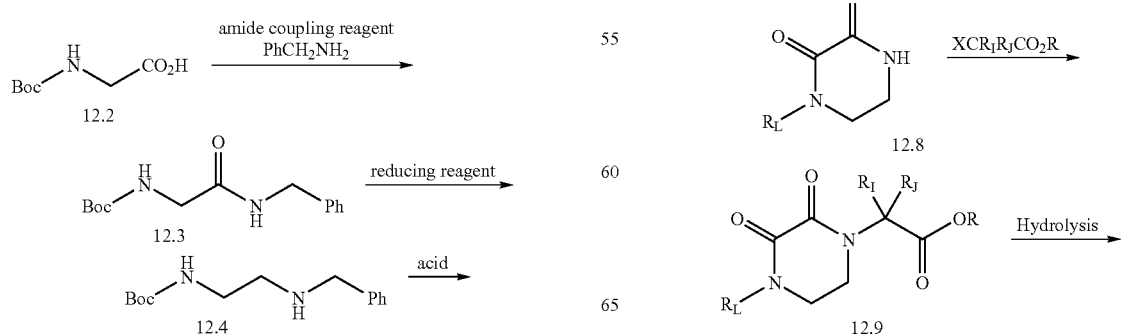

-continued

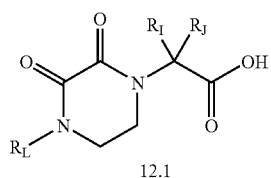

12.1

Amino acid 12.2 is treated with benzyl amine and a coupling reagent such as HATU, to give 12.3. Compound 12.3 is reduced by a reducing reagent such as LAH to give amine 12.4. Compound 12.4 is treated with acid to afford diamine 12.5, which follow by condensation with an oxalic acid derivative gives the dioxopiperazine 12.6. Treatment of 12.6 with NaH and alkyl halide gives compound 12.7. Removal of benzyl group by hydrogenation to give 12.8, which is alkylated with an a-halo alkyl ester to give compound 12.9. Hydrolysis of 12.9 affords acid 12.1.

Compounds 12.1, acids of the formula $R_C$COOH, are used to make additional compounds of the invention. Table 8 shows exemplary compounds 12.1's.

TABLE 8

| XCR$_I$R$_J$COOMe | R$_L$X | R$_C$COOH |
|---|---|---|
| Br—CO$_2$Me | BuBr | *butyl-substituted dioxopiperazine acetic acid* |
| Br—CO$_2$Me | PrBr | *propyl-substituted dioxopiperazine acetic acid* |
| Br—CO$_2$Me | isobutyl-Br | *isobutyl-substituted dioxopiperazine acetic acid* |
| Br—CO$_2$Me | cyclopropylmethyl-Br | *cyclopropylmethyl-substituted dioxopiperazine acetic acid* |
| Br—CO$_2$Me | benzyl-Br | *benzyl-substituted dioxopiperazine acetic acid* |
| Br—CO$_2$Me | (methylcyclopropyl)methyl-Br | *(methylcyclopropyl)methyl-substituted dioxopiperazine acetic acid* |
| Br—CO$_2$Me$_I$ | cyclopropyl-Br | *cyclopropyl-substituted dioxopiperazine acetic acid* |

TABLE 8-continued

| XCR$_I$R$_J$COOMe | R$_L$X | R$_C$COOH |
|---|---|---|
| Br–CH$_2$–CO$_2$Me | iPrBr | 4-isopropyl-2,3-dioxopiperazin-1-yl acetic acid |
| (S)-Br–CH(CH$_3$)–CO$_2$Me | BuBr | (S)-2-(4-butyl-2,3-dioxopiperazin-1-yl)propanoic acid |
| (S)-Br–CH(CH$_3$)–CO$_2$Me | PrBr | (S)-2-(4-propyl-2,3-dioxopiperazin-1-yl)propanoic acid |
| (S)-Br–CH(CH$_3$)–CO$_2$Me | iBuBr | (S)-2-(4-isobutyl-2,3-dioxopiperazin-1-yl)propanoic acid |
| (S)-Br–CH(CH$_3$)–CO$_2$Me | cyclopropylmethyl Br | (S)-2-(4-(cyclopropylmethyl)-2,3-dioxopiperazin-1-yl)propanoic acid |
| (S)-Br–CH(CH$_3$)–CO$_2$Me | BnBr | (S)-2-(4-benzyl-2,3-dioxopiperazin-1-yl)propanoic acid |
| (S)-Br–CH(CH$_3$)–CO$_2$Me | (2-methylcyclopropyl)methyl Br | (S)-2-(4-((2-methylcyclopropyl)methyl)-2,3-dioxopiperazin-1-yl)propanoic acid |
| (S)-Br–CH(CH$_3$)–CO$_2$Me | cyclopropyl Br | (S)-2-(4-cyclopropyl-2,3-dioxopiperazin-1-yl)propanoic acid |
| (S)-Br–CH(CH$_3$)–CO$_2$Me | iPrBr | (S)-2-(4-isopropyl-2,3-dioxopiperazin-1-yl)propanoic acid |

TABLE 8-continued

| XCR₁R₁COOMe | R_LX | R_CCOOH |
|---|---|---|
| Br-CH(CH₃)-CO₂Me | BuBr | (structure: 4-butyl-2,3-dioxopiperazin-1-yl alanine) |
| Br-CH(CH₃)-CO₂Me | PrBr | (structure: 4-propyl-2,3-dioxopiperazin-1-yl alanine) |
| Br-CH(CH₃)-CO₂Me | isobutyl bromide | (structure: 4-isobutyl-2,3-dioxopiperazin-1-yl alanine) |
| Br-CH(CH₃)-CO₂Me | cyclopropylmethyl bromide | (structure: 4-(cyclopropylmethyl)-2,3-dioxopiperazin-1-yl alanine) |
| Br-CH(CH₃)-CO₂Me | benzyl bromide | (structure: 4-benzyl-2,3-dioxopiperazin-1-yl alanine) |
| Br-CH(CH₃)-CO₂Me | (2-methylcyclopropyl)methyl bromide | (structure: 4-((2-methylcyclopropyl)methyl)-2,3-dioxopiperazin-1-yl alanine) |
| Br-CH(CH₃)-CO₂Me | cyclopropyl bromide | (structure: 4-cyclopropyl-2,3-dioxopiperazin-1-yl alanine) |
| Br-CH(CH₃)-CO₂Me | iPrBr | (structure: 4-isopropyl-2,3-dioxopiperazin-1-yl alanine) |
| Br-C(CH₃)₂-CO₂Me | BuBr | (structure: 4-butyl-2,3-dioxopiperazin-1-yl 2-methylalanine) |

TABLE 8-continued
| XCR$_I$R$_J$COOMe | R$_L$X | R$_C$COOH |
|---|---|---|
|  | PrBr | 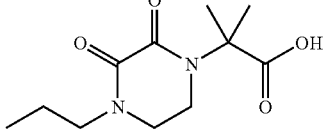 |
|  | 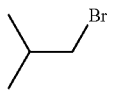 | 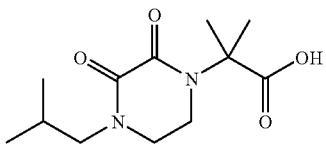 |
| 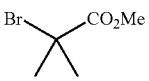 | 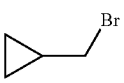 | 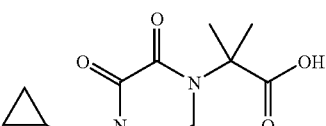 |
|  | 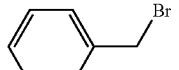 | 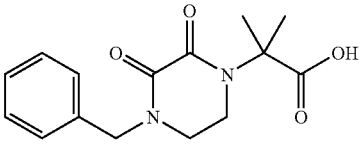 |
| 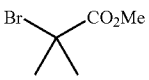 | 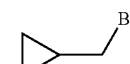 | 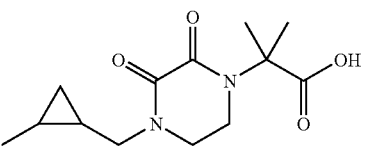 |
| 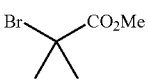 | 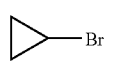 | 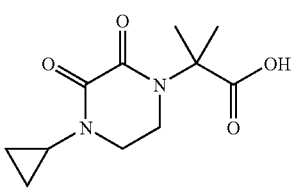 |
| 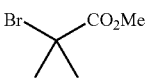 | 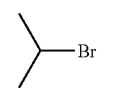 | 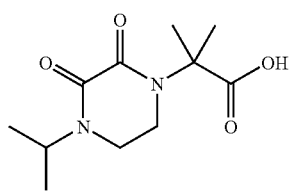 |

EXAMPLE 30

This example describes the synthesis of compounds of the formula

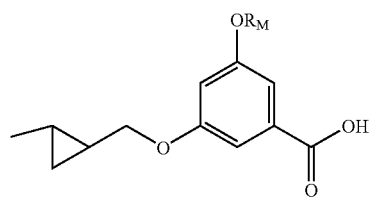

wherein $R_M$ is substituted or unsubstituted aliphatic or aromatic moiety. These compounds are prepared according to Scheme 13 and the procedure below.

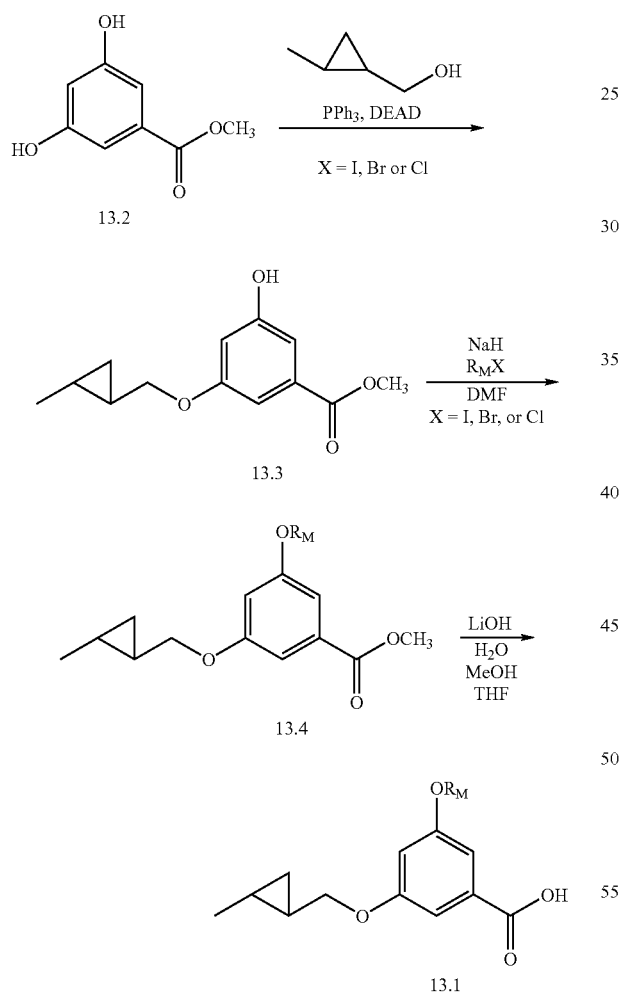

Mitsunobu reaction of 13.2 gives the corresponding aryl ether 13.3, which is followed by the alkylation with halide (NaH, $R_MX$, 1 eq) to afford aryl diether 13.4. Basic hydrolysis (LiOH, $H_2O$/THF/MeOH) of 13.4 gives acid 13.1. Compounds 13.1, acids of the formula $R_C$COOH, are used to make additional compounds of the invention. Table 9 shows exemplary compounds 13.1's.

TABLE 9

| $R_MX$ | $R_C$COOH |
|---|---|
| —I | (methoxy aryl diether carboxylic acid) |
| ethyl-I | (ethoxy aryl diether carboxylic acid) |
| isopropyl-I | (isopropoxy aryl diether carboxylic acid) |
| cyclopropyl-I | (cyclopropoxy aryl diether carboxylic acid) |
| cyclopropylmethyl-Br | (cyclopropylmethoxy aryl diether carboxylic acid) |
| isobutyl-Br | (isobutoxy aryl diether carboxylic acid) |

EXAMPLE 31

This example describes the synthesis of compounds of the formula

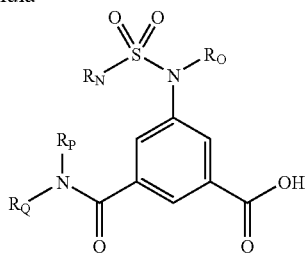

wherein $R_N$, $R_O$, $R_P$, and $R_Q$ are each independently substituted or unsubstituted aliphatic or aromatic moiety. These compounds are prepared according to Scheme 14 and the procedure below.

Scheme 14

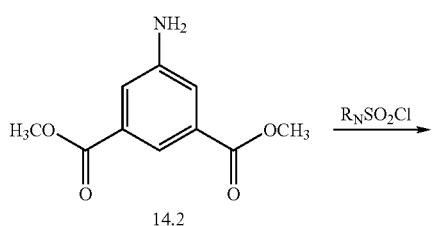

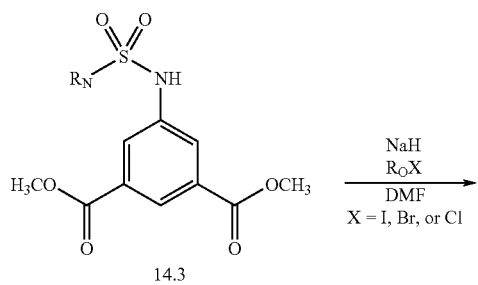

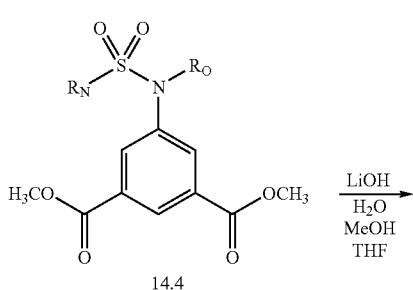

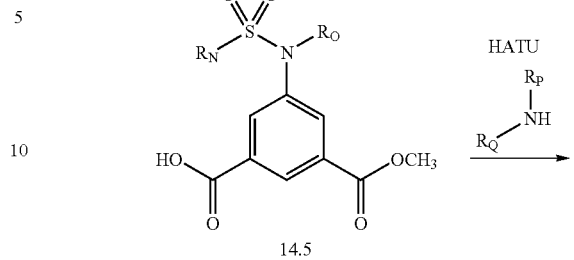

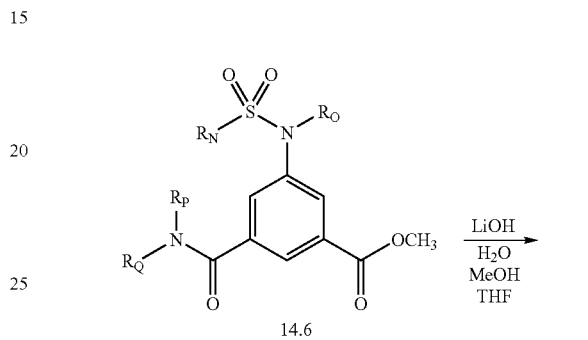

The treatment of aniline 14.2 with sulfonyl chloride gives the corresponding sulfonamide 14.3, which is follow by alkylation with halide to give 14.4. The basic hydrolysis of 14.4 affords the mono-acid 14.5, follow by amide coupling with corresponding amine to give 14.6. Basic hydrolysis (LiOH, H₂O/THF/MeOH) of 14.6 gives acid 14.1. Compounds 14.1, acids of the formula $R_C$COOH, are used to make additional compounds of the invention. Table 10 shows exemplary compounds 14.1's.

TABLE 10

| $R_P$NHR$_Q$ | $R_N$SO$_2$Cl | $R_O$X | $R_C$COOH |
|---|---|---|---|
| ![propylamine] | MeSO$_2$Cl | —I | ![product] |

TABLE 10-continued

| R_PNHR_Q | R_NSO_2Cl | R_OX | R_CCOOH |
|---|---|---|---|
| propyl-NH-propyl | MeSO_2Cl | Et-I | 3-[N-ethyl-N-(methylsulfonyl)amino]-5-(N,N-dipropylcarbamoyl)benzoic acid |
| propyl-NH-propyl | PhSO_2Cl | Me-I | 3-[N-methyl-N-(phenylsulfonyl)amino]-5-(N,N-dipropylcarbamoyl)benzoic acid |
| (R)-1-(4-fluorophenyl)ethylamine | MeSO_2Cl | Me-I | 3-[N-methyl-N-(methylsulfonyl)amino]-5-[(R)-1-(4-fluorophenyl)ethylcarbamoyl]benzoic acid |
| (R)-1-(4-fluorophenyl)ethylamine | MeSO_2Cl | Et-I | 3-[N-ethyl-N-(methylsulfonyl)amino]-5-[(R)-1-(4-fluorophenyl)ethylcarbamoyl]benzoic acid |
| (R)-1-(4-fluorophenyl)ethylamine | PhSO_2Cl | Me-I | 3-[N-methyl-N-(phenylsulfonyl)amino]-5-[(R)-1-(4-fluorophenyl)ethylcarbamoyl]benzoic acid |
| (S)-2-(methoxymethyl)pyrrolidine | MeSO_2Cl | Me-I | 3-[N-methyl-N-(methylsulfonyl)amino]-5-[(S)-2-(methoxymethyl)pyrrolidin-1-ylcarbonyl]benzoic acid |

TABLE 10-continued

| R_PNHR_Q | R_NSO_2Cl | R_OX | R_CCOOH |
|---|---|---|---|
| (S)-2-(methoxymethyl)pyrrolidine | MeSO_2Cl | ethyl iodide | 3-[N-ethyl(methylsulfonyl)amino]-5-[(2-(methoxymethyl)pyrrolidin-1-yl)carbonyl]benzoic acid |
| (S)-2-(methoxymethyl)pyrrolidine | PhSO_2Cl | methyl iodide | 3-[N-methyl(phenylsulfonyl)amino]-5-[(2-(methoxymethyl)pyrrolidin-1-yl)carbonyl]benzoic acid |
| N-methylpropylamine | MeSO_2Cl | methyl iodide | 3-[N-methyl(methylsulfonyl)amino]-5-[N-methyl-N-propylcarbamoyl]benzoic acid |
| N-methylpropylamine | MeSO_2Cl | ethyl iodide | 3-[N-ethyl(methylsulfonyl)amino]-5-[N-methyl-N-propylcarbamoyl]benzoic acid |
| N-methylpropylamine | PhSO_2Cl | methyl iodide | 3-[N-methyl(phenylsulfonyl)amino]-5-[N-methyl-N-propylcarbamoyl]benzoic acid |

EXAMPLE 32

This example describes the synthesis of compounds of the formula

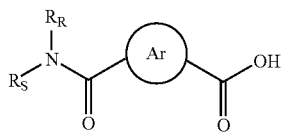

wherein $R_R$ and $R_S$ are each independently substituted or unsubstituted aliphatic or aromatic moiety, or $R_R$ and $R_S$ together form a substituted or unsubstituted cycloaliphatic or aromatic moiety. These compounds are prepared according to Scheme 15 and the procedure below.

Scheme 15

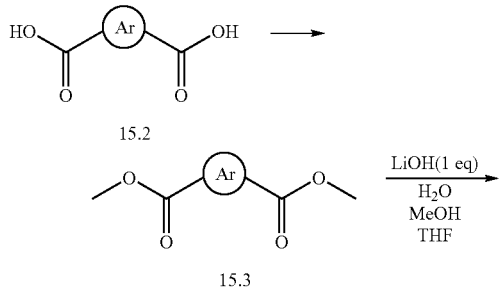

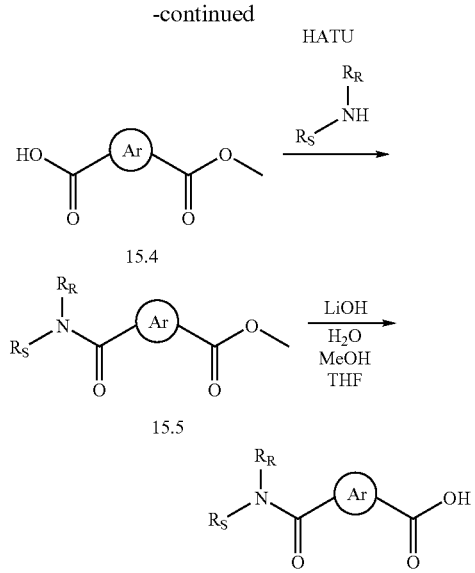

Esterfication of di-acid 15.2 with $TMSCH_2N_2$ gives the corresponding di-methyl ester 15.3. Basic hydrolysis (LiOH, 1 eq) of compound 15.3 yields mono-acid 15.4 which is then coupled with $R_RNHR_S$ to yield compound 15.5. The basic hydrolysis (LiOH, H2O/THF/MeOH) of 15.5 gives acid 15.1. Compound 15.1, an acid of the formula $R_C$COOH, are used to make additional compounds of the invention. Table 11 shows exemplary compounds 15.1's.

TABLE 11

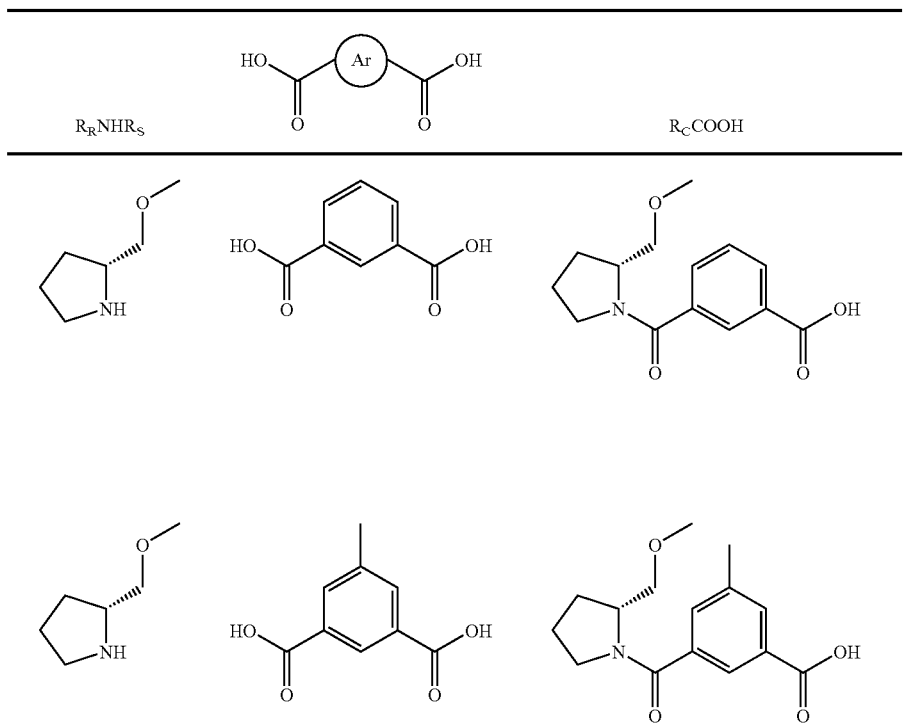

TABLE 11-continued

| R_RNHR_S | HO-C(O)-Ar-C(O)-OH | R_C-COOH |
|---|---|---|
| (S)-2-(methoxymethyl)pyrrolidine | 5-methoxyisophthalic acid | product amide with free COOH |
| (S)-2-propylpyrrolidine | isophthalic acid | product amide with free COOH |
| (S)-2-propylpyrrolidine | 5-methylisophthalic acid | product amide with free COOH |
| (S)-2-propylpyrrolidine | 5-methoxyisophthalic acid | product amide with free COOH |
| (S)-2-(ethoxymethyl)pyrrolidine | isophthalic acid | product amide with free COOH |
| (S)-2-(ethoxymethyl)pyrrolidine | 5-methylisophthalic acid | product amide with free COOH |

TABLE 11-continued

TABLE 11-continued

TABLE 11-continued
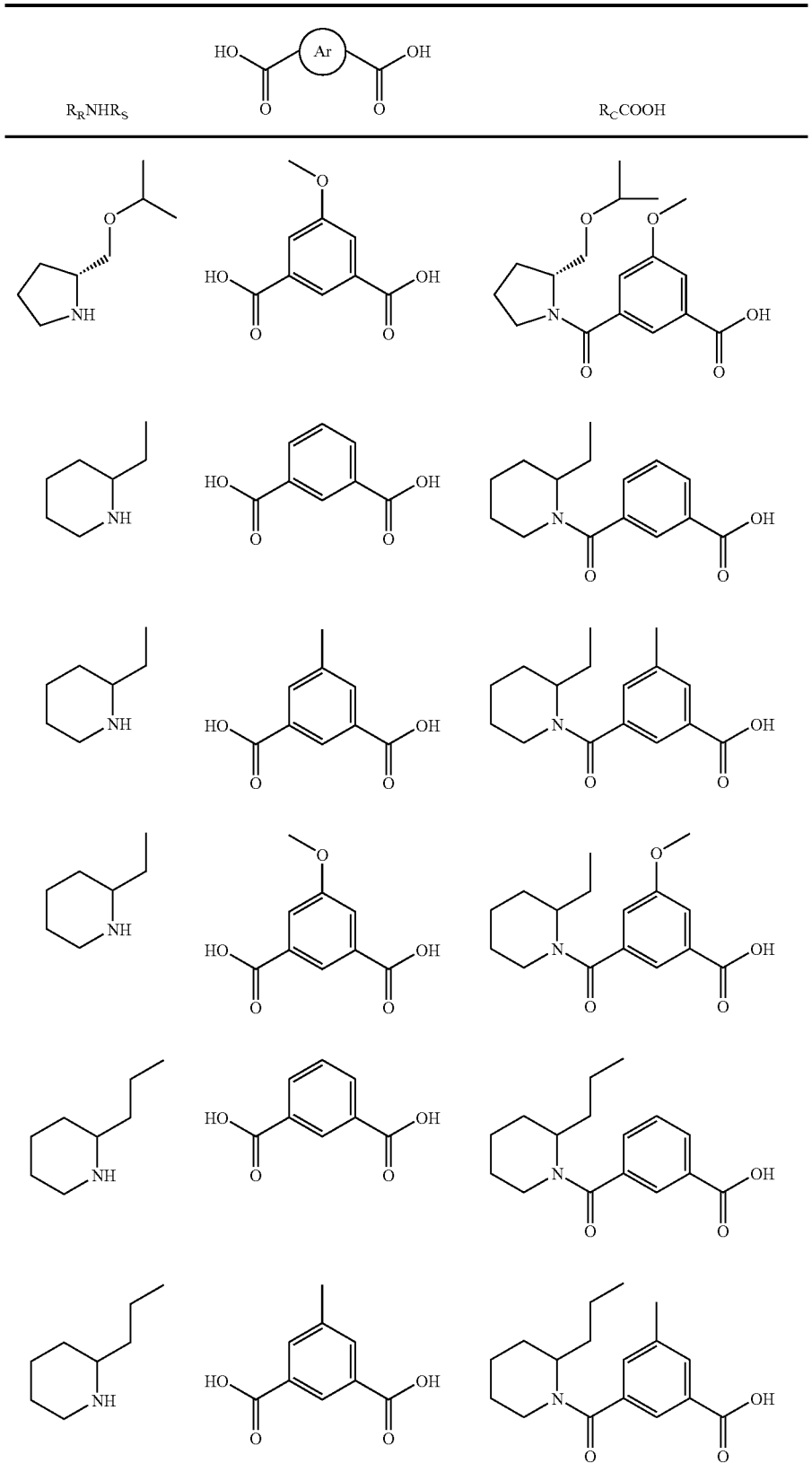

TABLE 11-continued
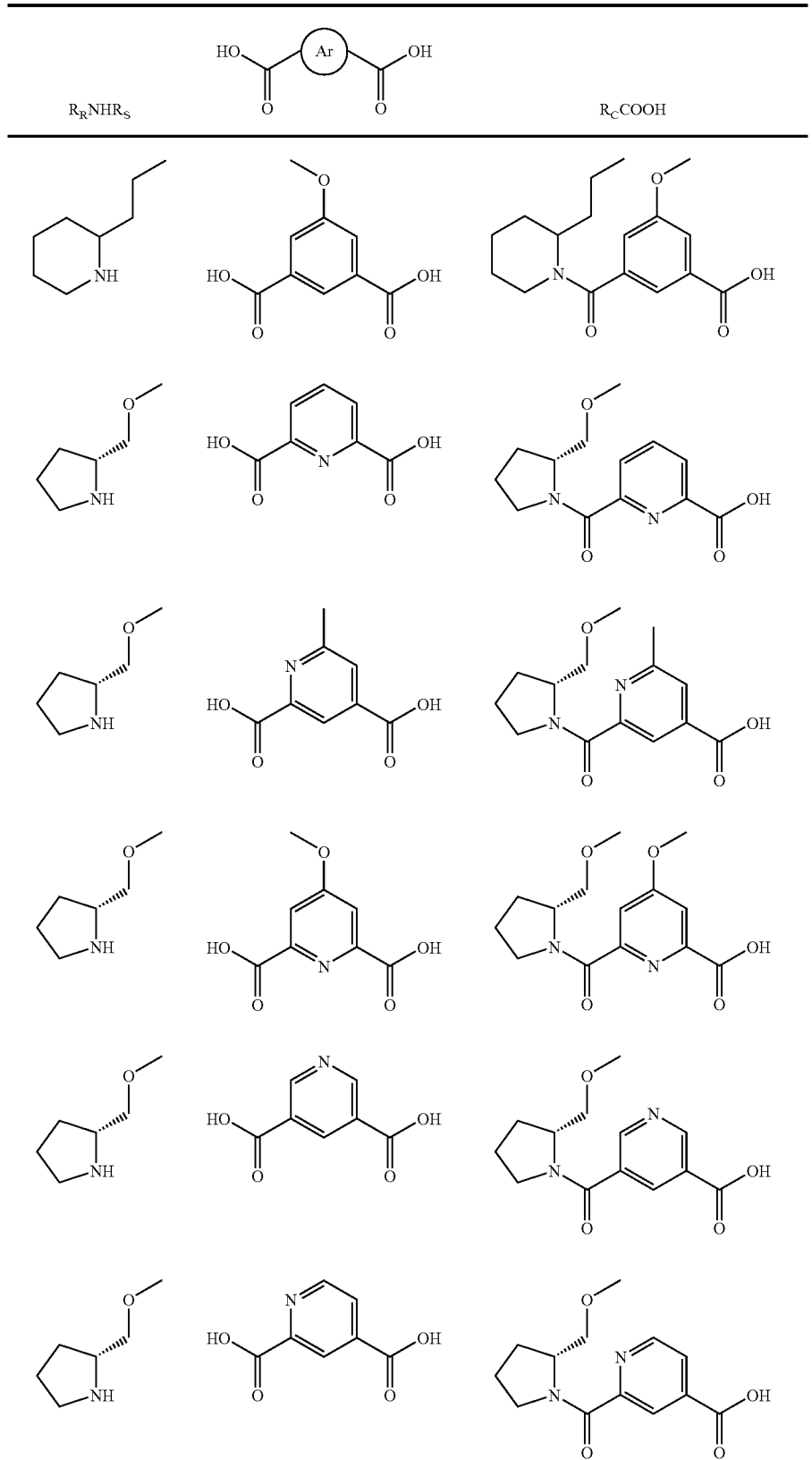

TABLE 11-continued
| $R_RNHR_S$ | HO-Ar-OH dicarboxylic | $R_CCOOH$ |
|---|---|---|
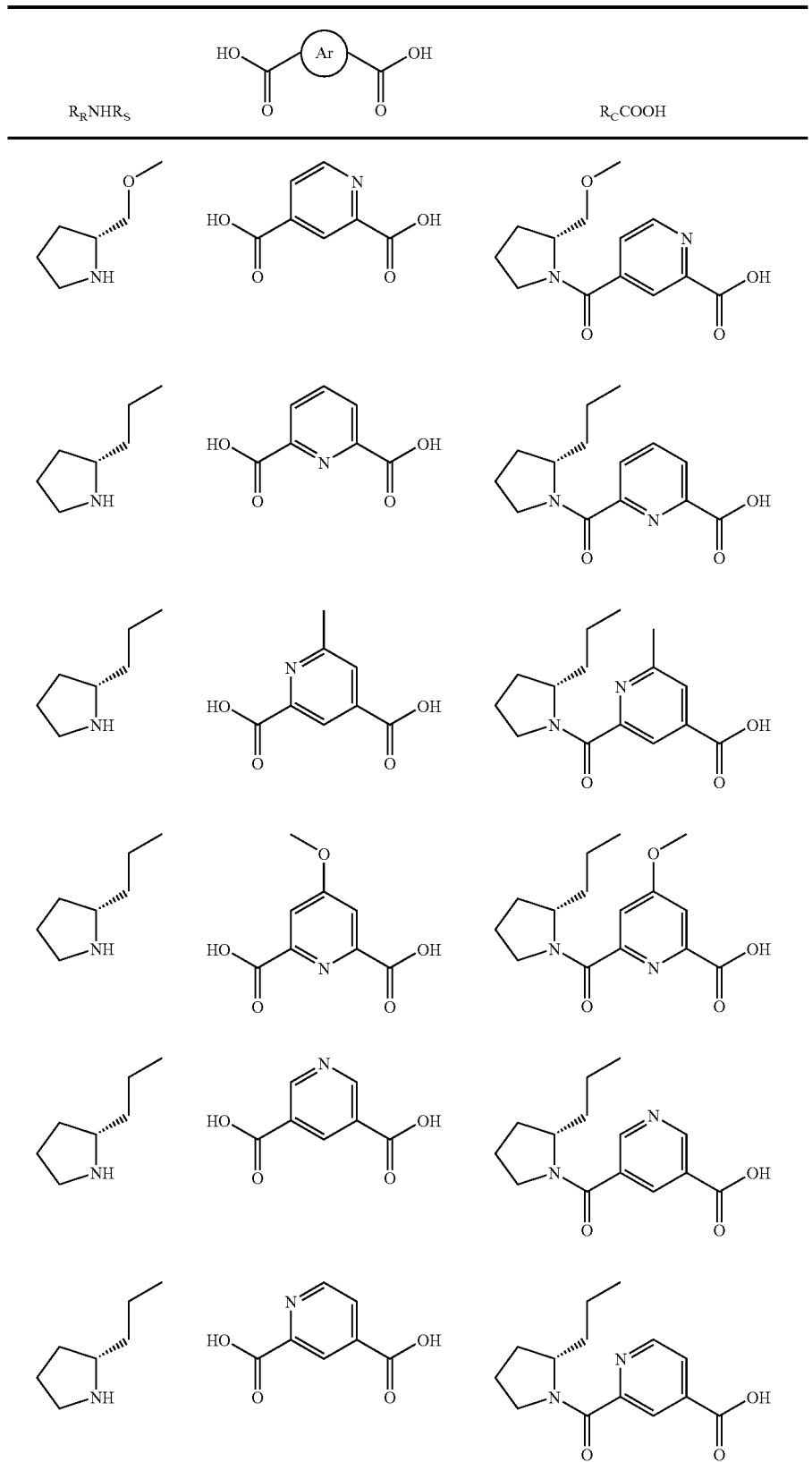

TABLE 11-continued
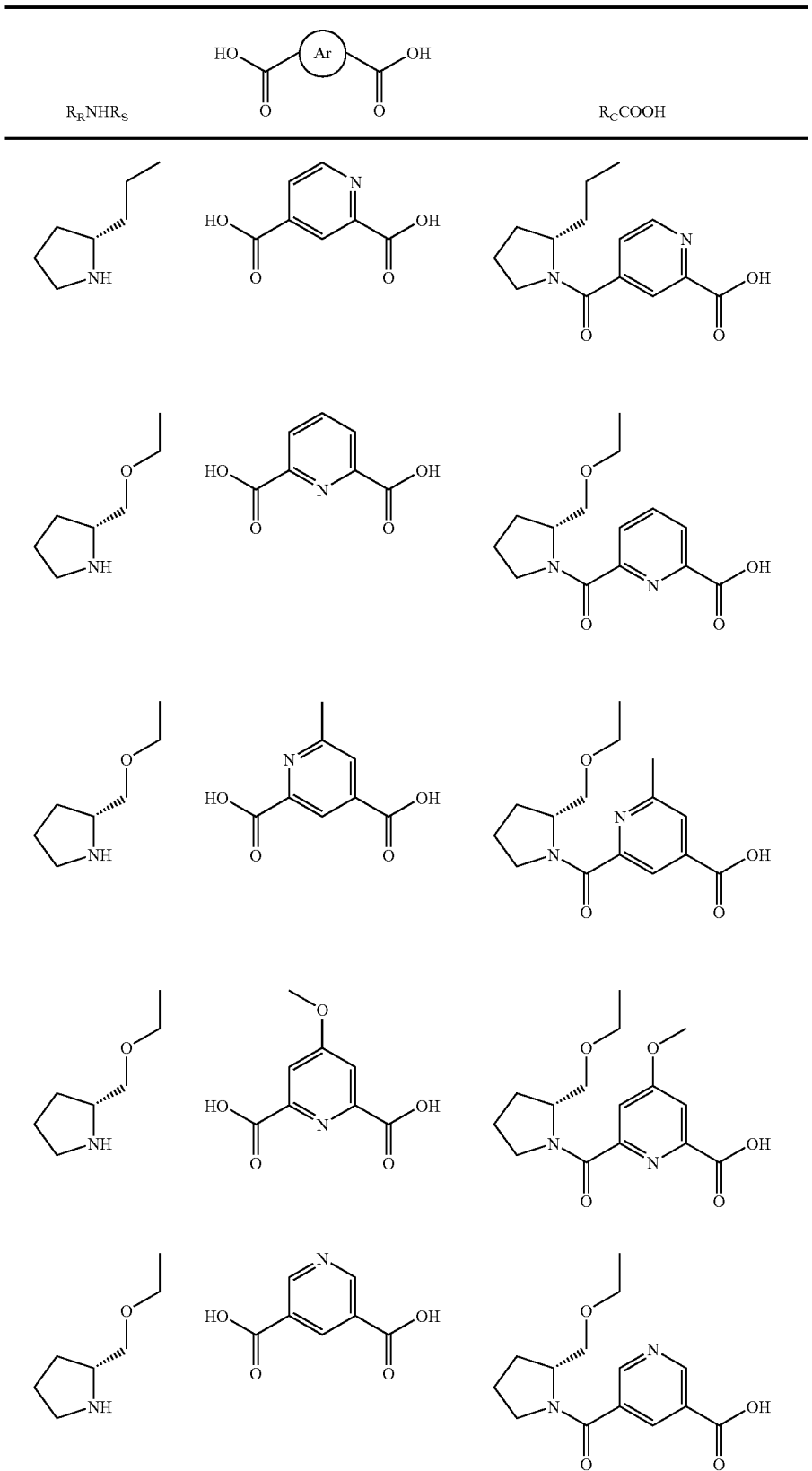

TABLE 11-continued
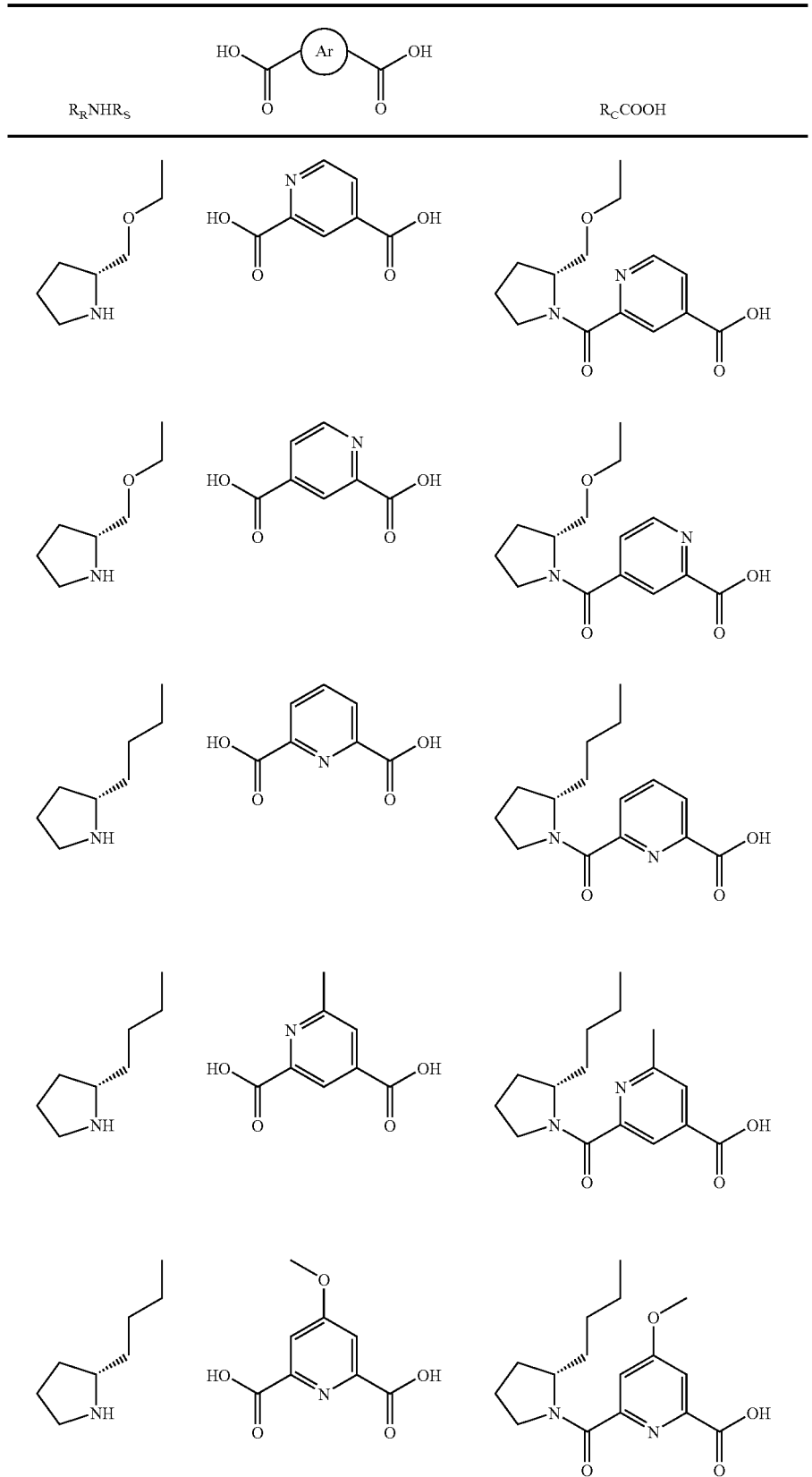

TABLE 11-continued
| $R_RNHR_S$ | HOOC-Ar-COOH | $R_C$COOH |
|---|---|---|
| 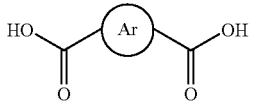 | 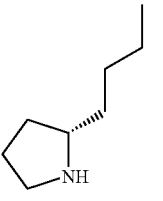 | 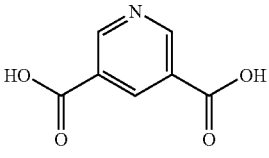 |
| 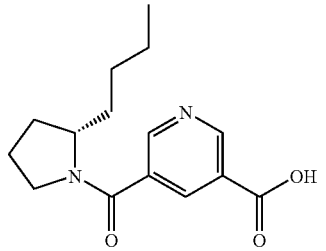 | 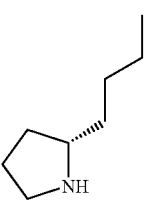 | 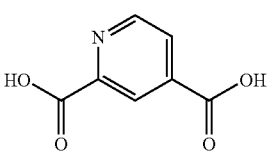 |
| 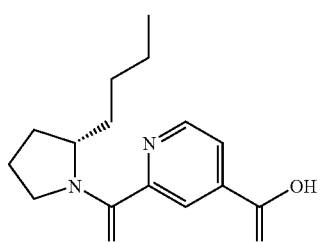 | 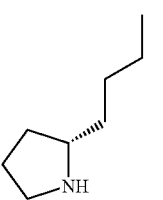 | 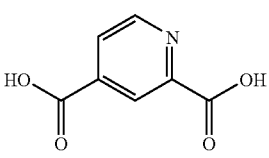 |
| 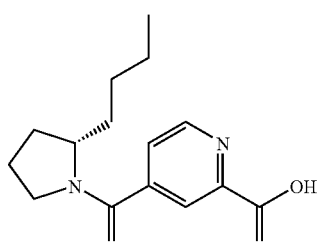 | 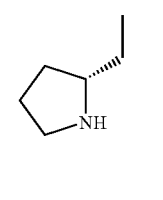 | 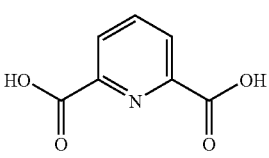 |
| 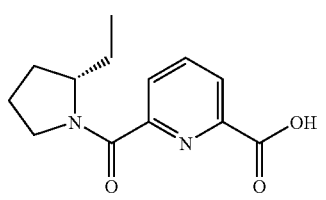 | 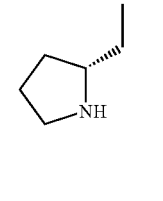 | 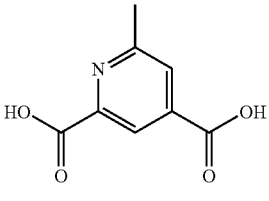 |
| 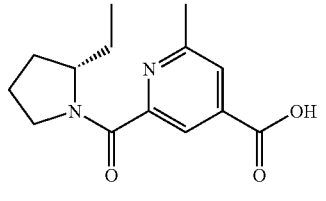 | 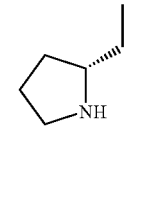 | 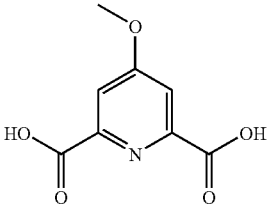 |

TABLE 11-continued

TABLE 11-continued
| R<sub>R</sub>NHR<sub>S</sub> | HOOC-Ar-COOH | R<sub>C</sub>COOH |
|---|---|---|
| 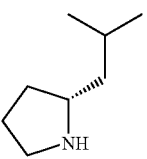 | 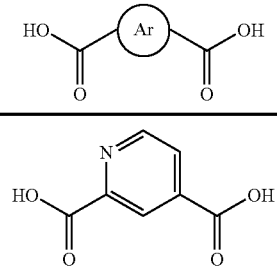 | 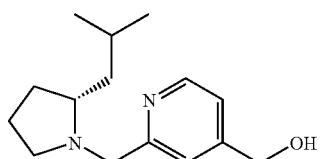 |
| 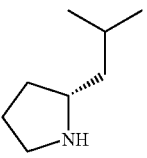 | 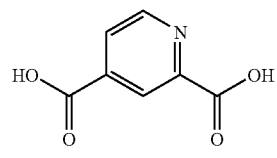 | 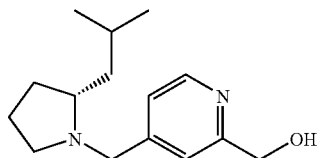 |
| 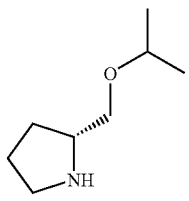 | 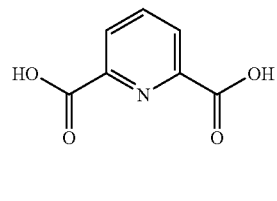 | 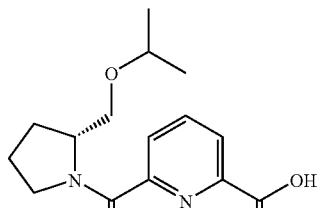 |
| 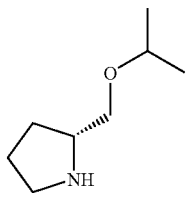 | 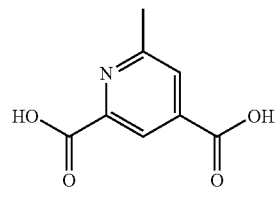 | 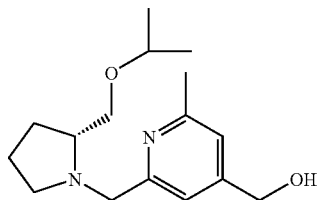 |
| 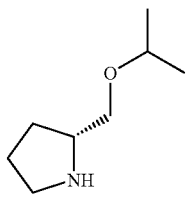 | 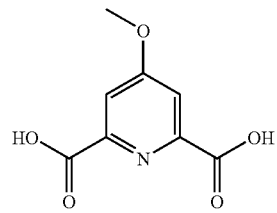 | 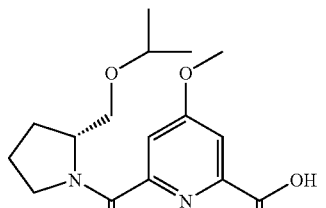 |
| 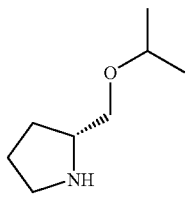 | 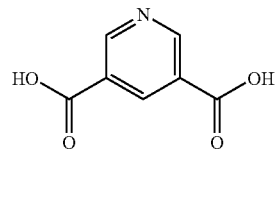 | 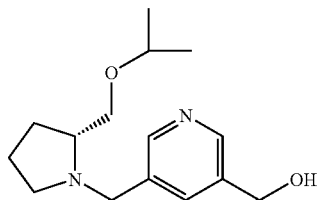 |

TABLE 11-continued
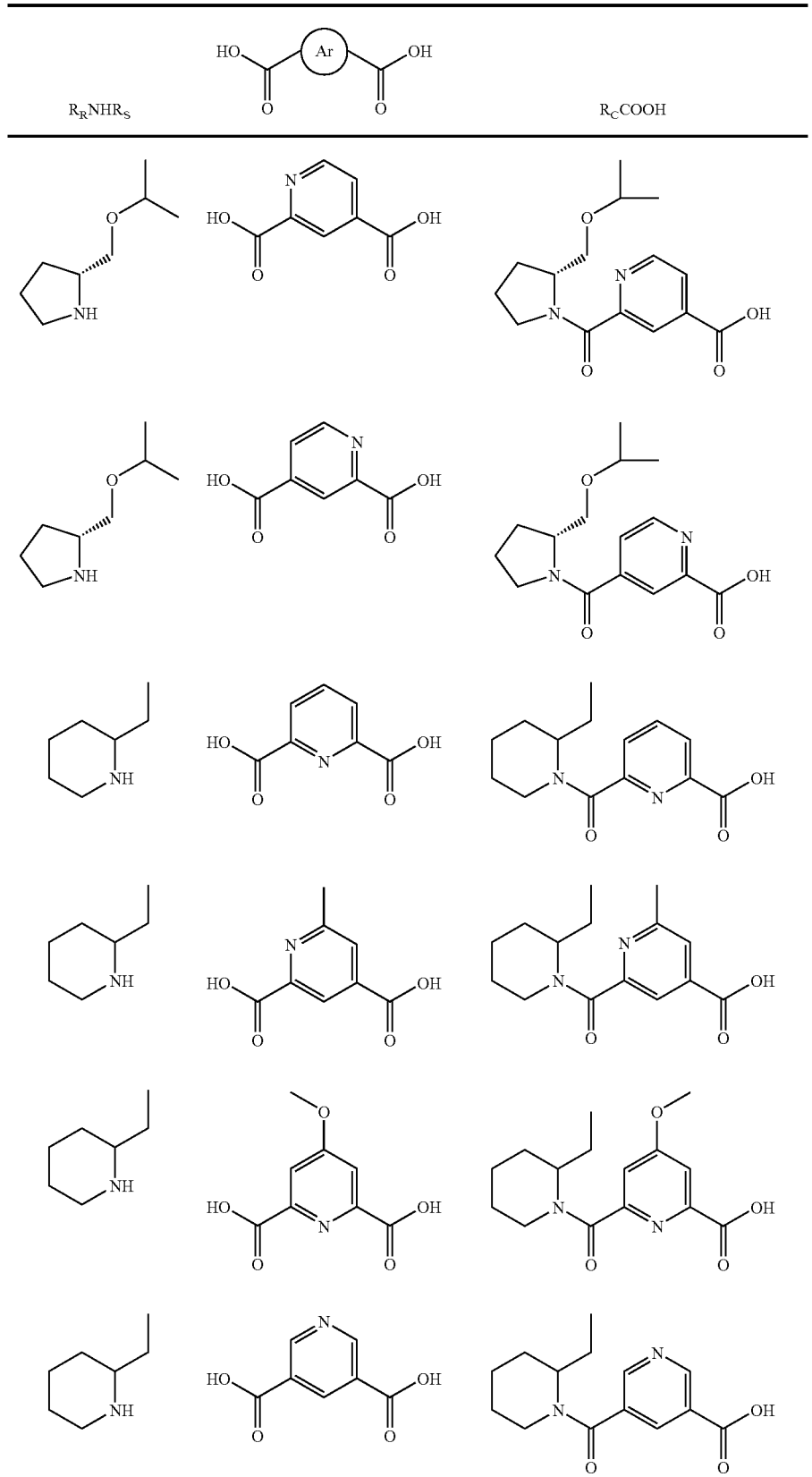

TABLE 11-continued

TABLE 11-continued
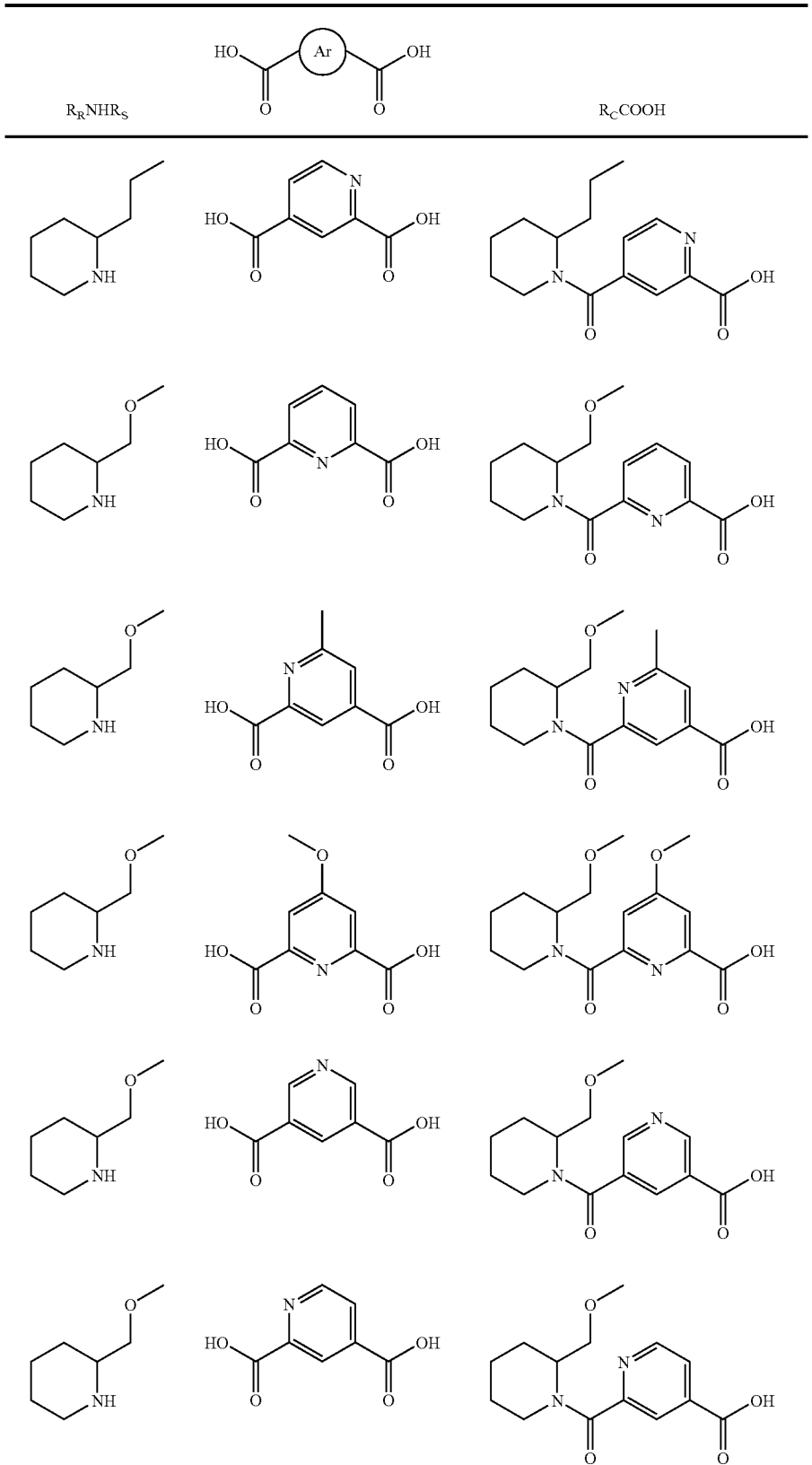

TABLE 11-continued

| R_RNHR_S | HOOC-Ar-COOH | R_CCOOH |
|---|---|---|

TABLE 11-continued
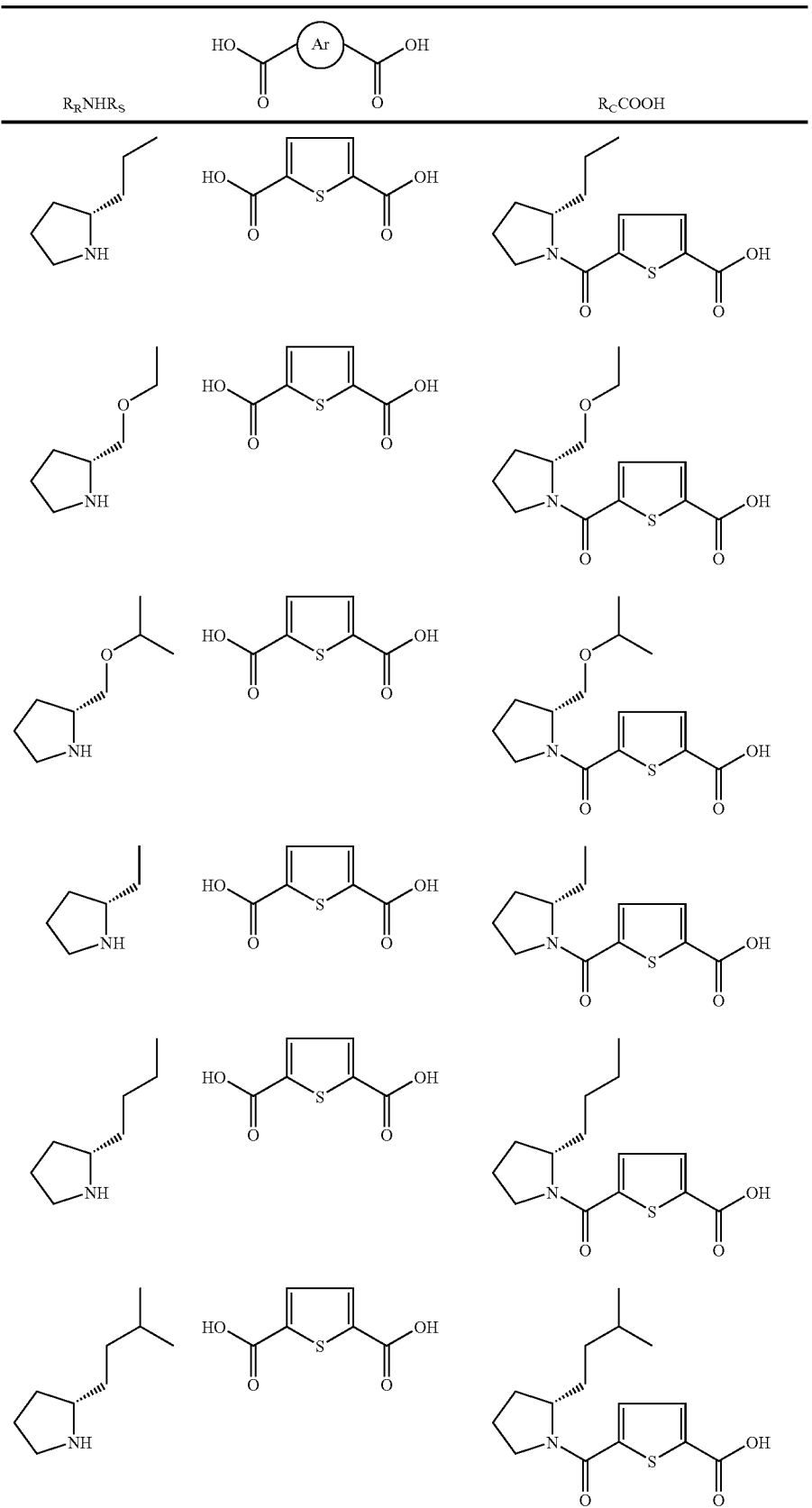

TABLE 11-continued
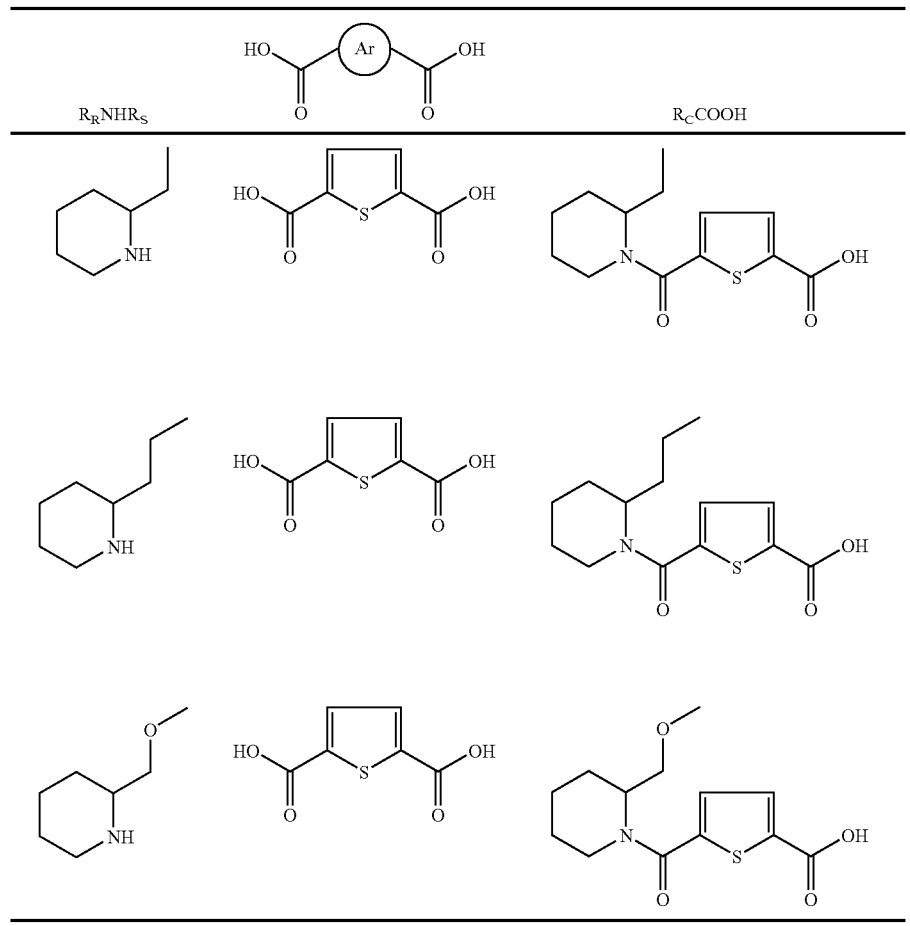
EXAMPLE 33
This example describes the synthesis of compounds of the formula
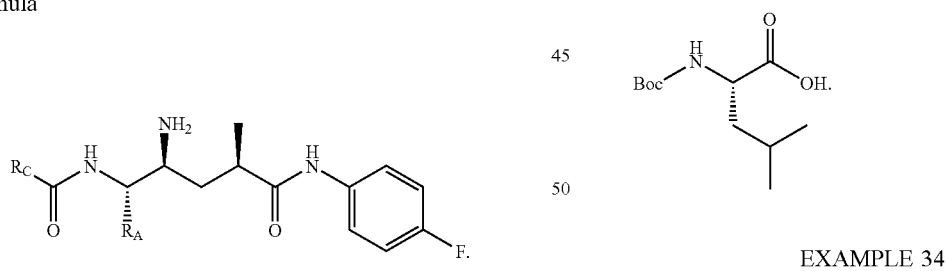
These compounds are prepared according to Example 23 except for using
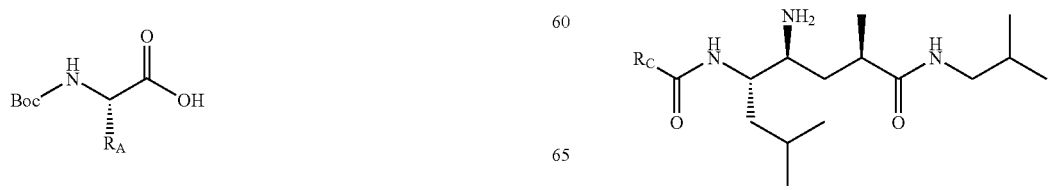
as a reagent instead of
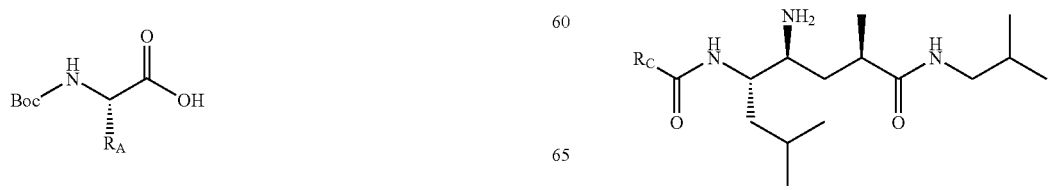
EXAMPLE 34
This example describes the synthesis of compounds of the formula which are prepared according to Example 13 except for using acids of the formula $R_C$COOH as a reagent instead of N,N-dipropyl-isophthalamic acid.

EXAMPLE 35

This example describes the synthesis of compounds of the formula

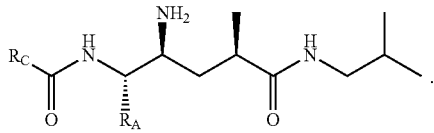

These compounds are prepared according to Example 34 except for using

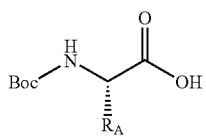

as a reagent instead of

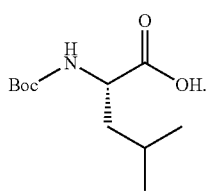

EXAMPLE 36

This example describes the synthesis of

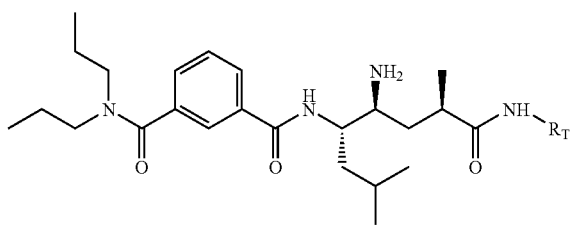

where $R_T$ is substituted or unsubstituted aliphatic or aromatic moiety. These compounds are prepared according to Example 10 except for using amines of the formula $H_2NR_T$ instead of 2-amino-N-benzyl-3-methyl-butyramide in step k.

EXAMPLE 37

This example describes the synthesis of compounds of the formula

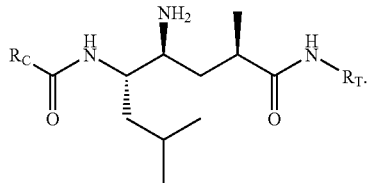

These compound are prepared according to Example 36 except for using acids of the formula $R_C$COOH as a reagent instead of N,N-dipropyl-isophthalamic acid.

EXAMPLE 38

This example describes the synthesis of compounds of the formula

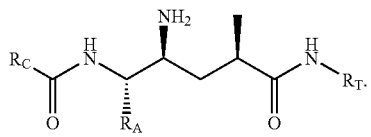

These compounds are prepared according to Example 37 except for using

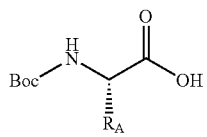

as a reagent instead of

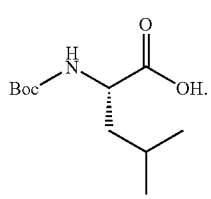

EXAMPLE 39

This example describes the synthesis of compounds of the formula

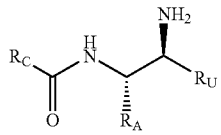

where $R_U$ is substituted or unsubstituted alkyl. These compounds are made according to Scheme 16 and the procedure below.

Scheme 16

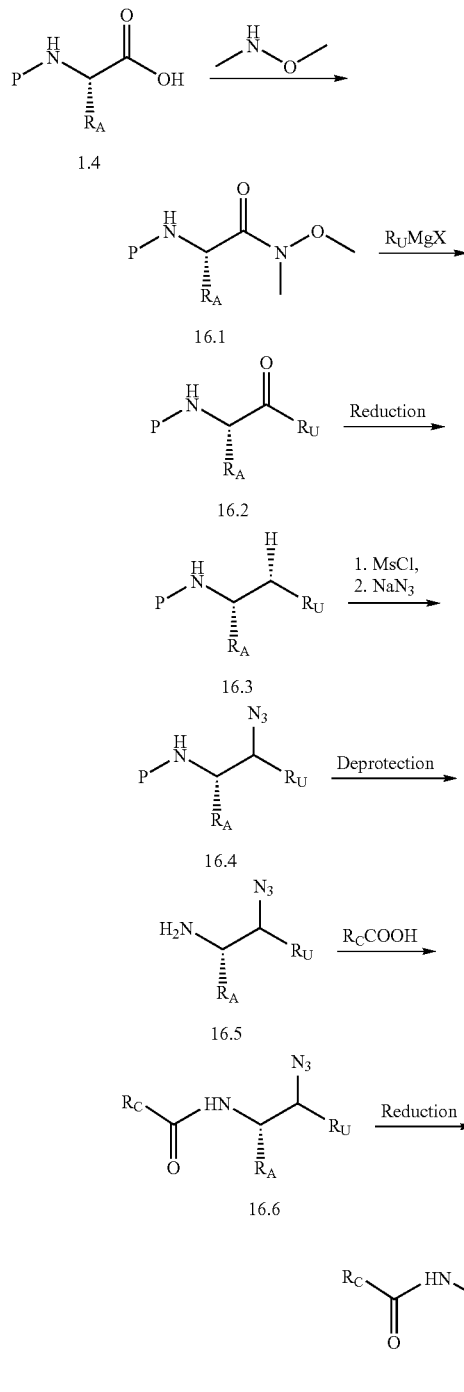

Compound 16.1 is prepared by amide coupling of compound 1.4 with N,O-dimethylhydroxylamine. Reaction of Weinreb amide 16.1 with Grignard reagent $R_UMgX$ yields ketone 16.2 which is then reduced to alcohol 16.3. Mesylation of compound 16.3 followed by the addition of azide replacement yields compound 16.4 which is deprotected to yield amine 16.5. Amide coupling of compound 16.5 and acid $R_C$COOH with amide coupling reagents yields compound 16.6 which is reduced to make product 16.7.

What is claimed is:

1. An isolated compound having the structure:

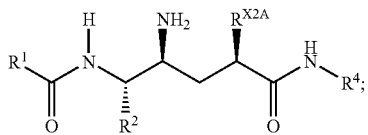

or pharmaceutically acceptable derivative thereof;

wherein $R^1$ is an aliphatic, heteroaliphatic, aromatic or heteroaromatic moiety, or $R^1$, taken together with R', may form a cycloheteroaliphatic moiety;

$R^2$ is an aliphatic, heteroaliphatic, aromatic or heteroaromatic moiety, or $R^2$, taken together with R', may form a cycloheteroaliphatic moiety;

$R^4$ is hydrogen, an aliphatic, heteroaliphatic, aromatic or heteroaromatic moiety, or $R^4$, taken together with a substituent present on $X^2$ or $X^3$, may form a cycloaliphatic, cycloheteroaliphatic, aromatic, or heteroaromatic moiety; and $R^{X2A}$ is hydrogen or an aliphatic, heteroaliphatic, aryl, heteroaryl, -(alkyl)aryl, -(alkyl)heteroaryl, -(heteroalkyl)aryl, or -(heteroalkyl)heteroaryl moiety;

wherein at least one of $R^1$, $R^2$, $R^{X2A}$ and $R^4$ comprises a cycloheteroaliphatic or heteroaromatic moiety.

2. The compound of claim 1, wherein $R^{X2A}$ is a substituted or unsubstituted, linear or branched lower alkyl moiety.

3. The compound of claim 2, wherein $R^{X2A}$ is methyl, ethyl, propyl, isopropyl or phenethyl.

4. The compound of claim 1, wherein $R^1$ has one of the following structures:

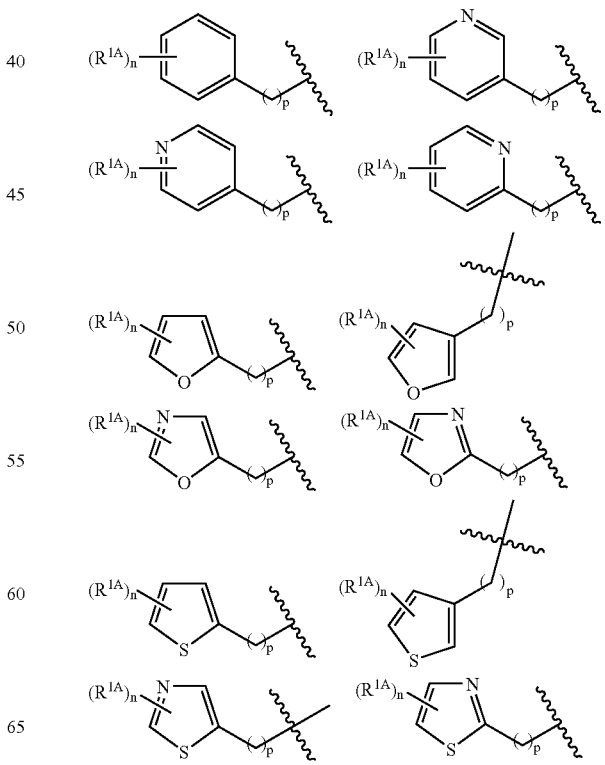

-continued

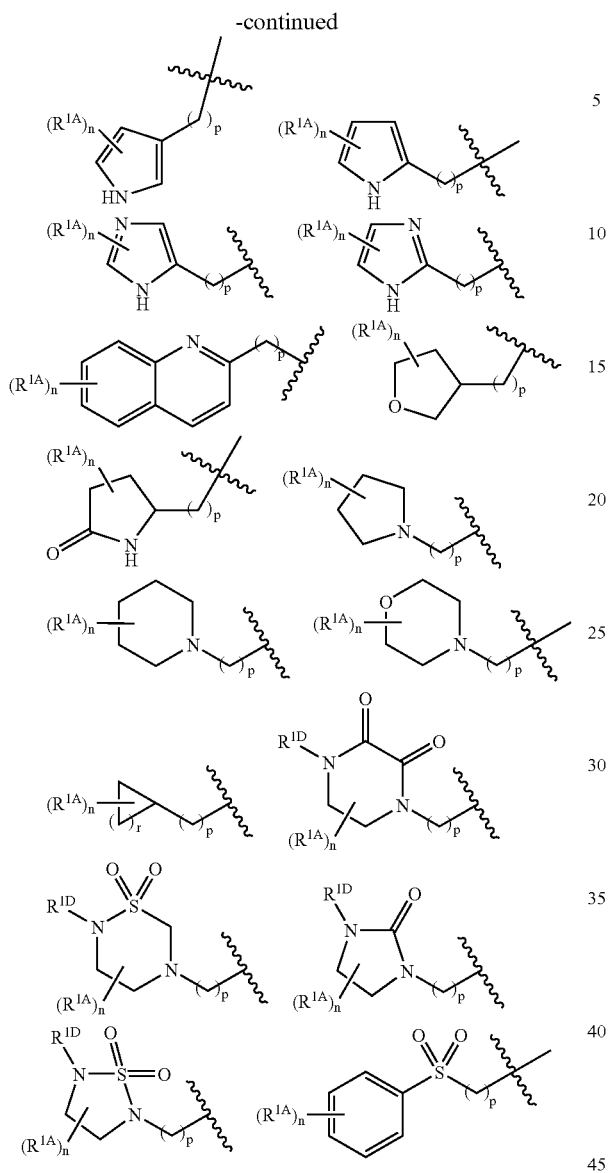

wherein $R^{1A}$ is hydrogen, alkyl, heteroalkyl, aryl, heteroaryl, -(alkyl)aryl, -(alkyl)heteroaryl, —$OR^{1B}$, —$SR^{1B}$, —$N(R^{1B})_2$, —$SO_2N(R^{1B})_2$, —$C(=O)N(R^{1B})_2$, halogen, —CN, —$NO_2$, —$C(=O)OR^{1B}$, $N(R^{1B})C(=O)R^{1C}$ or —$N(R^{1B})SO_2R^{1C}$; wherein each occcurrence of $R^{1B}$ and $R^{1C}$ is independently hydrogen, lower alkyl, lower heteroalkyl, aryl, heteroaryl, -(alkyl)aryl, -(alkyl)heteroaryl; or $R^{1B}$ and $R^{1C}$, taken together with the atoms to which they are attached, form a substituted or unsubstituted heterocyclic moiety; $R^{1D}$ is hydrogen, alkyl, heteroalkyl, aryl, heteroaryl, -(alkyl)aryl, -(alkyl)heteroaryl, acyl or a nitrogen protecting group; wherein n and p are each independently integers from 0 to 3 and r is an integer from 1 to 6; whereby each of the foregoing alkyl and heteroalkyl moieties may be linear or branched, substituted or unsubstituted, cyclic or acylic, and each of the foregoing aryl, heteroaryl, -(alkyl)aryl and -(alkyl)heteroaryl moieties may be substituted or unsusbtituted.

5. The compound of claim 4, wherein $R^1$ has one of the following structures:

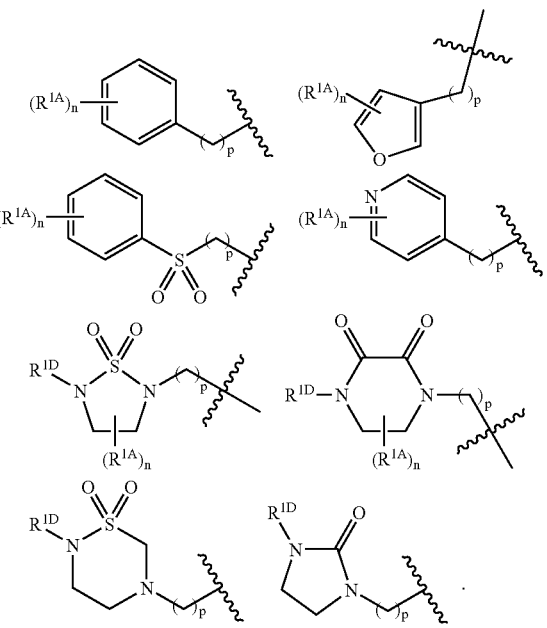

6. The compound of claim 4, wherein $R^1$ has one of the following structures:

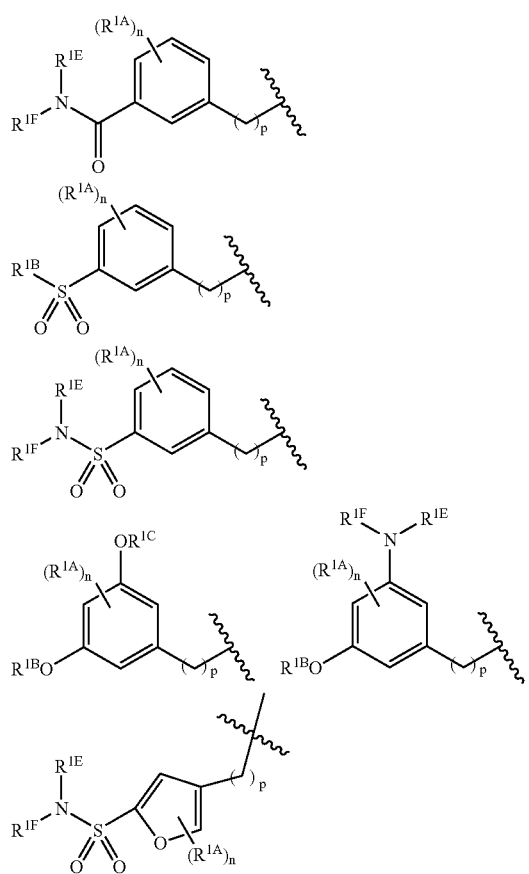

-continued

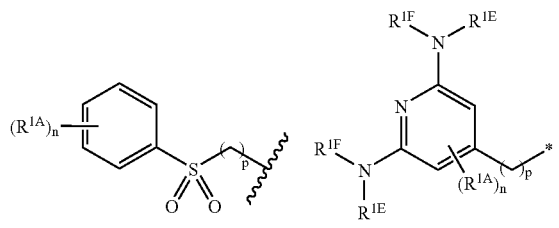

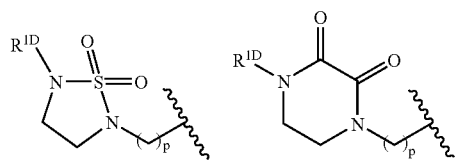

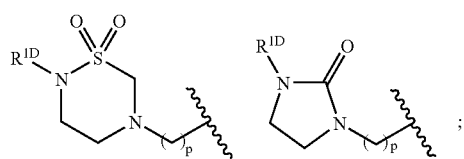

wherein $R^{1D}$ is hydrogen, lower alkyl, lower heteroalkyl, aryl, heteroaryl, -(alkyl)aryl; -(alkyl)heteroaryl or acyl; $R^{1E}$ and $R^{1F}$ are each independently hydrogen, lower alkyl, lower heteroalkyl, aryl, heteroaryl, -(alkyl)aryl, -(alkyl)heteroaryl, —C(=O)$R^{1C}$ or —SO$_2$R$^{1C}$, where $R^{1C}$ is hydrogen, lower alkyl, lower heteroalkyl, aryl, heteroaryl, -(alkyl)aryl or -(alkyl)heteroaryl; or $R^{1E}$ and $R^{1F}$ taken together form a 5–8 membered heterocyclic ring; or $R^{1E}$ and one occurrence of $R^{1A}$, taken together, form a substituted or unsubstituted, saturated or unsaturated heterocyclic ring.

7. The compound of claim 4, wherein $R^1$ has one of the following structures:

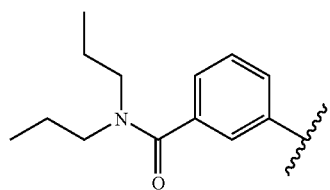

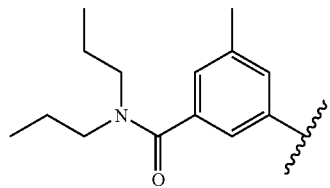

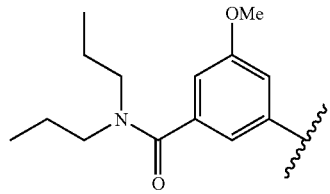

-continued

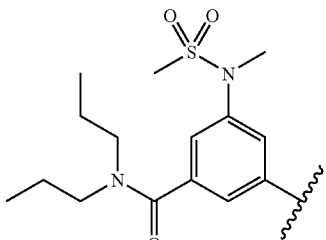

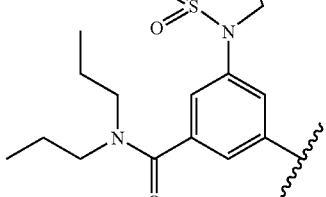

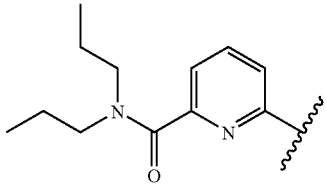

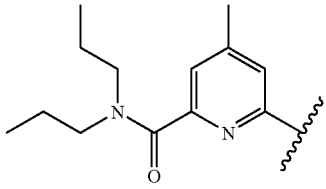

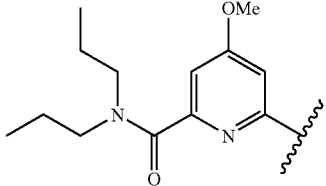

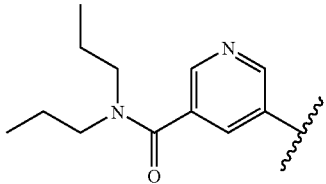

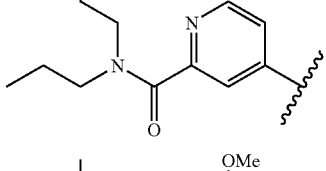

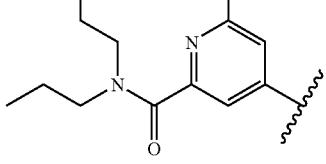

-continued
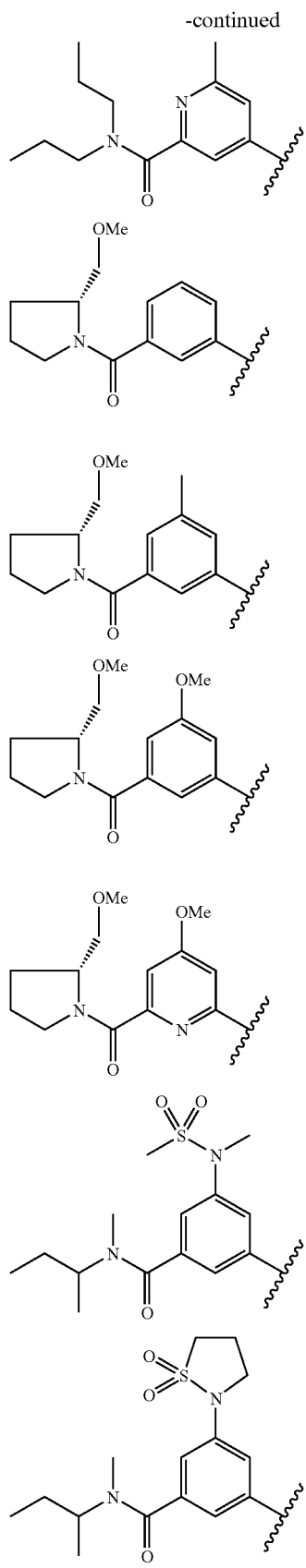
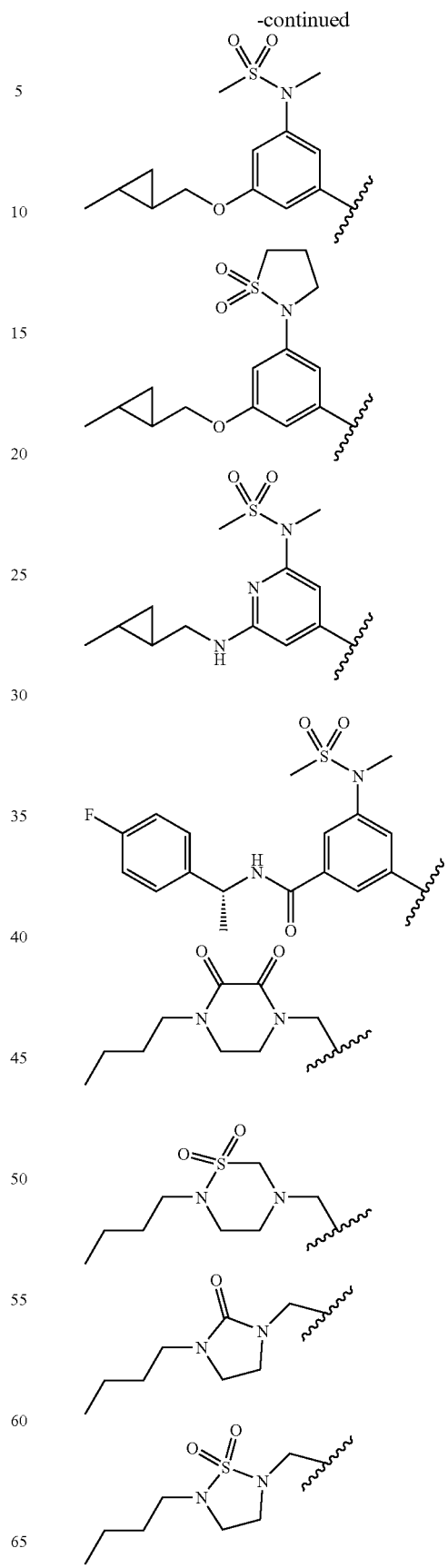

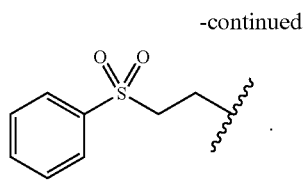
8. The compound of claim 4, wherein R¹ has one of the following structures:
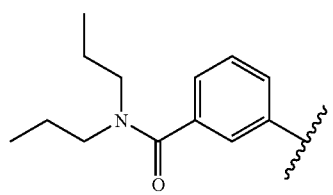
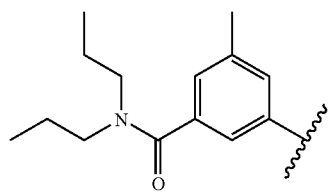
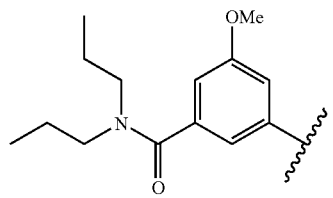
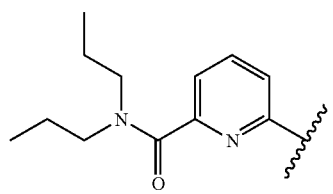
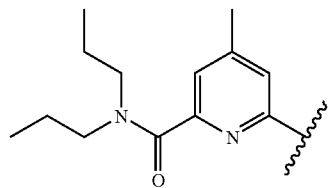
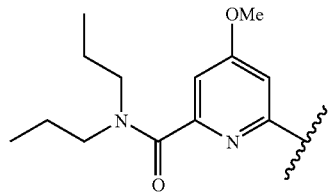
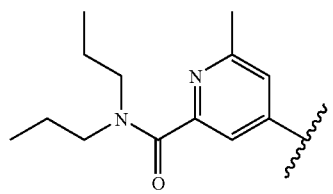
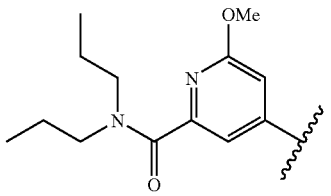
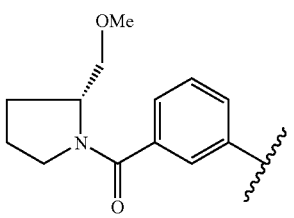
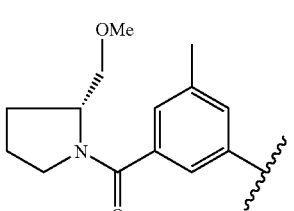
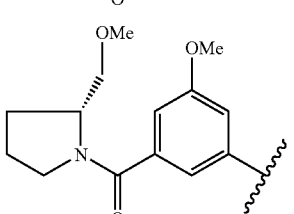
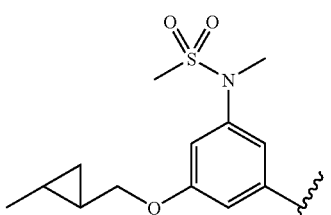
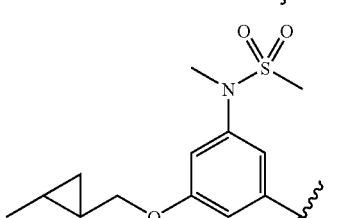
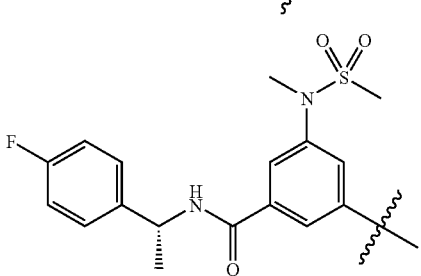

-continued

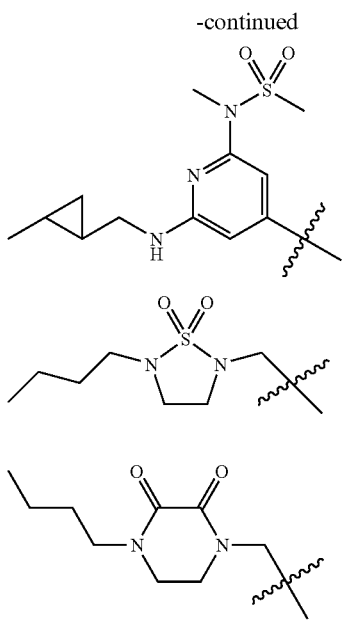

9. The compound of claim 4, wherein $R^1$ has one of the following structures:

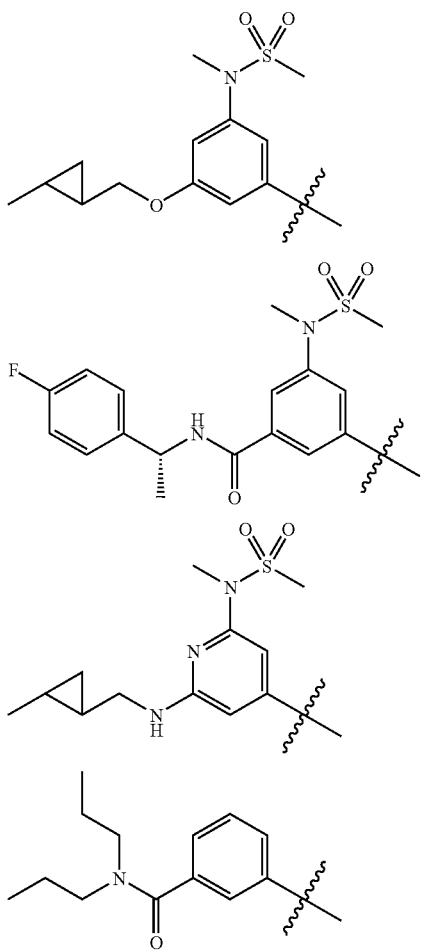

-continued

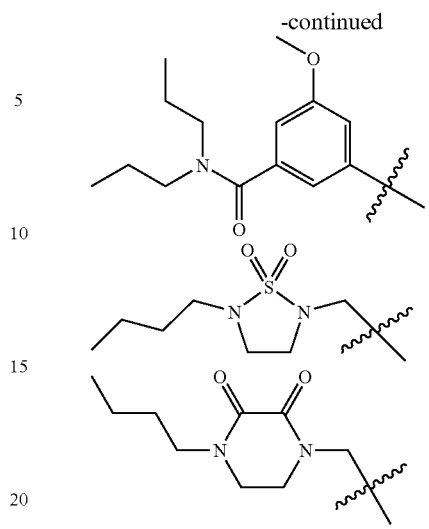

10. The compound of claim 1, wherein $R^2$ is lower alkyl, $-CH_2NR^{2A}R^{2B}$ or $-(CH_2)$phenyl, wherein the phenyl group is optionally substituted with one or more occurrences of $R^{2C}$, wherein $R^{2C}$ is hydrogen, alkyl, alkoxy or halogen; and wherein $R^{2A}$ and $R^{2B}$ are each independently hydrogen, lower alkyl, lower heteroalkyl, aryl, heteroaryl, -(alkyl)aryl or -(alkyl)heteroaryl; whereby each of the foregoing alkyl and heteroalkyl moieties may be linear or branched, substituted or unsubstituted, cyclic or acyclic, and each of the foregoing aryl, heteroaryl, -(alkyl)aryl and -(alkyl)heteroaryl moieties may be substituted or unsusbtituted.

11. The compound of claim 10, wherein $R^2$ has one of the following structures:

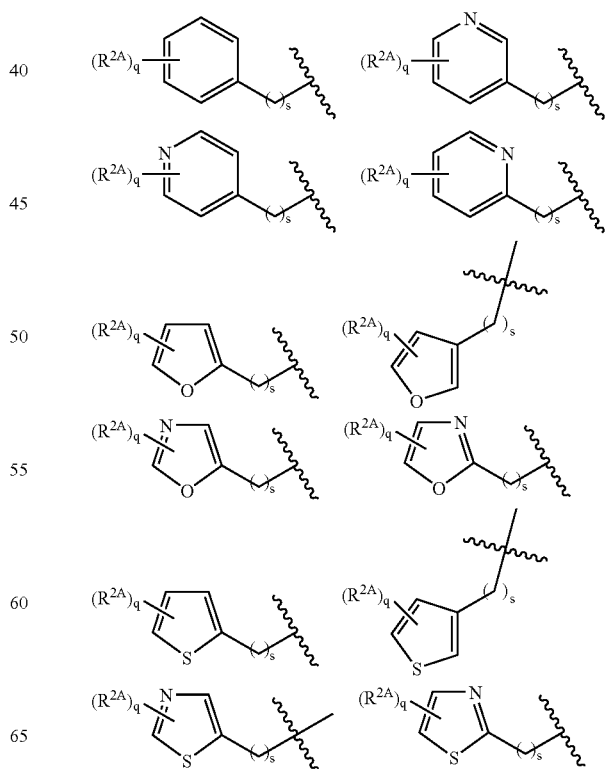

-continued

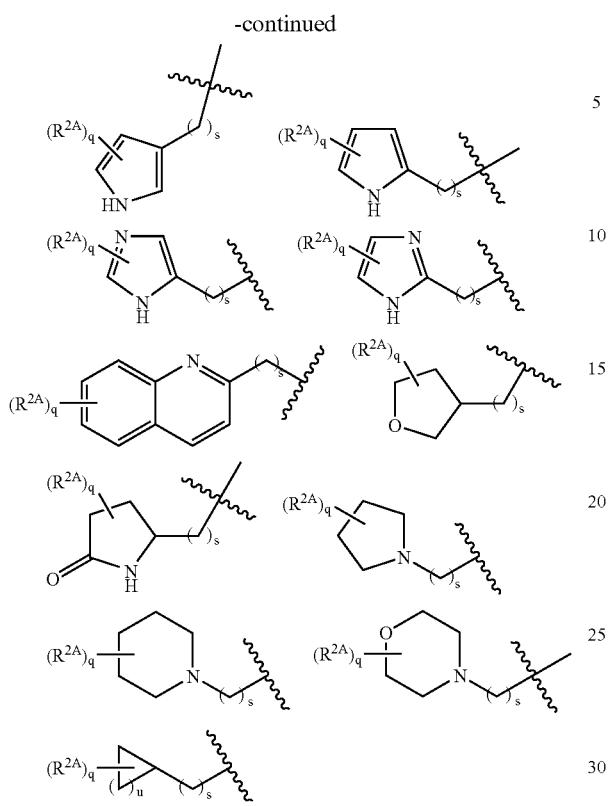

wherein $R^{2A}$ is hydrogen, alkyl, heteroalkyl, aryl, heteroaryl, -(alkyl)aryl or -(alkyl)heteroaryl, $-OR^{2B}$, $-SR^{2B}$, $-N(R^{2B})_2$, $-SO_2N(R^{2B})_2$, $-C(=O)N(R^{2B})_2$, halogen, $-CN$, $-NO_2$, $-C(=O)OR^{2B}$, $-N(R^{2B})C(=O)R^{2C}$, wherein each occcurrence of $R^{2B}$ and $R^{2C}$ is independently hydrogen, lower alkyl, lower heteroalkyl, aryl, heteroaryl, -(alkyl)aryl or -(alkyl)heteroaryl, wherein q and s are each independently integers from 0 to 3 and u is an integer from 1 to 6; whereby each of the foregoing alkyl and heteroalkyl moieties may be linear or branched, substituted or unsubstituted, cyclic or acylic, and each of the foregoing aryl, heteroaryl, -(alkyl)aryl and -(alkyl)heteroaryl moieties may be substituted or unsusbtituted.

12. The compound of claim 10, wherein $R^2$ has one of the following structures:

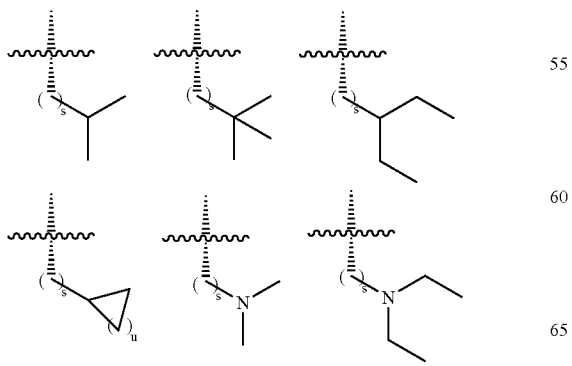

-continued

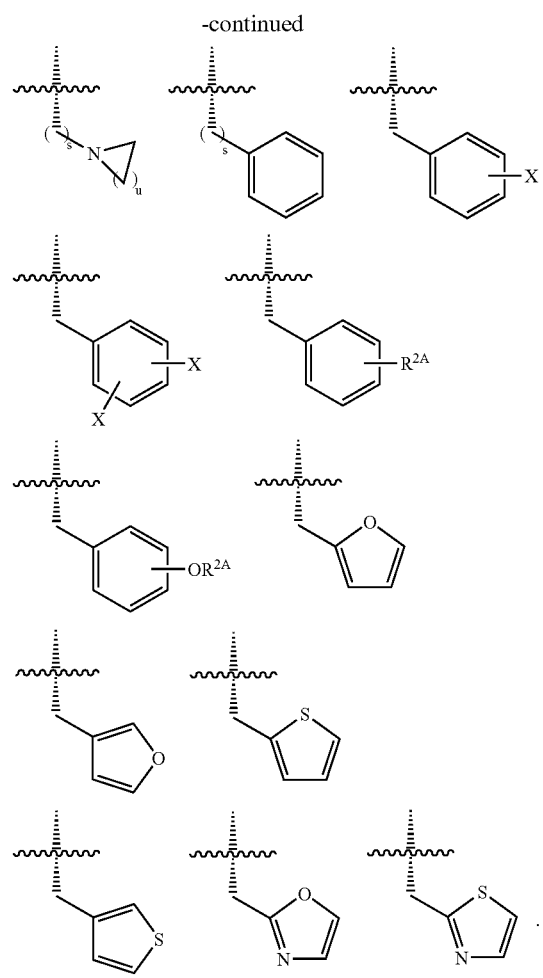

wherein each occcurrence of $R^{2A}$ is independently hydrogen or lower alkyl; each occurrence of X is independently a halogen; s is an integer from 0 to 3 and u is an integer from 1 to 6; whereby each of the foregoing alkyl moieties may be linear or branched, substituted or unsubstituted and cyclic or acylic.

13. The compound of claim 10, wherein each occurrence of X is independenly chlorine or fluorine and $R^{2A}$ is methyl.

14. The compound of claim 10, wherein $R^2$ has one of the following structures:

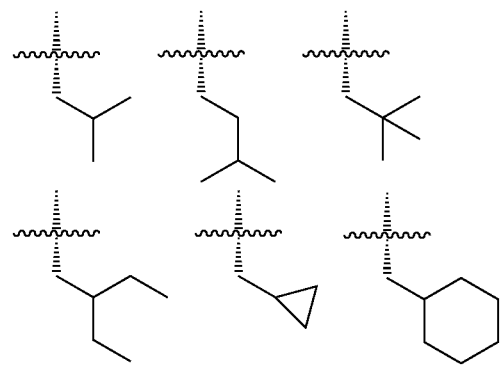

-continued

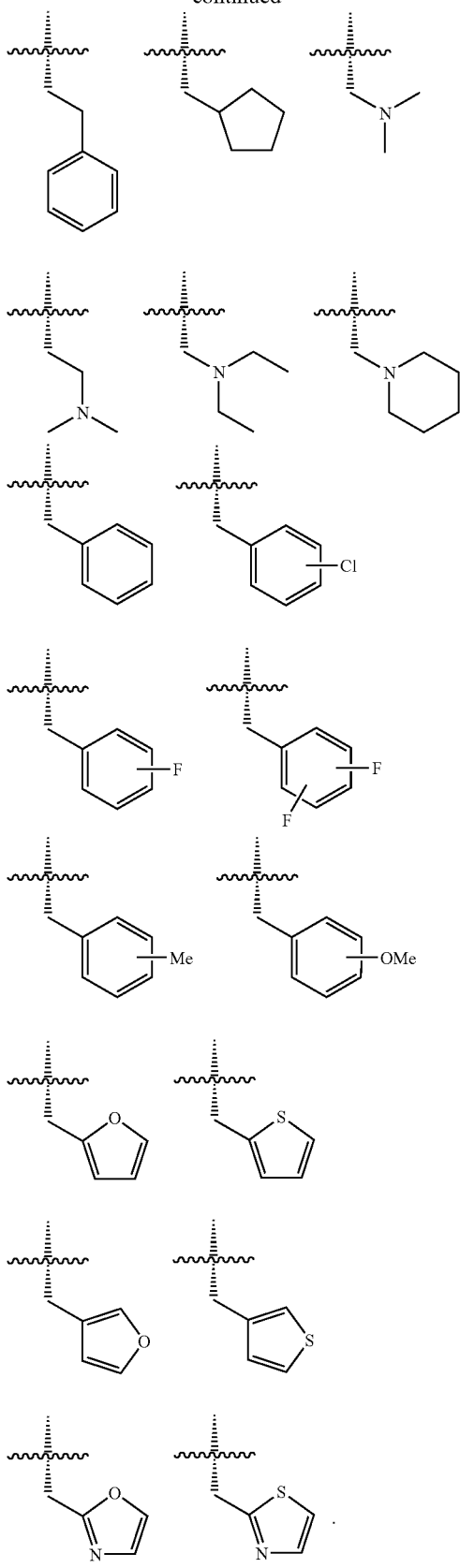

15. The compound of claim 10, wherein $R^2$ has one of the following structures:

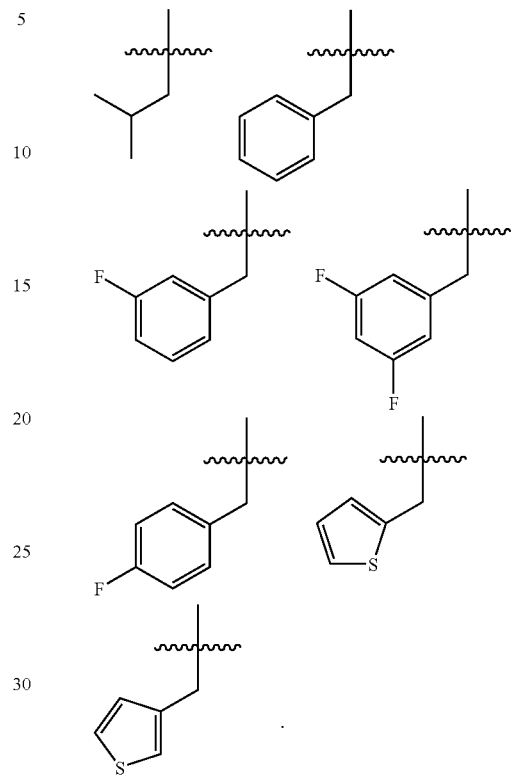

16. The compound of claim 1, wherein $R^4$ is substituted or unsubstituted, linear or branched, cyclic or acyclic alkyl, phenyl or —(CH$_2$)phenyl, wherein the phenyl group is optionally substituted with one or more occurrences of $R^{4A}$, wherein $R^{4A}$ is hydrogen, alkyl, heteroalkyl, aryl, heteroaryl, -(alkyl)aryl or -(alkyl)heteroaryl, —OR$^{4B}$, —SR$^{4B}$, —N(R$^{4B}$)$_2$, —SO$_2$N(R$^{4B}$)$_2$, —C(=O)N(R$^{4B}$)$_2$, halogen, —CN, —NO$_2$, —C(=O)OR$^{4B}$, —N(R$^{4B}$)C(=O)R$^{4C}$, wherein each occcurrence of $R^{4B}$ and $R^{4C}$ is independently hydrogen, lower alkyl, lower heteroalkyl, aryl, heteroaryl, -(alkyl)aryl, -(alkyl)heteroaryl, -(heteroalkyl)aryl, -(heteroalkyl)heteroaryl.

17. The compound of claim 16, wherein $R^4$ is substituted or unsubstituted, linear or branched, cyclic or acyclic alkyl, phenyl or —(CH$_2$)phenyl, wherein the phenyl group is optionally substituted with one or more occurrences of $R^{4A}$, wherein $R^{4A}$ is hydrogen, hydroxyl, alkyl, alkoxy or halogen.

18. The compound of claim 16, wherein $R^4$ has one of the following structures:

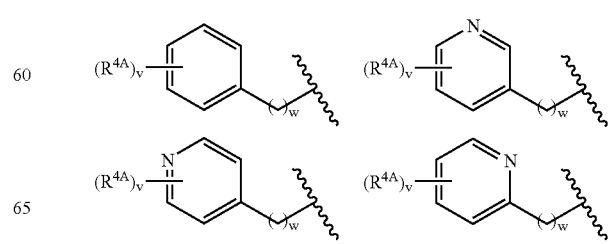

-continued

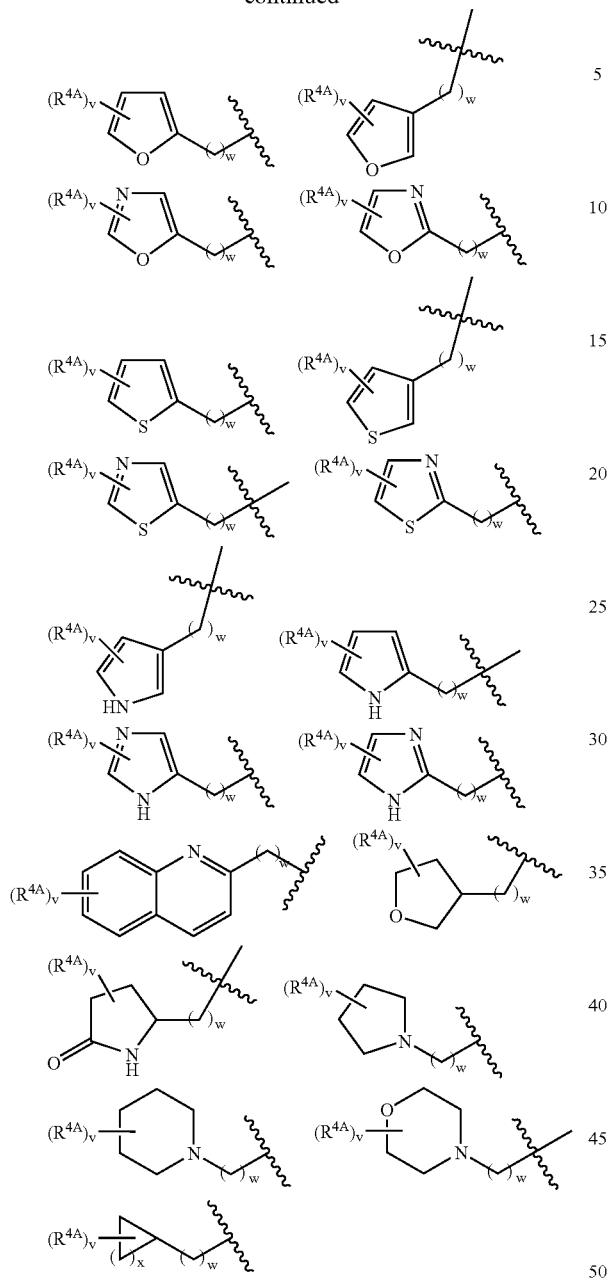

wherein each occurrence of $R^{4A}$ is independently hydrogen, alkyl, heteroalkyl, aryl, heteroaryl, -(alkyl)aryl or -(alkyl)heteroaryl, $-OR^{4B}$, $-SR^{4B}$, $-N(R^{4B})_2$, $-SO_2N(R^{4B})_2$, $-C(=O)N(R^{4B})_2$, halogen, $-CN$, $-NO_2$, $-C(=O)OR^{4B}$, $-N(R^{4B})C(=O)R^{4C}$, wherein each occcurrence of $R^{4B}$ and $R^{4C}$ is independently hydrogen, lower alkyl, lower heteroalkyl, aryl, heteroaryl, -(alkyl)aryl or -(alkyl)heteroaryl, wherein v and w are each independently integers from 0 to 3 and x is an integer from 1 to 6; whereby each of the foregoing alkyl and heteroalkyl moieties may be linear or branched, substituted or unsubstituted, cyclic or acyclic, and each of the foregoing aryl, heteroaryl, -(alkyl)aryl and -(alkyl)heteroaryl moieties may be substituted or unsusbtituted.

19. The compound of claim 16, wherein $R^4$ is methyl, ethyl, propyl or one of:

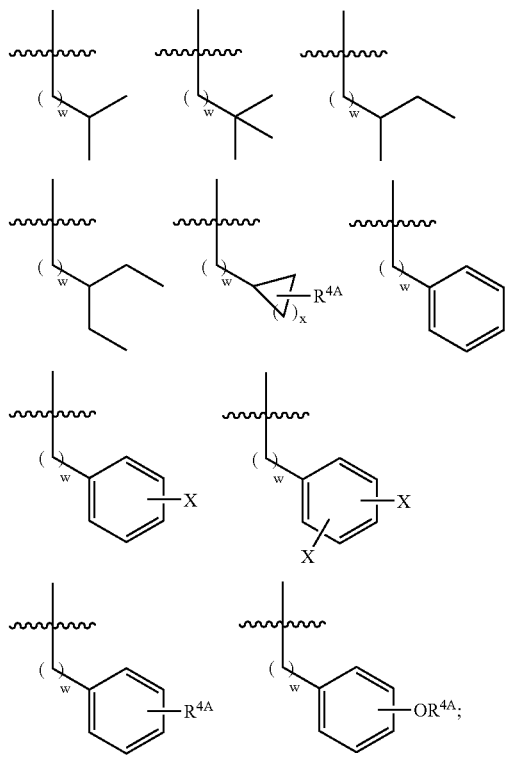

wherein each occcurrence of $R^{4A}$ is independently hydrogen, lower alkyl or $C(=O)OR^{4B}$, wherein $R^{4B}$ is hydrogen, lower alkyl, lower heteroalkyl, aryl, heteroaryl, -(alkyl)aryl or -(alkyl)heteroaryl; each occurrence of X is independently a halogen; w is an integer from 0 to 3 and x is an integer from 1 to 6; whereby each of the foregoing alkyl and heteroalkyl moieties may be linear or branched, substituted or unsubstituted, cyclic or acyclic, and each of the foregoing aryl, heteroaryl, -(alkyl)aryl and -(alkyl)heteroaryl moieties may be substituted or unsusbtituted.

20. The compound of claim 19, wherein each occurrence of X is independenly chlorine or fluorine and $R^{4A}$ is methyl.

21. The compound of claim 16, wherein $R^4$ is methyl, ethyl, propyl or one of:

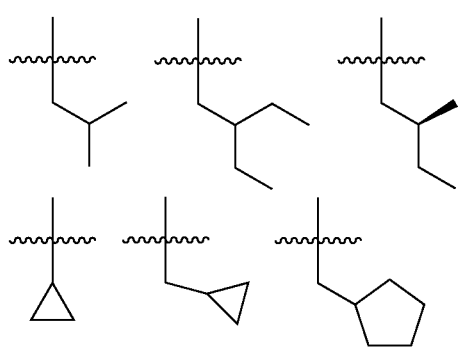

-continued

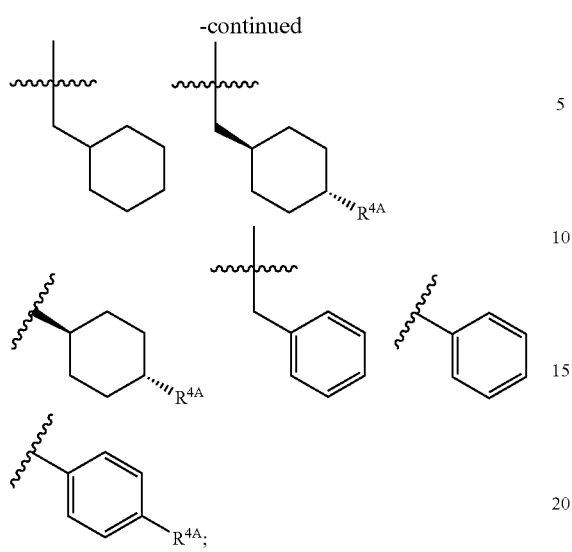

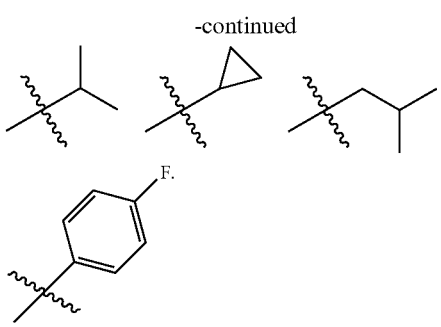

wherein R⁴ᴬ is hydrogen, hydroxyl, lower alkyl, lower alkoxy, halogen, C(=O)OR⁴ᴮ, aryl, heteroaryl, -(alkyl)aryl or -(alkyl)heteroaryl, wherein R⁴ᴮ is hydrogen, lower alkyl, lower heteroalkyl, aryl, heteoraryl, -(alkyl)aryl, -(alkyl)heteroaryl, -(heteroalkyl)aryl or -(heteroalkyl)heteroaryl.

22. The compound of claim 16, wherein R⁴ is methyl, ethyl, propyl, isopropyl or one of:

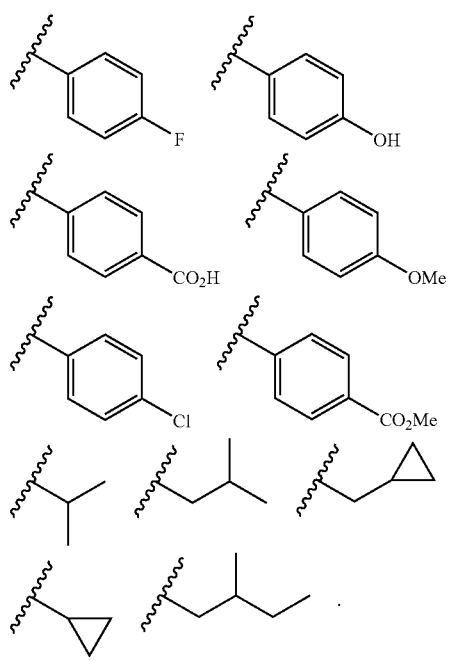

23. The compound of claim 16, wherein R⁴ has one of the following structures:

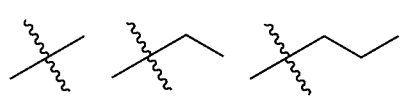

24. The compound of claim 1, wherein:
R¹ has one of the following structures:

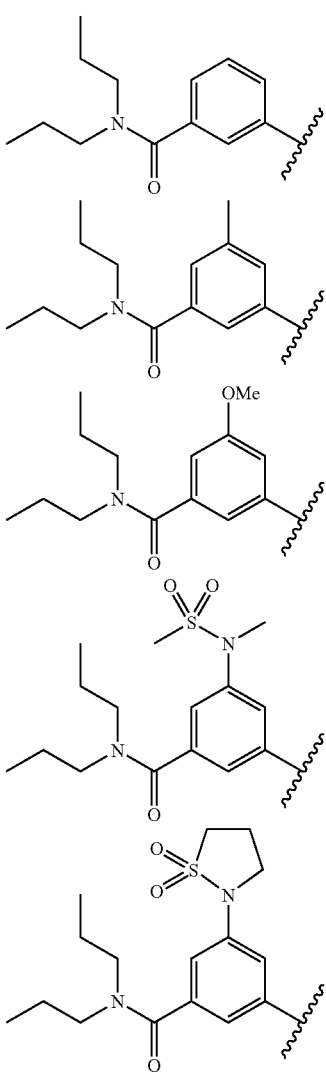

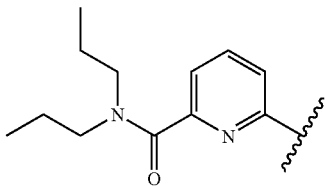

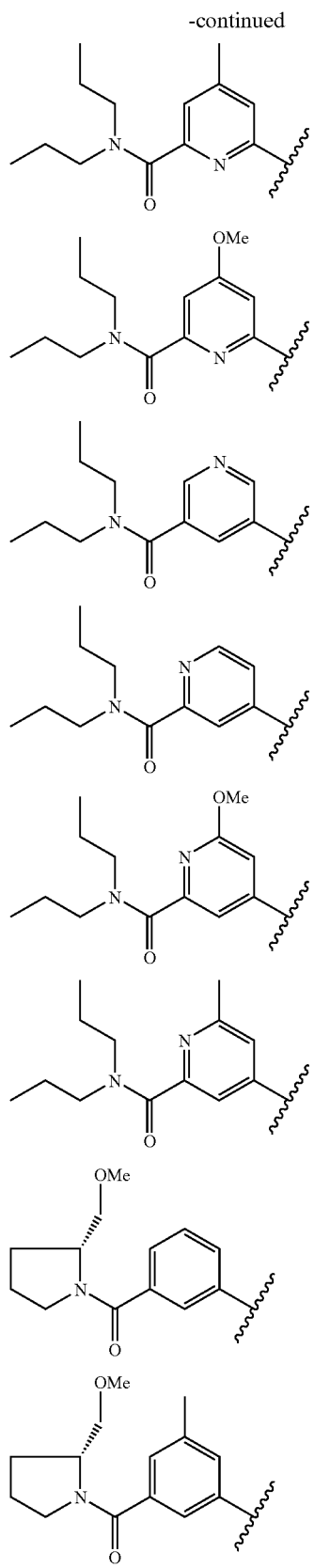
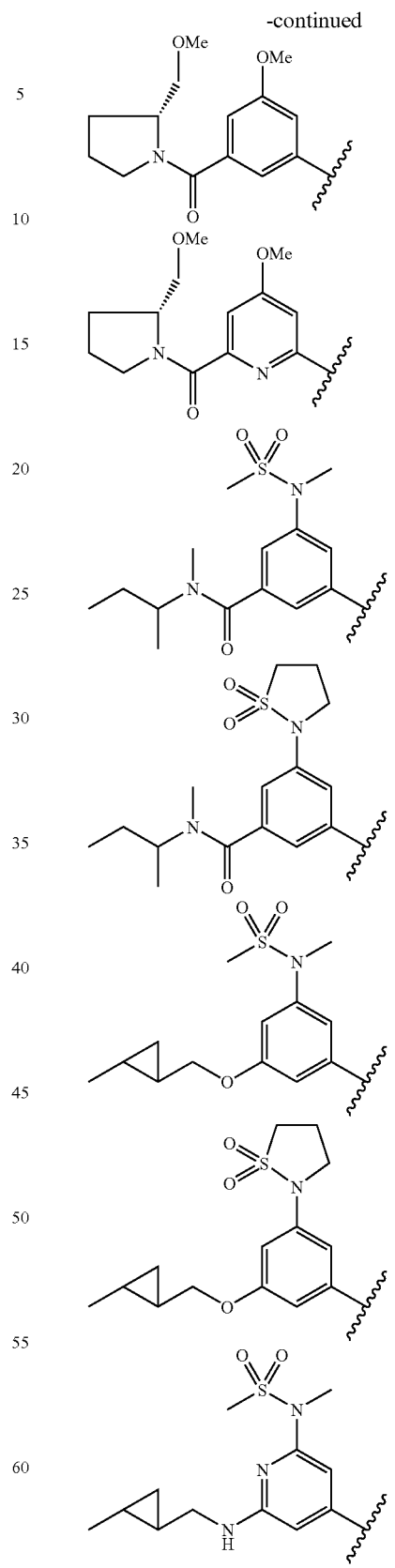

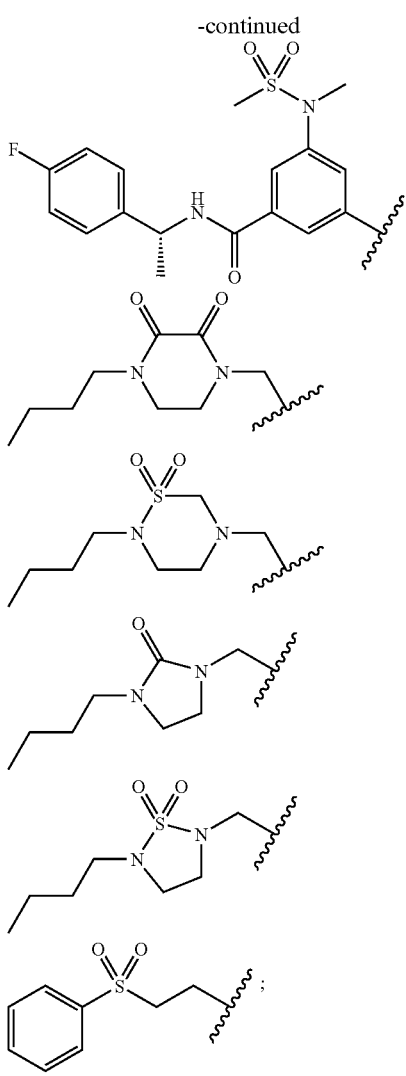

R² is lower alkyl, —CH₂NR²ᴬR²ᴮ or —(CH₂)phenyl, wherein the phenyl group is optionally substituted with one or more occurrences of R²ᶜ, wherein R²ᶜ is hydrogen, alkyl, alkoxy or halogen; and wherein R²ᴬ and R²ᴮ are each independently hydrogen, lower alkyl, lower heteroalkyl, aryl, heteroaryl, -(alkyl)aryl or -(alkyl)heteroaryl; whereby each of the foregoing alkyl and heteroalkyl moieties may be linear or branched, substituted or unsubstituted, cyclic or acylic, and each of the foregoing aryl, heteroaryl, -(alkyl)aryl and -(alkyl)heteroaryl moieties may be substituted or unsusbtituted;

R⁴ is substituted or unsubstituted, linear or branched, cyclic or acyclic alkyl, phenyl or —(CH₂)phenyl, wherein the phenyl group is optionally substituted with one or more occurrences of R⁴ᴬ, wherein R⁴ᴬ is hydrogen, hydroxyl, alkyl, alkoxy or halogen; and R^{X2A} is a substituted or unsubstituted, linear or branched lower alkyl moiety.

25. A pharmaceutical composition comprising a compound of claim 1, and a pharmaceutically acceptable carrier or diluent, optionally further comprising an additional therapeutic agent.

26. The pharmaceutical composition of claim 25, wherein the compound is present in an amount effective to inhibit β-secretase activity.

27. The pharmaceutical composition of claim 25, wherein the additional therapeutic agent is an agent for the treatment of Alzheimer's Disease.

28. A method for treating a disease characterized by β-amyloid deposits in the brain comprising administering to a patient a therapeutically effective amount of a compound of claim 1.

29. The method of claim 28, wherein the disease is Alzheimer's disease MCI (mild cognitive impairment), Down's syndrome, Hereditary Cerebral Hemmorhage with Amyloidosis of the Dutch-Type, cerebral amyloid angiopathy, other degenerative dementias, including dementias of mixed vascular and degenerative origin, dementia associated with Parkinson's disease, dementia associated with progressive supranuclear palsy, dementia associated with cortical basal degeneration, and diffuse Lewy body type Alzheimer's disease.

* * * * *